United States Patent
Wilm et al.

(10) Patent No.: US 10,738,120 B2
(45) Date of Patent: Aug. 11, 2020

(54) DIAGNOSTIC ANTI-PD-L1 ANTIBODY AND USE THEREOF

(71) Applicants: Merck Patent GmbH, Darmstadt (DE); Pfizer Inc., New York, NY (US)

(72) Inventors: Claudia Wilm, Darmstadt (DE); Klaus Schneider, Wiesbaden (DE); Heike Dahmen, Darmstadt (DE)

(73) Assignees: Merck Patent GmbH, Darmstadt (DE); Pfizer Inc., New York, NY (US)

( * ) Notice: Subject to any disclaimer, the term of this patent is extended or adjusted under 35 U.S.C. 154(b) by 0 days.

(21) Appl. No.: 16/334,699

(22) PCT Filed: Sep. 20, 2017

(86) PCT No.: PCT/EP2017/073712
§ 371 (c)(1),
(2) Date: Mar. 19, 2019

(87) PCT Pub. No.: WO2018/054940
PCT Pub. Date: Mar. 29, 2018

(65) Prior Publication Data
US 2019/0211104 A1 Jul. 11, 2019

(30) Foreign Application Priority Data
Sep. 20, 2016 (EP) .................................... 16189804

(51) Int. Cl.
| | | |
|---|---|---|
| *C07K 16/28* | (2006.01) | |
| *G01N 33/574* | (2006.01) | |
| *C07K 16/30* | (2006.01) | |
| *A61K 45/06* | (2006.01) | |
| *A61P 35/00* | (2006.01) | |
| *A61K 39/395* | (2006.01) | |

(52) U.S. Cl.
CPC ........ *C07K 16/2827* (2013.01); *A61K 39/395* (2013.01); *A61K 45/06* (2013.01); *A61P 35/00* (2018.01); *C07K 16/30* (2013.01); *G01N 33/57492* (2013.01); *C07K 2317/10* (2013.01); *C07K 2317/20* (2013.01); *C07K 2317/34* (2013.01); *C07K 2317/51* (2013.01); *C07K 2317/515* (2013.01); *C07K 2317/54* (2013.01); *C07K 2317/55* (2013.01); *C07K 2317/622* (2013.01); *G01N 2333/70532* (2013.01); *G01N 2333/70596* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly |
| 5,892,019 A | 4/1999 | Schlom |
| 7,732,168 B2 | 6/2010 | Pytela |

FOREIGN PATENT DOCUMENTS

| | | |
|---|---|---|
| WO | WO2007110205 | 10/2007 |
| WO | WO2014165422 | 10/2014 |
| WO | WO2015181342 | 12/2015 |
| WO | WO2016007235 | 1/2016 |

OTHER PUBLICATIONS

Mariuzza, R.A. etal. The Structural Basis of Antigen-Antibody Recognition1 Annu. Rev. Biophys. Biphys. Chem. 16:139-159, 1987.*
Maccallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Goel et al. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
Jian H, Yu Y, Shen L, Lu S. Oral 1.03: Frequent PD-L1 expression in thymic squamous cell carcinoma of Chinese patients. J Thorac Dis 2015;7(Suppl 3):AB056. doi: 10.3978/j.issn.2072-1439.2015. AB056.*
Alivisatos, "Perspectives on the Physical Chemistry of Semiconductor Nanocrystals," Journal of Physical Chemistry, 100:13226-13239 (1996).
Alivisatos, "Semiconductor Clusters, Nanocrystals, and Quantum Dots," Science, 271(5251):933-937 (1996).
Anonymous, "Antibodies," A Laboratory Manual, Second Edition, Chapter 7, Edited by Edward A. Greenfield, CSH Press, ISBN 978-1-936113-81-1 (2014) (59 pages).
Anonymous, "Cancer Cell Culture: Methods and Protocols," Methods in Molecular Medicine, S.P. Landon Ed., Humana Press, ISBN: 978-1588290793 (345 pages).
Anonymous, "CRC Handbook of Chemistry and Physics," 83rd edition, Lide, David R. (Editor), CRC Press, Boca Raton, Fla. (2002) (25 pages).

(Continued)

*Primary Examiner* — Nora M Rooney
(74) *Attorney, Agent, or Firm* — Haley Guiliano LLP; James F. Haley, Jr.; Brian M. Gummow

(57) ABSTRACT

The present invention provides for an antibody or antigen-binding fragment thereof which binds to an epitope within human PD-L1 with high specificity and reproducibility. The inventive antibody or antigen-binding fragment thereof may be used in assessing PD-L1 expression in tissue samples to aid in patient stratification. The present invention further provides methods of producing the inventive antibody.

20 Claims, 14 Drawing Sheets
Specification includes a Sequence Listing.

(56) References Cited

OTHER PUBLICATIONS

Anonymous, "Enzyme-Linked Immunosorbent Assays (ELISA)," Current Protocols in Molecular Biology, 11.2.1-11.2.22 (1991).
Anonymous, "Immunoassays," Current Protocols in Molecular Biology, Chapter 11:Unit 11.1.1-11.1.7 (2000) (4 pages).
Anonymous, "Immunohistochemical Staining Methods," 5th edition, published by DAKO North America, Inc. (2009) (172 pages).
Anonymous, "Purification of Monoclonal Antibodies," Current Protocols in Molecular Biology, 11.11.1-11.11.5 (1997).
Bird, et al., "Single-chain antigen-binding proteins," Science, 242(4877):423-426 (1988).
Carvajal-Hausdorf, et al., "Quantitative measurement of cancer tissue biomarkers in the lab and in the clinic," Laboratory Investigation, 95(4):385-396 (2015).
Charette, et al., "Protein quantification by chemiluminescent Western blotting. elimination of the antibody factor by dilution series and calibration curve," Journal of Immunological Methods, 353(1-02):148-150 (2010).
Cherry, "Codon usage table for Xenopus laevis," Methods in Cell Biology, 36:675-677 (1991).
Chin, et al., "Codon Optimization OnLine (COOL): a web-based multi-objective optimization platform for synthetic gene design.," Bioinformatics, 30(15):2210-2212 (2014).
Chowdhury, et al., "Programmed death-ligand 1 overexpression is a prognostic marker for aggressive papillary thyroid cancer and its variants," Oncotarget, 7(22):32318-32328 (2016).
Davis, et al., "SEEDbodies: fusion proteins based on strand-exchange engineered domain (SEED) CH3 heterodimers in an Fc analogue platform for asymmetric binders or immunofusions and bispecific antibodies," Protein Engineering, Design & Selection, 23(4):195-202 (2010).
Gadiot, et al., "Overall survival and PD-L1 expression in metastasized malignant melanoma," Cancer, 117(10):2192-2201 (2011).
Gallagher et al., "Immunoblotting and Immunodetection," Current Protocols in Molecular Biology, 10.8.1-10.8.28 (2008).
Gandini, et al., "PD-L1 expression in cancer patients receiving anti PD-1/PD-L1 antibodies: A systematic review and meta-analysis," Clinical Reviews in Oncology/Hematology, 100:88-98 (2016).
Goldstein et al., "Immunohistochemitry," Current Protocols in Molecular Biology, 14.6.1-14.6.23 (2008).
Heidebrecht, et al., "Improved semiquantitative Western blot technique with increased quantification range," Journal of Immunological Methods, 345(1-2):40-48 (2009).
Herbst, et al., "Predictive correlates of response to the anti-PD-L1 antibody MPDL3280A in cancer patients," Nature, 515(7528)563-567 (2014).
Ho et al., Site-Directed mutagenisis by overlap extension using the polymerase chain reaction, Gene, 77:51-59 (1989).
Hofman et al., "Immunohisochemistry," Current Protocols in Immunology, 21.4.21-21.4.26 (2013).
Holmes, et al., "Protein labeling with fluorescent probes," Methods in Cell Biology, 63:185-204 (2001).
Hong, et al., "Frequent PD-L1 expression in thymic squamous cell carcinoma of Chinese patients," Journal of Thoracic Disease, 7(3):S181-S182 (2015).
Hopwood, "Fixatives and fixation: a review," Histochemical Journal, 1(4):323-360 (1969).
Ilie, et al., "Comparative study of the PD-L1 status between surgically resected specimens and matched biopsies of NSCLC patients reveal major discordances: a potential issue for anti-PD-L1 therapeutic strategies," Annals of Oncology, 27(1):147-153 (2016).
Jorgensen, "Companion diagnostic assays for PD-1/PD-L1 checkpoint inhibitors in NSCLC," Expert Review of Molecular Diagnostics, 16(2):131-133 (2016).
Kaufman, et al., "Avelumab in patients with chemotherapy-refractory metastatic Merkel cell carcinoma: a multicentre, single-group, open-label, phase 2 trial," Lancet Oncology, 17(10):1374-1385 (2016).
King, et al., "Improved tumor targeting with chemically cross-linked recombinant antibody fragments," Cancer Research, 54(23):6176-6185 (1994).
Klimatcheva, et al., "Lentiviral Vectors and Gene Therapy," Frontiers in Bioscience, 4:481-496 (1999).
Koh, et al., "An internal ribosome entry site (IRES) mutant library for tuning expression level of multiple genes in mammalian cells," PLOS One, 8(12):e82100 (2013).
Kohler, et al., Continuous cultures of fused cells secreting antibody of predefined specificity, Nature, 256:495-497 (1975).
Kononen, et al., "Tissue microarrays for high-throughput molecular profiling of tumor specimens," Nature Medicine, 4(7):844-847 (1998).
Kriz, et al., "A plasmid-based multigene expression system for mammalian cells," Nature Communications, 1:120 (2010).
Mansur, et al., "Biomolecule-quantum dot systems for bioconjugation applications," Colloids and Surfaces B: Biointerfaces, 84(2):360-368 (2011).
Mao, et al., "Conjugation of fluorochromes to antibodies," Immunocytochemical Methods and Protocols, Methods in Molecular Biology; 588:43-48 (2010).
Milenic, et al., "Construction, binding properties, metabolism, and tumor targeting of a single-chain Fv derived from the pancarcinoma monoclonal antibody CC49," Cancer Research, 51(23 Pt 1):6363-6371 (1991).
Mitra, et al., "Technologies for deriving primary tumor cells for use in personalized cancer therapy," Trends in Biotechnology, 31(6):347-354 (2013).
Mittendorf, et al., "PD-L1 expression in triple-negative breast cancer," Cancer Immunology Research, 2(4):361-370 (2014).
Morganstern, et al., "A series of mammalian expression vectors and characterisation of their expression of a reporter gene in stably and transiently transfected cells," Nucleic Acids Research, 18(4):1068 (1990).
Natarajan, et al., "Construction of di-scFv through a trivalent alkyne-azide 1,3-dipolar cycloaddition," Chemical Communications, (7):695-697 (2007).
Pantoliano et al., "Conformational stability, folding, and ligand-binding affinity of single-chain Fv immunoglobulin fragments expressed in *Escherichia coli*," Biochemistry, 30:10117-10125 (1991).
Pardoll, "The blockade of immune checkpoints in cancer immunotherapy," Nature Reviews Cancer, 12(4):252-264 (2016).
Pesole, et al., "A backtranslation method based on codon usage strategy," Nucleic Acids Research, 16(5):1715-1728 (1988).
Schroeder, et al., "Structure and function of immunoglobulins," Journal of Allergy and Clinical Immunology, 125(2 Suppl 2): 41-52 (2010).
Sharp, et al., "Codon usage patterns in *Escherichia coli, Bacillus subtilis, Saccharomyces cerevisiae, Schizosaccharomyces pombe, Drosophila melanogaster* and *Homo sapiens*; a review of the considerable within-species diversity," Nucleic Acids Research, 16(17):8207-8211 (1988).
Smith, et al., "Quantitative and qualitative characterization of Two PD-L1 clones: SP263 and E1L3N," Diagnostic Pathology, 11(1):44 (2016).
Song, et al., "Principles of conjugating quantum dots to proteins via carbodiimide chemistry," Nanotechnology, 22:494006 (2011) (7 pages).
Spieker-Polet, et al., "Rabbit monoclonal antibodies: generating a fusion partner to produce rabbit-rabbit hybridomas," PNAS; 92(20):9348-9352 (1995).
Starkie, et al., "Generation of Recombinant Monoclonal Antibodies from Immunised Mice and Rabbits via Flow Cytometry and Sorting of Antigen-Specific IgG+ Memory B Cells," PLOS One, 11(3):e0152282 (2016).
Takkinen, et al., "An active single-chain antibody containing a cellulase linker domain is secreted by *Escherichia coli*," Protein Engineering, 4(7):837-841 (1991).
Topalian, et al., "Safety, activity, and immune correlates of anti-PD-1 antibody in cancer," New England Journal of Medicine, 366(26):2443-2454 (2012).
Vink, et al., "A simple, robust and highly efficient transient expression system for producing antibodies," Methods, 65(1):5-10 (2014).

(56) References Cited

OTHER PUBLICATIONS

Ward, et al., "Binding activities of a repertoire of single immunoglubulin variable domains secreted from *Escherichia coli*," Nature, 341:544-546 (1989).

Weller, "Colloidal Semiconductor Q-Particles: Chemistry in the Transition Regional Between Solid State and Molecules," Angewandte Chemie International Edition, 32:41-53 (1993).

Zhang, et al., "Recombinase-mediated cassette exchange (RMCE) for monoclonal antibody expression in the commercially relevant CHOK1SV cell line," Biotechnology Progress, 31(6):1645-1656 (2015).

Zhong, et al, "Lower expression of PD-1 and PD-L1 in peripheral blood from patients with chronic ITP," Hematology, 21(9):552-557(2016).

* cited by examiner

| Samples | Coating w/MKP-1A Antigen ( 1 ug/ml@50ul/well) | | | | | | | | | |
|---|---|---|---|---|---|---|---|---|---|---|
| O.D | MKP-1A-73-10 | | | | | | | | | |
| | Unpurified Antibody | | Purified Antibody | | Flow Through | | N/A | | N/A | |
| Dilution | Test 1 | Test 2 | Test 1 | Test 2 | Test 1 | Test 2 | Test 1 | Test 2 | Test 1 | Test 2 |
| 1:250 | 1.20 | 1.24 | 1.82 | 2.00 | 0.13 | 0.10 | 0.07 | 0.08 | 0.07 | 0.08 |
| 1:750 | 0.99 | 0.90 | 1.79 | 1.81 | 0.10 | 0.09 | 0.07 | 0.07 | 0.06 | 0.07 |
| 1:2250 | 0.52 | 0.49 | 1.97 | 2.26 | 0.08 | 0.07 | 0.08 | 0.06 | 0.06 | 0.08 |
| 1:6750 | 0.23 | 0.22 | 1.96 | 1.89 | 0.07 | 0.06 | 0.07 | 0.06 | 0.07 | 0.07 |
| 1:20250 | 0.13 | 0.12 | 1.30 | 1.31 | 0.07 | 0.07 | 0.06 | 0.08 | 0.08 | 0.06 |
| 1:60750 | 0.08 | 0.09 | 0.71 | 0.68 | 0.08 | 0.06 | 0.06 | 0.07 | 0.07 | 0.07 |
| 1:182250 | 0.07 | 0.08 | 0.36 | 0.33 | 0.07 | 0.06 | 0.07 | 0.06 | 0.06 | 0.07 |
| 1xPBS | 0.05 | 0.06 | 0.08 | 0.08 | 0.07 | 0.07 | 0.06 | 0.07 | 0.07 | 0.06 |

*ELISA Brief Protocol:*
1) *MKP-1A antigen coated (1 ug/ml, 50 ul/well), over night*
2) *Samples at serial dilutions (50 ul/well), RT, 1.5 hr.*
3) *AP Gt x Rb IgG (1:2500), 50 ul/well, RT, 1 hr.*
4) *AP substrate, 50 ul/well, RT, 15 min*
5) *Stopping solution, 50 ul/well, OD405nm*

FIGURE 1

A
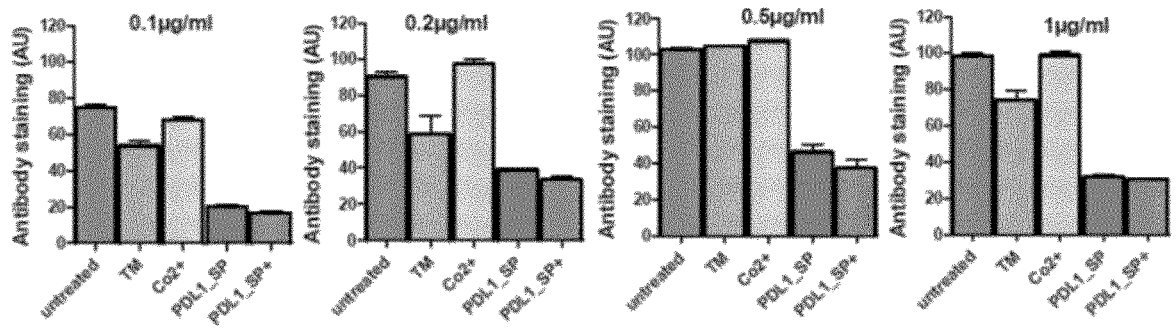
B
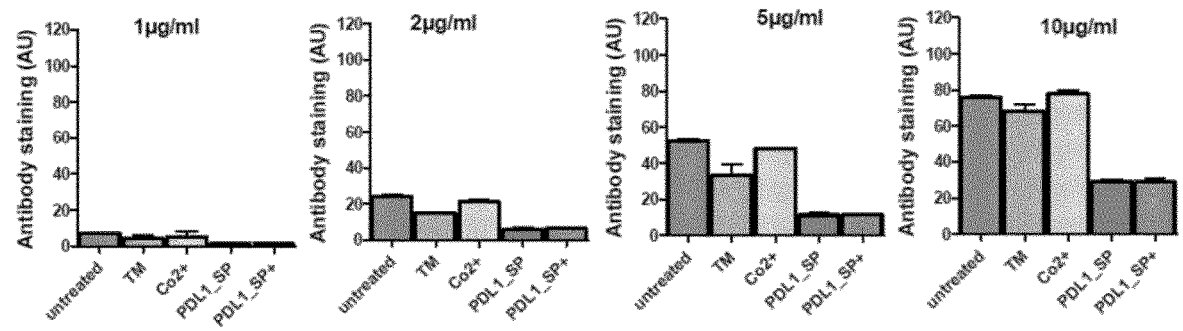
| Cell line MDA-MB 231 | |
|---|---|
| untreated | Untreated |
| TM | Treated with transfection medium |
| Co2+ | Treated with control siRNA |
| PDL1_SP+ | Treated with PD-L1 siRNA 2 |
| PDL1_SP | Treated with PD-L1 siRNA 1 |
FIGURE 3

A
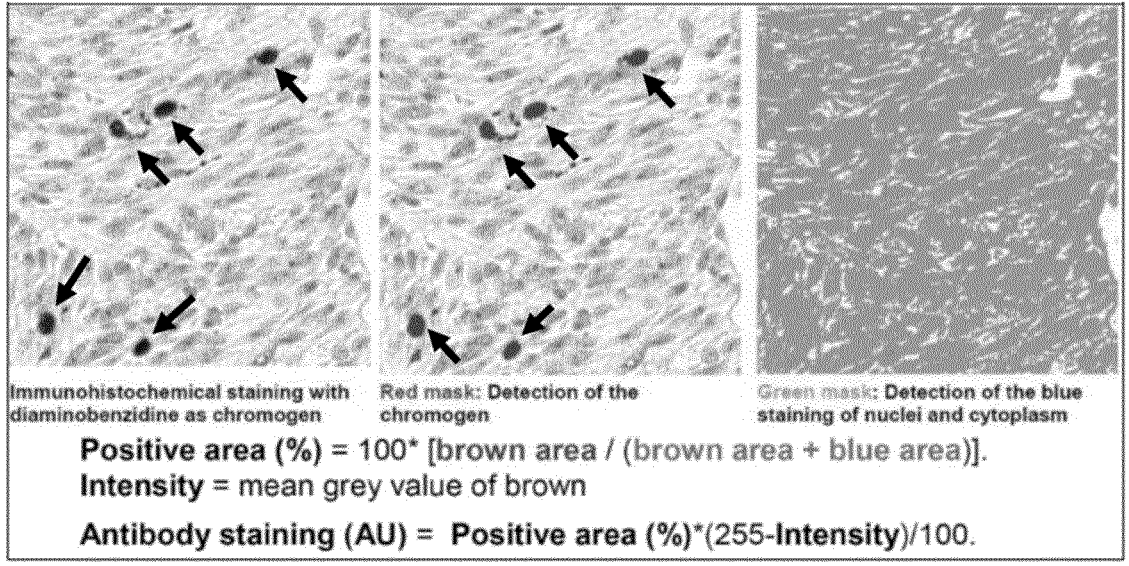
B
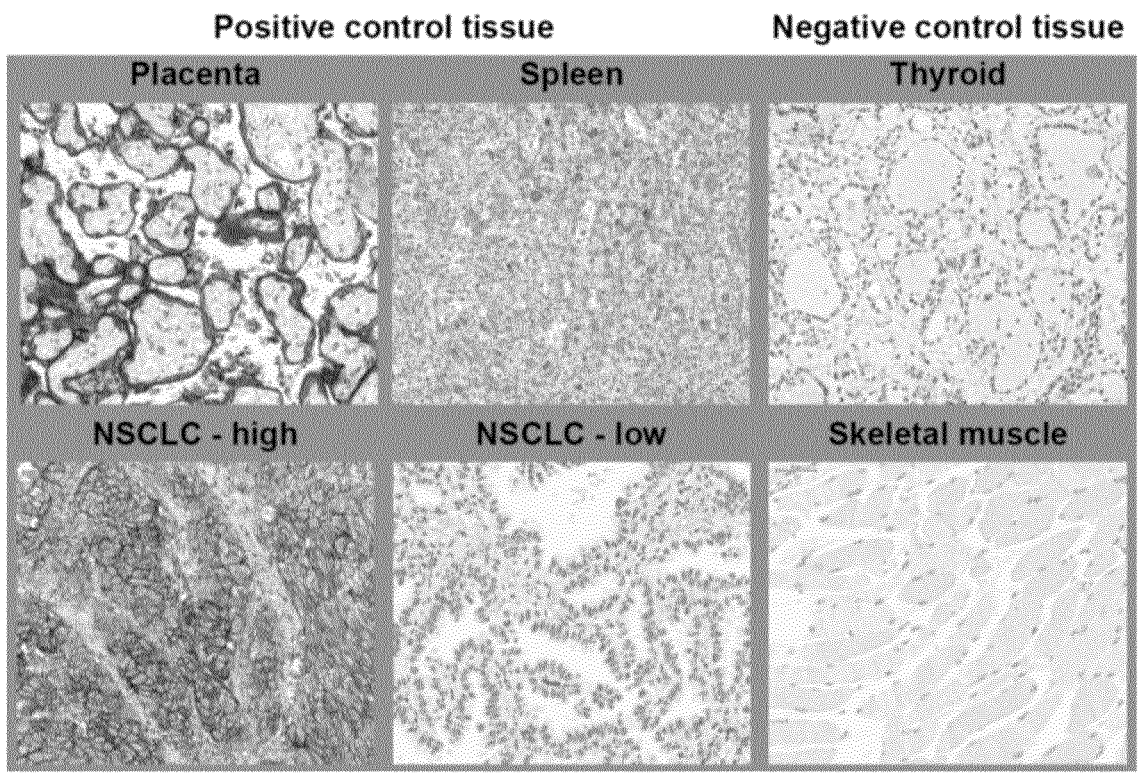
FIGURE 7

A

B

| Parameter | MKP1B19610 (2µg/ml) | MKP1B19610 (1 µg/ml) |
|---|---|---|
| Number of XY Pairs | 55 | 55 |
| Pearson r | 0.6503 | 0.7088 |
| 95% confidence interval | 0.4652 to 0.7809 | 0.5461 to 0.8199 |
| P value (two-tailed) | < 0.0001 | < 0.0001 |
| P value summary | **** | **** |
| Is the correlation significant? (alpha=0.05) | Yes | Yes |
| R square | 0.4229 | 0.5024 |

```
                        SEQUENCE LISTING

<160> NUMBER OF SEQ ID NOS: 117

<210> SEQ ID NO 1
<211> LENGTH: 31
<212> TYPE: PRT
<213> ORGANISM: Artificial Sequence
<220> FEATURE:
<223> OTHER INFORMATION: PD-L1 cytoplasmic domain (partial)

<400> SEQUENCE: 1

Arg Leu Arg Lys Gly Arg Met Met Asp Val Lys Lys Cys Gly Ile Gln
1               5                   10                  15

Asp Thr Asn Ser Lys Lys Gln Ser Asp Thr His Leu Glu Glu Thr
            20                  25                  30

<210> SEQ ID NO 2
<211> LENGTH: 15
<212> TYPE: PRT
<213> ORGANISM: Artificial Sequence
<220> FEATURE:
<223> OTHER INFORMATION: PD-L1 cytoplasmic partial cytoplasmic domain

<400> SEQUENCE: 2

Cys Gly Ile Gln Asp Thr Asn Ser Lys Lys Gln Ser Asp Thr His
1               5                   10                  15

<210> SEQ ID NO 3
<211> LENGTH: 26
<212> TYPE: PRT
<213> ORGANISM: Artificial Sequence
<220> FEATURE:
<223> OTHER INFORMATION: light chain sequence element

<400> SEQUENCE: 3

Ala Gln Val Leu Thr Gln Thr Pro Ser Pro Val Ser Ala Ser Val Gly
1               5                   10                  15

Ser Thr Val Thr Ile Asn Cys Gln Ala Ser
            20                  25

<210> SEQ ID NO 4
<211> LENGTH: 8
<212> TYPE: PRT
<213> ORGANISM: Artificial Sequence
<220> FEATURE:
<223> OTHER INFORMATION: light chain sequence element

<400> SEQUENCE: 4
```

Gln Ser Leu His Arg Asn Asn Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: light chain sequence element

<400> SEQUENCE: 5

Leu Ser Trp Phe Gln Gln Lys Pro Gly Gln Pro Pro Lys Gln Leu Ile
1               5                   10                  15

Tyr

<210> SEQ ID NO 6
<211> LENGTH: 4
<212> TYPE: PRT
<213> ORGANISM: Artificial Sequence
<220> FEATURE:
<223> OTHER INFORMATION: light chain sequence element with amino acid
      Xaa being absent
<220> FEATURE:
<221> NAME/KEY: VARIANT
<222> LOCATION: (4)..(4)

<400> SEQUENCE: 6

Gln Ala Ser Xaa
1

<210> SEQ ID NO 7
<211> LENGTH: 36
<212> TYPE: PRT
<213> ORGANISM: Artificial Sequence
<220> FEATURE:
<223> OTHER INFORMATION: light chain sequence element

<400> SEQUENCE: 7

Thr Leu Ala Ser Gly Val Ser Ser Arg Phe Ser Gly Ser Gly Ser Gly
1               5                   10                  15

Thr Gln Phe Thr Leu Thr Ile Ser Asp Val Val Cys Asp Asp Ala Ala
            20                  25                  30

Thr Tyr Tyr Cys
        35

<210> SEQ ID NO 8
<211> LENGTH: 10
<212> TYPE: PRT
<213> ORGANISM: Artificial Sequence
<220> FEATURE:
<223> OTHER INFORMATION: light chain sequence element

<400> SEQUENCE: 8

Leu Gly Gly Val Ser Gly Gly Pro Tyr Pro
1               5                   10

<210> SEQ ID NO 9
<211> LENGTH: 24
<212> TYPE: PRT
<213> ORGANISM: Artificial Sequence
<220> FEATURE:
<223> OTHER INFORMATION: heavy chain sequence element

<400> SEQUENCE: 9

Glu Gln Leu Val Glu Ser Gly Gly Gly Leu Val Thr Pro Gly Gly Ser

```
1               5                   10                  15
Leu Thr Leu Thr Cys Thr Val Ser
            20

<210> SEQ ID NO 10
<211> LENGTH: 8
<212> TYPE: PRT
<213> ORGANISM: Artificial Sequence
<220> FEATURE:
<223> OTHER INFORMATION: heavy chain sequence element

<400> SEQUENCE: 10

Thr Ile Asp Leu Ser Thr Phe Ala
1               5

<210> SEQ ID NO 11
<211> LENGTH: 17
<212> TYPE: PRT
<213> ORGANISM: Artificial Sequence
<220> FEATURE:
<223> OTHER INFORMATION: heavy chain sequence element

<400> SEQUENCE: 11

Ile Ser Trp Val Arg Gln Ala Pro Gly Lys Gly Leu Glu Trp Ile Gly
1               5                   10                  15

Thr

<210> SEQ ID NO 12
<211> LENGTH: 7
<212> TYPE: PRT
<213> ORGANISM: Artificial Sequence
<220> FEATURE:
<223> OTHER INFORMATION: heavy chain sequence element

<400> SEQUENCE: 12

Ile Asn Thr Asp Leu Thr Thr
1               5

<210> SEQ ID NO 13
<211> LENGTH: 37
<212> TYPE: PRT
<213> ORGANISM: Artificial Sequence
<220> FEATURE:
<223> OTHER INFORMATION: heavy chain sequence element

<400> SEQUENCE: 13

Tyr Tyr Val Asn Trp Ala Lys Gly Arg Phe Thr Ile Ser Lys Thr Ser
1               5                   10                  15

Ser Thr Thr Val Asp Leu Lys Met Thr Gly Leu Thr Ile Glu Asp Thr
            20                  25                  30

Ala Thr Tyr Phe Cys
            35

<210> SEQ ID NO 14
<211> LENGTH: 10
<212> TYPE: PRT
<213> ORGANISM: Artificial Sequence
<220> FEATURE:
<223> OTHER INFORMATION: heavy chain sequence element

<400> SEQUENCE: 14

Ala Arg Lys Leu Phe Gly Asn Gly Asn Val
1               5                   10
```

```
<210> SEQ ID NO 15
<211> LENGTH: 236
<212> TYPE: PRT
<213> ORGANISM: Artificial Sequence
<220> FEATURE:
<223> OTHER INFORMATION: light chain sequence

<400> SEQUENCE: 15

Met Asp Thr Arg Ala Pro Thr Gln Leu Leu Gly Leu Leu Leu Leu Trp
1               5                   10                  15

Leu Pro Gly Ala Thr Val Ala Gln Val Leu Thr Gln Thr Pro Ser Pro
                20                  25                  30

Val Ser Ala Ser Val Gly Ser Thr Val Thr Ile Asn Cys Gln Ala Ser
            35                  40                  45

Gln Ser Leu His Arg Asn Asn Tyr Leu Ser Trp Phe Gln Gln Lys Pro
        50                  55                  60

Gly Gln Pro Pro Lys Gln Leu Ile Tyr Gln Ala Ser Thr Leu Ala Ser
65                  70                  75                  80

Gly Val Ser Ser Arg Phe Ser Gly Ser Gly Ser Gly Thr Gln Phe Thr
                85                  90                  95

Leu Thr Ile Ser Asp Val Val Cys Asp Asp Ala Ala Thr Tyr Tyr Cys
            100                 105                 110

Leu Gly Gly Val Ser Gly Gly Pro Tyr Pro Phe Gly Gly Gly Thr Glu
        115                 120                 125

Val Val Val Lys Gly Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235

<210> SEQ ID NO 16
<211> LENGTH: 457
<212> TYPE: PRT
<213> ORGANISM: Artificial Sequence
<220> FEATURE:
<223> OTHER INFORMATION: heavy chain sequence

<400> SEQUENCE: 16

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Thr
                20                  25                  30

Pro Gly Gly Ser Leu Thr Leu Thr Cys Thr Val Ser Thr Ile Asp Leu
            35                  40                  45

Ser Thr Phe Ala Ile Ser Trp Val Arg Gln Ala Pro Gly Lys Gly Leu
        50                  55                  60

Glu Trp Ile Gly Thr Ile Asn Thr Asp Leu Thr Thr Tyr Tyr Val Asn
65                  70                  75                  80
```

```
Trp Ala Lys Gly Arg Phe Thr Ile Ser Lys Thr Ser Thr Thr Val
             85                  90                  95

Asp Leu Lys Met Thr Gly Leu Thr Ile Glu Asp Thr Ala Thr Tyr Phe
            100                 105                 110

Cys Ala Arg Lys Leu Phe Gly Asn Gly Asn Val Trp Gly Pro Gly Thr
            115                 120                 125

Leu Val Thr Val Ser Ser Gly Gln Pro Lys Ala Pro Ser Val Phe Pro
130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Thr Cys Pro
225                 230                 235                 240

Pro Pro Glu Leu Leu Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
    370                 375                 380

Ser Asp Ile Ser Val Glu Trp Glu Lys Asn Gly Lys Ala Glu Asp Asn
385                 390                 395                 400

Tyr Lys Thr Thr Pro Ala Val Leu Asp Ser Asp Gly Ser Tyr Phe Leu
                405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
    450                 455

<210> SEQ ID NO 17
<211> LENGTH: 711
<212> TYPE: DNA
<213> ORGANISM: Artificial Sequence
<220> FEATURE:
<223> OTHER INFORMATION: light chain sequence
```

<400> SEQUENCE: 17

```
atggacacga gggcccccac tcagctgctg gggctcctgc tgctctggct cccaggtgcc    60
acagttgccc aagtgctgac ccagacccca tcccccgtgt ctgcatctgt gggaagcaca   120
gtcaccatca attgccaggc cagtcagagt cttcatcgca caactactt atcctggttt    180
cagcagaaac cagggcagcc tcccaagcaa ctgatctatc aggcatccac tctggcatct   240
ggggtctcat cgcggttcag tggcagtgga tctgggacac agttcactct caccatcagc   300
gatgtggtgt gtgacgatgc tgccacttac tactgtctgg gcggtgttag tggtggtcct   360
tatccttcg cgcgagggac cgaggtggtc gtcaaaggtg atccagttgc acctactgtc   420
ctcatcttcc caccagctgc tgatcaggtg caactggaa cagtcaccat cgtgtgtgtg   480
gcgaataaat actttcccga tgtcaccgtc acctgggagg tggatggcac cacccaaaca   540
actggcatcg agaacagtaa aacaccgcag aattctgcag attgtaccta caacctcagc   600
agcactctga cactgaccag cacacagtac aacagccaca aagagtacac ctgcaaggtg   660
acccagggca cgacctcagt cgtccagagc ttcaataggg gtgactgtta g            711
```

<210> SEQ ID NO 18
<211> LENGTH: 1374
<212> TYPE: DNA
<213> ORGANISM: Artificial Sequence
<220> FEATURE:
<223> OTHER INFORMATION: heavy chain sequence

<400> SEQUENCE: 18

```
atggagactg ggctgcgctg gcttctcctg gtcgctgtgc tcaaaggtgt ccagtgtcag    60
gagcagctgg tggaatccgg aggaggcctg gtcacgcctg ggggatccct gacactcacc   120
tgcacagtct ctacaatcga cctcagtacc tttgcaataa gctgggtccg ccaggctcca   180
gggaaggggc tggagtggat cggaaccatt aatactgatc ttaccacata ctatgtgaat   240
tgggcgaaag gccgattcac catctccaaa acctcgtcga ccacggtgga tctgaaaatg   300
accggtctga caatcgagga cacggccacc tatttctgtg ccagaaaatt atttggaaat   360
ggtaatgtct ggggcccagg caccctggtc accgtctctt cagggcaacc taaggctcca   420
tcagtcttcc cactggcccc ctgctgcggg gacacaccca gctccacggt gaccctgggc   480
tgcctggtca aagggtacct cccggagcca gtgaccgtga cctggaactc gggcaccctc   540
accaatgggg tacgcacctt cccgtccgtc ggcagtcct caggcctcta ctcgctgagc   600
agcgtggtga gcgtgacctc aagcagccag cccgtcacct gcaacgtggc ccacccagcc   660
accaacacca agtggacaa gaccgttgcg ccctcgacat gcagcaagcc cacgtgccca   720
ccccctgaac tcctgggggg accgtctgtc ttcatcttcc ccccaaaacc caaggacacc   780
ctcatgatct cacgcacccc cgaggtcaca tgcgtggtgg tggacgtgag ccaggatgac   840
cccgaggtgc agttcacatg gtacataaac aacgagcagg tgcgcaccgc ccggccgccg   900
ctacgggagc agcagttcaa cagcacgatc cgcgtggtca gcaccctccc catcgcgcac   960
caggactggc tgaggggcaa ggagttcaag tgcaaagtcc acaacaaggc actcccggcc  1020
cccatcgaga aaaccatctc caaagccaga gggcagcccc tggagccgaa ggtctacacc  1080
atgggccctc ccggggagga gctgagcagc aggtcggtca gcctgacctg catgatcaac  1140
ggcttctacc cttccgacat ctcggtggag tgggagaaga cgggaaggc agaggacaac  1200
tacaagacca cgccggccgt gctggacagc gacggctcct acttcctcta cagcaagctc  1260
```

```
tcagtgccca cgagtgagtg gcagcggggc gacgtcttca cctgctccgt gatgcacgag   1320
gccttgcaca accactacac gcagaagtcc atctcccgct ctccgggtaa atga         1374
```

<210> SEQ ID NO 19
<211> LENGTH: 8
<212> TYPE: PRT
<213> ORGANISM: Artificial Sequence
<220> FEATURE:
<223> OTHER INFORMATION: epitope

<400> SEQUENCE: 19

Arg Leu Arg Lys Gly Arg Met Met
1               5

<210> SEQ ID NO 20
<211> LENGTH: 8
<212> TYPE: PRT
<213> ORGANISM: Artificial Sequence
<220> FEATURE:
<223> OTHER INFORMATION: epitope

<400> SEQUENCE: 20

Leu Arg Lys Gly Arg Met Met Asp
1               5

<210> SEQ ID NO 21
<211> LENGTH: 8
<212> TYPE: PRT
<213> ORGANISM: Artificial Sequence
<220> FEATURE:
<223> OTHER INFORMATION: epitope

<400> SEQUENCE: 21

Arg Lys Gly Arg Met Met Asp Val
1               5

<210> SEQ ID NO 22
<211> LENGTH: 8
<212> TYPE: PRT
<213> ORGANISM: Artificial Sequence
<220> FEATURE:
<223> OTHER INFORMATION: epitope

<400> SEQUENCE: 22

Gly Arg Met Met Asp Val Lys Lys
1               5

<210> SEQ ID NO 23
<211> LENGTH: 8
<212> TYPE: PRT
<213> ORGANISM: Artificial Sequence
<220> FEATURE:
<223> OTHER INFORMATION: epitope

<400> SEQUENCE: 23

Lys Gly Arg Met Met Asp Val Lys
1               5

<210> SEQ ID NO 24
<211> LENGTH: 8
<212> TYPE: PRT
<213> ORGANISM: Artificial Sequence
<220> FEATURE:
<223> OTHER INFORMATION: epitope

<400> SEQUENCE: 24

```
Arg Met Met Asp Val Lys Lys Cys
1               5

<210> SEQ ID NO 25
<211> LENGTH: 8
<212> TYPE: PRT
<213> ORGANISM: Artificial Sequence
<220> FEATURE:
<223> OTHER INFORMATION: epitope

<400> SEQUENCE: 25

Met Met Asp Val Lys Lys Cys Gly
1               5

<210> SEQ ID NO 26
<211> LENGTH: 8
<212> TYPE: PRT
<213> ORGANISM: Artificial Sequence
<220> FEATURE:
<223> OTHER INFORMATION: epitope

<400> SEQUENCE: 26

Met Asp Val Lys Lys Cys Gly Ile
1               5

<210> SEQ ID NO 27
<211> LENGTH: 8
<212> TYPE: PRT
<213> ORGANISM: Artificial Sequence
<220> FEATURE:
<223> OTHER INFORMATION: epitope

<400> SEQUENCE: 27

Asp Val Lys Lys Cys Gly Ile Gln
1               5

<210> SEQ ID NO 28
<211> LENGTH: 8
<212> TYPE: PRT
<213> ORGANISM: Artificial Sequence
<220> FEATURE:
<223> OTHER INFORMATION: epitope

<400> SEQUENCE: 28

Val Lys Lys Cys Gly Ile Gln Asp
1               5

<210> SEQ ID NO 29
<211> LENGTH: 8
<212> TYPE: PRT
<213> ORGANISM: Artificial Sequence
<220> FEATURE:
<223> OTHER INFORMATION: epitope

<400> SEQUENCE: 29

Lys Lys Cys Gly Ile Gln Asp Thr
1               5

<210> SEQ ID NO 30
<211> LENGTH: 8
<212> TYPE: PRT
<213> ORGANISM: Artificial Sequence
<220> FEATURE:
<223> OTHER INFORMATION: epitope

<400> SEQUENCE: 30

Lys Cys Gly Ile Gln Asp Thr Asn
```

```
1               5

<210> SEQ ID NO 31
<211> LENGTH: 8
<212> TYPE: PRT
<213> ORGANISM: Artificial Sequence
<220> FEATURE:
<223> OTHER INFORMATION: epitope

<400> SEQUENCE: 31

Cys Gly Ile Gln Asp Thr Asn Ser
1               5

<210> SEQ ID NO 32
<211> LENGTH: 8
<212> TYPE: PRT
<213> ORGANISM: Artificial Sequence
<220> FEATURE:
<223> OTHER INFORMATION: epitope

<400> SEQUENCE: 32

Gly Ile Gln Asp Thr Asn Ser Lys
1               5

<210> SEQ ID NO 33
<211> LENGTH: 8
<212> TYPE: PRT
<213> ORGANISM: Artificial Sequence
<220> FEATURE:
<223> OTHER INFORMATION: epitope

<400> SEQUENCE: 33

Ile Gln Asp Thr Asn Ser Lys Lys
1               5

<210> SEQ ID NO 34
<211> LENGTH: 8
<212> TYPE: PRT
<213> ORGANISM: Artificial Sequence
<220> FEATURE:
<223> OTHER INFORMATION: epitope

<400> SEQUENCE: 34

Gln Asp Thr Asn Ser Lys Lys Gln
1               5

<210> SEQ ID NO 35
<211> LENGTH: 8
<212> TYPE: PRT
<213> ORGANISM: Artificial Sequence
<220> FEATURE:
<223> OTHER INFORMATION: epitope

<400> SEQUENCE: 35

Asp Thr Asn Ser Lys Lys Gln Ser
1               5

<210> SEQ ID NO 36
<211> LENGTH: 8
<212> TYPE: PRT
<213> ORGANISM: Artificial Sequence
<220> FEATURE:
<223> OTHER INFORMATION: epitope

<400> SEQUENCE: 36

Thr Asn Ser Lys Lys Gln Ser Asp
1               5
```

```
<210> SEQ ID NO 37
<211> LENGTH: 8
<212> TYPE: PRT
<213> ORGANISM: Artificial Sequence
<220> FEATURE:
<223> OTHER INFORMATION: epitope

<400> SEQUENCE: 37

Asn Ser Lys Lys Gln Ser Asp Thr
1               5

<210> SEQ ID NO 38
<211> LENGTH: 8
<212> TYPE: PRT
<213> ORGANISM: Artificial Sequence
<220> FEATURE:
<223> OTHER INFORMATION: epitope

<400> SEQUENCE: 38

Ser Lys Lys Gln Ser Asp Thr His
1               5

<210> SEQ ID NO 39
<211> LENGTH: 8
<212> TYPE: PRT
<213> ORGANISM: Artificial Sequence
<220> FEATURE:
<223> OTHER INFORMATION: epitope

<400> SEQUENCE: 39

Lys Lys Gln Ser Asp Thr His Leu
1               5

<210> SEQ ID NO 40
<211> LENGTH: 8
<212> TYPE: PRT
<213> ORGANISM: Artificial Sequence
<220> FEATURE:
<223> OTHER INFORMATION: epitope

<400> SEQUENCE: 40

Lys Gln Ser Asp Thr His Leu Glu
1               5

<210> SEQ ID NO 41
<211> LENGTH: 8
<212> TYPE: PRT
<213> ORGANISM: Artificial Sequence
<220> FEATURE:
<223> OTHER INFORMATION: epitope

<400> SEQUENCE: 41

Gln Ser Asp Thr His Leu Glu Glu
1               5

<210> SEQ ID NO 42
<211> LENGTH: 8
<212> TYPE: PRT
<213> ORGANISM: Artificial Sequence
<220> FEATURE:
<223> OTHER INFORMATION: epitope

<400> SEQUENCE: 42

Ser Asp Thr His Leu Glu Glu Thr
1               5
```

```
<210> SEQ ID NO 43
<211> LENGTH: 9
<212> TYPE: PRT
<213> ORGANISM: Artificial Sequence
<220> FEATURE:
<223> OTHER INFORMATION: epitope

<400> SEQUENCE: 43

Arg Leu Arg Lys Gly Arg Met Met Asp
1               5

<210> SEQ ID NO 44
<211> LENGTH: 9
<212> TYPE: PRT
<213> ORGANISM: Artificial Sequence
<220> FEATURE:
<223> OTHER INFORMATION: epitope

<400> SEQUENCE: 44

Leu Arg Lys Gly Arg Met Met Asp Val
1               5

<210> SEQ ID NO 45
<211> LENGTH: 9
<212> TYPE: PRT
<213> ORGANISM: Artificial Sequence
<220> FEATURE:
<223> OTHER INFORMATION: epitope

<400> SEQUENCE: 45

Arg Lys Gly Arg Met Met Asp Val Lys
1               5

<210> SEQ ID NO 46
<211> LENGTH: 9
<212> TYPE: PRT
<213> ORGANISM: Artificial Sequence
<220> FEATURE:
<223> OTHER INFORMATION: epitope

<400> SEQUENCE: 46

Lys Gly Arg Met Met Asp Val Lys Lys
1               5

<210> SEQ ID NO 47
<211> LENGTH: 9
<212> TYPE: PRT
<213> ORGANISM: Artificial Sequence
<220> FEATURE:
<223> OTHER INFORMATION: epiope

<400> SEQUENCE: 47

Gly Arg Met Met Asp Val Lys Lys Cys
1               5

<210> SEQ ID NO 48
<211> LENGTH: 9
<212> TYPE: PRT
<213> ORGANISM: Artificial Sequence
<220> FEATURE:
<223> OTHER INFORMATION: epitope

<400> SEQUENCE: 48

Arg Met Met Asp Val Lys Lys Cys Gly
1               5
```

-continued

```
<210> SEQ ID NO 49
<211> LENGTH: 9
<212> TYPE: PRT
<213> ORGANISM: Artificial Sequence
<220> FEATURE:
<223> OTHER INFORMATION: epitope

<400> SEQUENCE: 49

Met Met Asp Val Lys Lys Cys Gly Ile
1               5

<210> SEQ ID NO 50
<211> LENGTH: 9
<212> TYPE: PRT
<213> ORGANISM: Artificial Sequence
<220> FEATURE:
<223> OTHER INFORMATION: epitope

<400> SEQUENCE: 50

Met Asp Val Lys Lys Cys Gly Ile Gln
1               5

<210> SEQ ID NO 51
<211> LENGTH: 9
<212> TYPE: PRT
<213> ORGANISM: Artificial Sequence
<220> FEATURE:
<223> OTHER INFORMATION: epitope

<400> SEQUENCE: 51

Asp Val Lys Lys Cys Gly Ile Gln Asp
1               5

<210> SEQ ID NO 52
<211> LENGTH: 9
<212> TYPE: PRT
<213> ORGANISM: Artificial Sequence
<220> FEATURE:
<223> OTHER INFORMATION: epitope

<400> SEQUENCE: 52

Val Lys Lys Cys Gly Ile Gln Asp Thr
1               5

<210> SEQ ID NO 53
<211> LENGTH: 9
<212> TYPE: PRT
<213> ORGANISM: Artificial Sequence
<220> FEATURE:
<223> OTHER INFORMATION: epitope

<400> SEQUENCE: 53

Lys Lys Cys Gly Ile Gln Asp Thr Asn
1               5

<210> SEQ ID NO 54
<211> LENGTH: 9
<212> TYPE: PRT
<213> ORGANISM: Artificial Sequence
<220> FEATURE:
<223> OTHER INFORMATION: epitope

<400> SEQUENCE: 54

Lys Cys Gly Ile Gln Asp Thr Asn Ser
1               5

<210> SEQ ID NO 55
```

```
<211> LENGTH: 9
<212> TYPE: PRT
<213> ORGANISM: Artificial Sequence
<220> FEATURE:
<223> OTHER INFORMATION: epitope

<400> SEQUENCE: 55

Cys Gly Ile Gln Asp Thr Asn Ser Lys
1               5

<210> SEQ ID NO 56
<211> LENGTH: 9
<212> TYPE: PRT
<213> ORGANISM: Artificial Sequence
<220> FEATURE:
<223> OTHER INFORMATION: epitope

<400> SEQUENCE: 56

Gly Ile Gln Asp Thr Asn Ser Lys Lys
1               5

<210> SEQ ID NO 57
<211> LENGTH: 9
<212> TYPE: PRT
<213> ORGANISM: Artificial Sequence
<220> FEATURE:
<223> OTHER INFORMATION: epitope

<400> SEQUENCE: 57

Ile Gln Asp Thr Asn Ser Lys Lys Gln
1               5

<210> SEQ ID NO 58
<211> LENGTH: 9
<212> TYPE: PRT
<213> ORGANISM: Artificial Sequence
<220> FEATURE:
<223> OTHER INFORMATION: epitope

<400> SEQUENCE: 58

Gln Asp Thr Asn Ser Lys Lys Gln Ser
1               5

<210> SEQ ID NO 59
<211> LENGTH: 9
<212> TYPE: PRT
<213> ORGANISM: Artificial Sequence
<220> FEATURE:
<223> OTHER INFORMATION: epitope

<400> SEQUENCE: 59

Asp Thr Asn Ser Lys Lys Gln Ser Asp
1               5

<210> SEQ ID NO 60
<211> LENGTH: 9
<212> TYPE: PRT
<213> ORGANISM: Artificial Sequence
<220> FEATURE:
<223> OTHER INFORMATION: epitope

<400> SEQUENCE: 60

Thr Asn Ser Lys Lys Gln Ser Asp Thr
1               5

<210> SEQ ID NO 61
<211> LENGTH: 9
```

```
<212> TYPE: PRT
<213> ORGANISM: Artificial Sequence
<220> FEATURE:
<223> OTHER INFORMATION: epitope

<400> SEQUENCE: 61

Asn Ser Lys Lys Gln Ser Asp Thr His
1               5

<210> SEQ ID NO 62
<211> LENGTH: 9
<212> TYPE: PRT
<213> ORGANISM: Artificial Sequence
<220> FEATURE:
<223> OTHER INFORMATION: epitope

<400> SEQUENCE: 62

Ser Lys Lys Gln Ser Asp Thr His Leu
1               5

<210> SEQ ID NO 63
<211> LENGTH: 9
<212> TYPE: PRT
<213> ORGANISM: Artificial Sequence
<220> FEATURE:
<223> OTHER INFORMATION: epitope

<400> SEQUENCE: 63

Lys Lys Gln Ser Asp Thr His Leu Glu
1               5

<210> SEQ ID NO 64
<211> LENGTH: 9
<212> TYPE: PRT
<213> ORGANISM: Artificial Sequence
<220> FEATURE:
<223> OTHER INFORMATION: epitope

<400> SEQUENCE: 64

Lys Gln Ser Asp Thr His Leu Glu Glu
1               5

<210> SEQ ID NO 65
<211> LENGTH: 9
<212> TYPE: PRT
<213> ORGANISM: Artificial Sequence
<220> FEATURE:
<223> OTHER INFORMATION: epitope

<400> SEQUENCE: 65

Gln Ser Asp Thr His Leu Glu Glu Thr
1               5

<210> SEQ ID NO 66
<211> LENGTH: 10
<212> TYPE: PRT
<213> ORGANISM: Artificial Sequence
<220> FEATURE:
<223> OTHER INFORMATION: epitope

<400> SEQUENCE: 66

Arg Leu Arg Lys Gly Arg Met Met Asp Val
1               5                   10

<210> SEQ ID NO 67
<211> LENGTH: 10
<212> TYPE: PRT
```

<213> ORGANISM: Artificial Sequence
<220> FEATURE:
<223> OTHER INFORMATION: epitope

<400> SEQUENCE: 67

Leu Arg Lys Gly Arg Met Met Asp Val Lys
1               5                   10

<210> SEQ ID NO 68
<211> LENGTH: 10
<212> TYPE: PRT
<213> ORGANISM: Artificial Sequence
<220> FEATURE:
<223> OTHER INFORMATION: epitope

<400> SEQUENCE: 68

Arg Lys Gly Arg Met Met Asp Val Lys Lys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: epitope

<400> SEQUENCE: 69

Lys Gly Arg Met Met Asp Val Lys Lys Cys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: epitope

<400> SEQUENCE: 70

Gly Arg Met Met Asp Val Lys Lys Cys Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: epitope

<400> SEQUENCE: 71

Arg Met Met Asp Val Lys Lys Cys Gly Ile
1               5                   10

<210> SEQ ID NO 72
<211> LENGTH: 10
<212> TYPE: PRT
<213> ORGANISM: Artificial Sequence
<220> FEATURE:
<223> OTHER INFORMATION: epitope

<400> SEQUENCE: 72

Met Met Asp Val Lys Lys Cys Gly Ile Gln
1               5                   10

<210> SEQ ID NO 73
<211> LENGTH: 10
<212> TYPE: PRT
<213> ORGANISM: Artificial Sequence

```
<220> FEATURE:
<223> OTHER INFORMATION: epitope

<400> SEQUENCE: 73

Met Asp Val Lys Lys Cys Gly Ile Gln Asp
1               5                   10

<210> SEQ ID NO 74
<211> LENGTH: 10
<212> TYPE: PRT
<213> ORGANISM: Artificial Sequence
<220> FEATURE:
<223> OTHER INFORMATION: epitope

<400> SEQUENCE: 74

Asp Val Lys Lys Cys Gly Ile Gln Asp Thr
1               5                   10

<210> SEQ ID NO 75
<211> LENGTH: 10
<212> TYPE: PRT
<213> ORGANISM: Artificial Sequence
<220> FEATURE:
<223> OTHER INFORMATION: epitope

<400> SEQUENCE: 75

Val Lys Lys Cys Gly Ile Gln Asp Thr Asn
1               5                   10

<210> SEQ ID NO 76
<211> LENGTH: 10
<212> TYPE: PRT
<213> ORGANISM: Artificial Sequence
<220> FEATURE:
<223> OTHER INFORMATION: epitope

<400> SEQUENCE: 76

Lys Lys Cys Gly Ile Gln Asp Thr Asn Ser
1               5                   10

<210> SEQ ID NO 77
<211> LENGTH: 10
<212> TYPE: PRT
<213> ORGANISM: Artificial Sequence
<220> FEATURE:
<223> OTHER INFORMATION: epitope

<400> SEQUENCE: 77

Lys Cys Gly Ile Gln Asp Thr Asn Ser Lys
1               5                   10

<210> SEQ ID NO 78
<211> LENGTH: 10
<212> TYPE: PRT
<213> ORGANISM: Artificial Sequence
<220> FEATURE:
<223> OTHER INFORMATION: epitope

<400> SEQUENCE: 78

Cys Gly Ile Gln Asp Thr Asn Ser Lys Lys
1               5                   10

<210> SEQ ID NO 79
<211> LENGTH: 10
<212> TYPE: PRT
<213> ORGANISM: Artificial Sequence
<220> FEATURE:
```

<223> OTHER INFORMATION: epitope

<400> SEQUENCE: 79

Gly Ile Gln Asp Thr Asn Ser Lys Lys Gln
1               5                   10

<210> SEQ ID NO 80
<211> LENGTH: 10
<212> TYPE: PRT
<213> ORGANISM: Artificial Sequence
<220> FEATURE:
<223> OTHER INFORMATION: epitope

<400> SEQUENCE: 80

Ile Gln Asp Thr Asn Ser Lys Lys Gln Ser
1               5                   10

<210> SEQ ID NO 81
<211> LENGTH: 10
<212> TYPE: PRT
<213> ORGANISM: Artificial Sequence
<220> FEATURE:
<223> OTHER INFORMATION: epitope

<400> SEQUENCE: 81

Gln Asp Thr Asn Ser Lys Lys Gln Ser Asp
1               5                   10

<210> SEQ ID NO 82
<211> LENGTH: 10
<212> TYPE: PRT
<213> ORGANISM: Artificial Sequence
<220> FEATURE:
<223> OTHER INFORMATION: epitope

<400> SEQUENCE: 82

Asp Thr Asn Ser Lys Lys Gln Ser Asp Thr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: epitope

<400> SEQUENCE: 83

Thr Asn Ser Lys Lys Gln Ser Asp Thr His
1               5                   10

<210> SEQ ID NO 84
<211> LENGTH: 10
<212> TYPE: PRT
<213> ORGANISM: Artificial Sequence
<220> FEATURE:
<223> OTHER INFORMATION: epitope

<400> SEQUENCE: 84

Asn Ser Lys Lys Gln Ser Asp Thr His Leu
1               5                   10

<210> SEQ ID NO 85
<211> LENGTH: 10
<212> TYPE: PRT
<213> ORGANISM: Artificial Sequence
<220> FEATURE:
<223> OTHER INFORMATION: epitope

<400> SEQUENCE: 85

Ser Lys Lys Gln Ser Asp Thr His Leu Glu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: epitope

<400> SEQUENCE: 86

Lys Lys Gln Ser Asp Thr His Leu Glu Glu
1               5                   10

<210> SEQ ID NO 87
<211> LENGTH: 10
<212> TYPE: PRT
<213> ORGANISM: Artificial Sequence
<220> FEATURE:
<223> OTHER INFORMATION: epitope

<400> SEQUENCE: 87

Lys Gln Ser Asp Thr His Leu Glu Glu Thr
1               5                   10

<210> SEQ ID NO 88
<211> LENGTH: 11
<212> TYPE: PRT
<213> ORGANISM: Artificial Sequence
<220> FEATURE:
<223> OTHER INFORMATION: epitope

<400> SEQUENCE: 88

Arg Leu Arg Lys Gly Arg Met Met Asp Val Lys
1               5                   10

<210> SEQ ID NO 89
<211> LENGTH: 11
<212> TYPE: PRT
<213> ORGANISM: Artificial Sequence
<220> FEATURE:
<223> OTHER INFORMATION: epitope

<400> SEQUENCE: 89

Leu Arg Lys Gly Arg Met Met Asp Val Lys Lys
1               5                   10

<210> SEQ ID NO 90
<211> LENGTH: 11
<212> TYPE: PRT
<213> ORGANISM: Artificial Sequence
<220> FEATURE:
<223> OTHER INFORMATION: epitope

<400> SEQUENCE: 90

Arg Lys Gly Arg Met Met Asp Val Lys Lys Cys
1               5                   10

<210> SEQ ID NO 91
<211> LENGTH: 11
<212> TYPE: PRT
<213> ORGANISM: Artificial Sequence
<220> FEATURE:
<223> OTHER INFORMATION: epitope

```
<400> SEQUENCE: 91

Lys Gly Arg Met Met Asp Val Lys Lys Cys Gly
1               5                   10

<210> SEQ ID NO 92
<211> LENGTH: 11
<212> TYPE: PRT
<213> ORGANISM: Artificial Sequence
<220> FEATURE:
<223> OTHER INFORMATION: epitope

<400> SEQUENCE: 92

Gly Arg Met Met Asp Val Lys Lys Cys Gly Ile
1               5                   10

<210> SEQ ID NO 93
<211> LENGTH: 11
<212> TYPE: PRT
<213> ORGANISM: Artificial Sequence
<220> FEATURE:
<223> OTHER INFORMATION: epitope

<400> SEQUENCE: 93

Arg Met Met Asp Val Lys Lys Cys Gly Ile Gln
1               5                   10

<210> SEQ ID NO 94
<211> LENGTH: 11
<212> TYPE: PRT
<213> ORGANISM: Artificial Sequence
<220> FEATURE:
<223> OTHER INFORMATION: epitope

<400> SEQUENCE: 94

Met Met Asp Val Lys Lys Cys Gly Ile Gln Asp
1               5                   10

<210> SEQ ID NO 95
<211> LENGTH: 11
<212> TYPE: PRT
<213> ORGANISM: Artificial Sequence
<220> FEATURE:
<223> OTHER INFORMATION: epitope

<400> SEQUENCE: 95

Met Asp Val Lys Lys Cys Gly Ile Gln Asp Thr
1               5                   10

<210> SEQ ID NO 96
<211> LENGTH: 11
<212> TYPE: PRT
<213> ORGANISM: Artificial Sequence
<220> FEATURE:
<223> OTHER INFORMATION: epitope

<400> SEQUENCE: 96

Asp Val Lys Lys Cys Gly Ile Gln Asp Thr Asn
1               5                   10

<210> SEQ ID NO 97
<211> LENGTH: 11
<212> TYPE: PRT
<213> ORGANISM: Artificial Sequence
<220> FEATURE:
<223> OTHER INFORMATION: epitope

<400> SEQUENCE: 97
```

```
Val Lys Lys Cys Gly Ile Gln Asp Thr Asn Ser
1               5                   10

<210> SEQ ID NO 98
<211> LENGTH: 11
<212> TYPE: PRT
<213> ORGANISM: Artificial Sequence
<220> FEATURE:
<223> OTHER INFORMATION: epitope

<400> SEQUENCE: 98

Lys Lys Cys Gly Ile Gln Asp Thr Asn Ser Lys
1               5                   10

<210> SEQ ID NO 99
<211> LENGTH: 11
<212> TYPE: PRT
<213> ORGANISM: Artificial Sequence
<220> FEATURE:
<223> OTHER INFORMATION: epitope

<400> SEQUENCE: 99

Lys Cys Gly Ile Gln Asp Thr Asn Ser Lys Lys
1               5                   10

<210> SEQ ID NO 100
<211> LENGTH: 11
<212> TYPE: PRT
<213> ORGANISM: Artificial Sequence
<220> FEATURE:
<223> OTHER INFORMATION: epitope

<400> SEQUENCE: 100

Cys Gly Ile Gln Asp Thr Asn Ser Lys Lys Gln
1               5                   10

<210> SEQ ID NO 101
<211> LENGTH: 11
<212> TYPE: PRT
<213> ORGANISM: Artificial Sequence
<220> FEATURE:
<223> OTHER INFORMATION: epitope

<400> SEQUENCE: 101

Gly Ile Gln Asp Thr Asn Ser Lys Lys Gln Ser
1               5                   10

<210> SEQ ID NO 102
<211> LENGTH: 11
<212> TYPE: PRT
<213> ORGANISM: Artificial Sequence
<220> FEATURE:
<223> OTHER INFORMATION: epitope

<400> SEQUENCE: 102

Ile Gln Asp Thr Asn Ser Lys Lys Gln Ser Asp
1               5                   10

<210> SEQ ID NO 103
<211> LENGTH: 11
<212> TYPE: PRT
<213> ORGANISM: Artificial Sequence
<220> FEATURE:
<223> OTHER INFORMATION: epitope

<400> SEQUENCE: 103
```

Gln Asp Thr Asn Ser Lys Lys Gln Ser Asp Thr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: epitope

<400> SEQUENCE: 104

Asp Thr Asn Ser Lys Lys Gln Ser Asp Thr His
1               5                   10

<210> SEQ ID NO 105
<211> LENGTH: 11
<212> TYPE: PRT
<213> ORGANISM: Artificial Sequence
<220> FEATURE:
<223> OTHER INFORMATION: epitope

<400> SEQUENCE: 105

Thr Asn Ser Lys Lys Gln Ser Asp Thr His Leu
1               5                   10

<210> SEQ ID NO 106
<211> LENGTH: 11
<212> TYPE: PRT
<213> ORGANISM: Artificial Sequence
<220> FEATURE:
<223> OTHER INFORMATION: epitope

<400> SEQUENCE: 106

Asn Ser Lys Lys Gln Ser Asp Thr His Leu Glu
1               5                   10

<210> SEQ ID NO 107
<211> LENGTH: 11
<212> TYPE: PRT
<213> ORGANISM: Artificial Sequence
<220> FEATURE:
<223> OTHER INFORMATION: epitope

<400> SEQUENCE: 107

Ser Lys Lys Gln Ser Asp Thr His Leu Glu Glu
1               5                   10

<210> SEQ ID NO 108
<211> LENGTH: 11
<212> TYPE: PRT
<213> ORGANISM: Artificial Sequence
<220> FEATURE:
<223> OTHER INFORMATION: epitope

<400> SEQUENCE: 108

Lys Lys Gln Ser Asp Thr His Leu Glu Glu Thr
1               5                   10

<210> SEQ ID NO 109
<211> LENGTH: 23
<212> TYPE: RNA
<213> ORGANISM: Artificial Sequence
<220> FEATURE:
<223> OTHER INFORMATION: IRES

<400> SEQUENCE: 109
augauaauau ggccacaacc aug                                           23

<210> SEQ ID NO 110
<211> LENGTH: 114
<212> TYPE: PRT
<213> ORGANISM: Artificial Sequence
<220> FEATURE:
<223> OTHER INFORMATION: heavy chain variable region

<400> SEQUENCE: 110

Glu Gln Leu Val Glu Ser Gly Gly Leu Val Thr Pro Gly Gly Ser
1               5                   10                  15

Leu Thr Leu Thr Cys Thr Val Ser Thr Ile Asp Leu Ser Thr Phe Ala
                20                  25                  30

Ile Ser Trp Val Arg Gln Ala Pro Gly Lys Gly Leu Glu Trp Ile Gly
            35                  40                  45

Thr Ile Asn Thr Asp Leu Thr Thr Tyr Tyr Val Asn Trp Ala Lys Gly
        50                  55                  60

Arg Phe Thr Ile Ser Lys Thr Ser Ser Thr Val Asp Leu Lys Met
65                  70                  75                  80

Thr Gly Leu Thr Ile Glu Asp Thr Ala Thr Tyr Phe Cys Ala Arg Lys
                85                  90                  95

Leu Phe Gly Asn Gly Asn Val Trp Gly Pro Gly Thr Leu Val Thr Val
            100                 105                 110

Ser Ser

<210> SEQ ID NO 111
<211> LENGTH: 110
<212> TYPE: PRT
<213> ORGANISM: Artificial Sequence
<220> FEATURE:
<223> OTHER INFORMATION: light chain variable region

<400> SEQUENCE: 111

Ala Gln Val Leu Thr Gln Thr Pro Ser Pro Val Ser Ala Ser Val Gly
1               5                   10                  15

Ser Thr Val Thr Ile Asn Cys Gln Ala Ser Gln Ser Leu His Arg Asn
                20                  25                  30

Asn Tyr Leu Ser Trp Phe Gln Gln Lys Pro Gly Gln Pro Pro Lys Gln
            35                  40                  45

Leu Ile Tyr Gln Ala Ser Thr Leu Ala Ser Gly Val Ser Ser Arg Phe
        50                  55                  60

Ser Gly Ser Gly Ser Gly Thr Gln Phe Thr Leu Thr Ile Ser Asp Val
65                  70                  75                  80

Val Cys Asp Asp Ala Ala Thr Tyr Tyr Cys Leu Gly Gly Val Ser Gly
                85                  90                  95

Gly Pro Tyr Pro Phe Gly Gly Gly Thr Glu Val Val Val Lys
            100                 105                 110

<210> SEQ ID NO 112
<211> LENGTH: 23
<212> TYPE: PRT
<213> ORGANISM: Artificial Sequence
<220> FEATURE:
<223> OTHER INFORMATION: light chain signal sequence

<400> SEQUENCE: 112

Met Asp Thr Arg Ala Pro Thr Gln Leu Leu Gly Leu Leu Leu Leu Trp
1               5                   10                  15

Leu Pro Gly Ala Thr Val Ala

<210> SEQ ID NO 113
<211> LENGTH: 19
<212> TYPE: PRT
<213> ORGANISM: Artificial Sequence
<220> FEATURE:
<223> OTHER INFORMATION: heavy chain signal sequence

<400> SEQUENCE: 113

Met Glu Thr Gly Leu Arg Trp Leu Leu Leu Val Ala Val Leu Lys Gly
1               5                   10                  15

Val Gln Cys

<210> SEQ ID NO 114
<211> LENGTH: 213
<212> TYPE: PRT
<213> ORGANISM: Artificial Sequence
<220> FEATURE:
<223> OTHER INFORMATION: MKP1A07310 light chain sequence with signal
      sequence removed

<400> SEQUENCE: 114

Gln Val Leu Thr Gln Thr Pro Ser Pro Val Ser Ala Val Gly Ser
1               5                   10                  15

Thr Val Thr Ile Asn Cys Gln Ala Ser Gln Ser Leu His Arg Asn Asn
            20                  25                  30

Tyr Leu Ser Trp Phe Gln Gln Lys Pro Gly Gln Pro Pro Lys Gln Leu
        35                  40                  45

Ile Tyr Gln Ala Ser Thr Leu Ala Ser Gly Val Ser Ser Arg Phe Ser
    50                  55                  60

Gly Ser Gly Ser Gly Thr Gln Phe Thr Leu Thr Ile Ser Asp Val Val
65                  70                  75                  80

Cys Asp Asp Ala Ala Thr Tyr Tyr Cys Leu Gly Gly Val Ser Gly Gly
                85                  90                  95

Pro Tyr Pro Phe Gly Gly Gly Thr Glu Val Val Val Lys Gly Asp Pro
            100                 105                 110

Val Ala Pro Thr Val Leu Ile Phe Pro Pro Ala Ala Asp Gln Val Ala
        115                 120                 125

Thr Gly Thr Val Thr Ile Val Cys Val Ala Asn Lys Tyr Phe Pro Asp
    130                 135                 140

Val Thr Val Thr Trp Glu Val Asp Gly Thr Thr Gln Thr Thr Gly Ile
145                 150                 155                 160

Glu Asn Ser Lys Thr Pro Gln Asn Ser Ala Asp Cys Thr Tyr Asn Leu
                165                 170                 175

Ser Ser Thr Leu Thr Leu Thr Ser Thr Gln Tyr Asn Ser His Lys Glu
            180                 185                 190

Tyr Thr Cys Lys Val Thr Gln Gly Thr Thr Ser Val Val Gln Ser Phe
        195                 200                 205

Asn Arg Gly Asp Cys
    210

<210> SEQ ID NO 115
<211> LENGTH: 438
<212> TYPE: PRT
<213> ORGANISM: Artificial Sequence
<220> FEATURE:
<223> OTHER INFORMATION: MKP1A07310 heavy chain sequence with signal
      peptide removed

<400> SEQUENCE: 115

```
Gln Glu Gln Leu Val Glu Ser Gly Gly Leu Val Thr Pro Gly Gly
1               5                   10                  15

Ser Leu Thr Leu Thr Cys Thr Val Ser Thr Ile Asp Leu Ser Thr Phe
            20                  25                  30

Ala Ile Ser Trp Val Arg Gln Ala Pro Gly Lys Gly Leu Glu Trp Ile
            35                  40                  45

Gly Thr Ile Asn Thr Asp Leu Thr Thr Tyr Tyr Val Asn Trp Ala Lys
50                  55                  60

Gly Arg Phe Thr Ile Ser Lys Thr Ser Ser Thr Thr Val Asp Leu Lys
65                  70                  75                  80

Met Thr Gly Leu Thr Ile Glu Asp Thr Ala Thr Tyr Phe Cys Ala Arg
                85                  90                  95

Lys Leu Phe Gly Asn Gly Asn Val Trp Gly Pro Gly Thr Leu Val Thr
            100                 105                 110

Val Ser Ser Gly Gln Pro Lys Ala Pro Ser Val Phe Pro Leu Ala Pro
            115                 120                 125

Cys Cys Gly Asp Thr Pro Ser Ser Thr Val Thr Leu Gly Cys Leu Val
            130                 135                 140

Lys Gly Tyr Leu Pro Glu Pro Val Thr Val Thr Trp Asn Ser Gly Thr
145                 150                 155                 160

Leu Thr Asn Gly Val Arg Thr Phe Pro Ser Val Arg Gln Ser Ser Gly
                165                 170                 175

Leu Tyr Ser Leu Ser Ser Val Val Ser Val Thr Ser Ser Ser Gln Pro
            180                 185                 190

Val Thr Cys Asn Val Ala His Pro Ala Thr Asn Thr Lys Val Asp Lys
            195                 200                 205

Thr Val Ala Pro Ser Thr Cys Ser Lys Pro Thr Cys Pro Pro Pro Glu
            210                 215                 220

Leu Leu Gly Gly Pro Ser Val Phe Ile Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser Gln Asp Asp Pro Glu Val Gln Phe Thr Trp Tyr Ile Asn Asn
            260                 265                 270

Glu Gln Val Arg Thr Ala Arg Pro Pro Leu Arg Glu Gln Gln Phe Asn
            275                 280                 285

Ser Thr Ile Arg Val Val Ser Thr Leu Pro Ile Ala His Gln Asp Trp
            290                 295                 300

Leu Arg Gly Lys Glu Phe Lys Cys Lys Val His Asn Lys Ala Leu Pro
305                 310                 315                 320

Ala Pro Ile Glu Lys Thr Ile Ser Lys Ala Arg Gly Gln Pro Leu Glu
                325                 330                 335

Pro Lys Val Tyr Thr Met Gly Pro Pro Arg Glu Glu Leu Ser Ser Arg
            340                 345                 350

Ser Val Ser Leu Thr Cys Met Ile Asn Gly Phe Tyr Pro Ser Asp Ile
            355                 360                 365

Ser Val Glu Trp Glu Lys Asn Gly Lys Ala Glu Asp Asn Tyr Lys Thr
            370                 375                 380

Thr Pro Ala Val Leu Asp Ser Asp Gly Ser Tyr Phe Leu Tyr Ser Lys
385                 390                 395                 400

Leu Ser Val Pro Thr Ser Glu Trp Gln Arg Gly Asp Val Phe Thr Cys
                405                 410                 415
```

```
Ser Val Met His Glu Ala Leu His Asn His Tyr Thr Gln Lys Ser Ile
            420                 425                 430

Ser Arg Ser Pro Gly Lys
        435

<210> SEQ ID NO 116
<211> LENGTH: 10
<212> TYPE: PRT
<213> ORGANISM: Artificial Sequence
<220> FEATURE:
<223> OTHER INFORMATION: MKP1A-7310 Light chain FR4

<400> SEQUENCE: 116

Phe Gly Gly Gly Thr Glu Val Val Val Lys
1               5                   10

<210> SEQ ID NO 117
<211> LENGTH: 11
<212> TYPE: PRT
<213> ORGANISM: Artificial Sequence
<220> FEATURE:
<223> OTHER INFORMATION: MKP1A-7310 heavy chain FR4

<400> SEQUENCE: 117

Trp Gly Pro Gly Thr Leu Val Thr Val Ser Ser
1               5                   10
```

DIAGNOSTIC ANTI-PD-L1 ANTIBODY AND USE THEREOF

CROSS REFERENCE TO RELATED APPLICATIONS

This application is a U.S. National Stage Application of International Application No. PCT/EP2017/073712, filed on Sep. 20, 2017, published as WO 2018/054940 on Mar. 29, 2018, which claims the benefit of European Patent Application No. 16189804.4, filed Sep. 20, 2016, the contents of each of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "P34717_Sequence_listing_ST25.txt" created on Mar. 19, 2019, and having a size of 40,960 bytes. The sequence listing contained in this .txt file is part of the specification and is herein incorporated by reference in its entirety.

FIELD OF THE INVENTION

The present invention pertains to the field of cancer diagnostics, in particular to the use of a diagnostic antibody to detect the presence of a PD-L1 epitope in a tumor sample for in vitro diagnosis.

BACKGROUND

Programmed cell death 1 ligand 1 (PD-L1) also known as cluster of differentiation (CD274) or B7 homolog 1 (B7-H1) is a protein that in humans is encoded by the CD274 gene and is, next to PD-L2 (CD273), one of the ligands of PD-1 (CD279). PD-L1 is a 40 kDa type 1 transmembrane protein which is expressed on many hematopoietic cells, including dendritic cells, macrophages, mesenchymal stem cells and bone marrow-derived mast cells. PD-L1 is found to be inducibly expressed on epithelial and endothelial cells through the action of interferons. Sites of immune privilege such as syncytiotrophoblats in the placenta and in the retina were found to constitutively express PD-L1.

Expression of PD-L1 in the placenta increases at the beginning of the second trimester, is upregulated by increased oxygen and is rapidly lost with low oxygen concentrations. Experiments have shown that the PD-1-PD-L pathway regulates the balance between the stimulatory and inhibitory signals needed for effective immune responses to microbes and maintenance of self-tolerance, respectively. Many microorganisms that cause chronic infection exploit the PD-1-PD-L1 pathway to evade host immune effector mechanisms. Based on a mouse model of liver infection, the PD-PD-L1 pathway is also thought to regulate immune-mediated tissue damage during viral infection, since PD-1 null mice show increased liver damage upon clearance of adenovirus compared to wild type mice, which is thought to be caused by highly active and aggressive T-cells.

Immune attack via IFNγ release leads to inducible upregulation of PD-L1 by mucosa creating an "immune shield" to protect against autoimmune attack in the setting of chronic inflammation or infection. Upregulated PD-L1 on these cells binds to PD-1 on T-cells contributing to the development of T-cell exhaustion.

Tumor cells have co-opted this PD-1-PD-L1 regulatory mechanism, which under normal physiological setting protects mucosa from autoimmune attack, and instead overexpress PD-L1 to avoid immunologic surveillance thereby promoting cancer growth.

This immunosuppressive mechanism can be hijacked by PD-L1 positive tumor cells eventually leading to the escape of tumors from the elimination by the immune system. Inhibiting the PD-1/PD-L1 interaction by means of a monoclonal antibody provides a promising concept for the treatment of tumors with PD-L1 expression. Clinical trials of blocking monoclonal antibodies against PD-1 and PD-L1 are currently ongoing for patients suffering from various malignancies.

Statistical analysis of published anti-PD-L1 clinical trial data comparing the clinical response rate of PD-L1 positive or PD-L1 negative patients indicates that PD-L1 expression is a predictive marker of clinical response for certain cancer types and a correlation biomarker for others (Gandini et al., Crit Rev Oncol Hematol. 2016 April; 100:88-98). In metastatic melanoma, for example, PD-L1 expression in tumor tissue is associated with a significant better prognosis, as PD-L1 positive patients receiving anti-PD-L1 therapy show a 53% reduction in mortality.

Studies have also shown that across multiple cancer types responses to anti-PD-L1 therapy were observed in patients with tumors expressing high levels of PD-L1, in particular when PD-L1 was expressed on tumor-infiltrating immune cells (see e.g. Herbst et al., Nature. 2014 Nov. 27; 515 (7528):563-7; Ilie et al., Annals of Oncology 27: 147-153, 2016). In papillary thyroid cancer PD-L1 expression was found to correlate with recurrence and shortened disease free survival supporting the use of PD-L1 expression in this tumor type as a prognostic marker (Chowdhury et al., Oncotarget. 2016 Apr. 12).

Detection and scoring of PD-L1 expression in tumor tissue samples is usually done by means of immunohistochemistry on frozen or formalin-fixed, paraffin-embedded (FFPE) tumor tissue sections. Scoring of PD-L1 expression can done using different methodologies: One approach for example employed a binary end-point scoring of a specimen of being positive or negative for PD-L1 expression, with a positive result defined in terms of the percentage of tumor cells that exhibited histologic evidence of cell-surface membrane staining. Two different cut-off values of 1% and 5% of total tumor cells have been used at which a tumor specimen was scored as PD-L1 positive (Cancer. 2011 May 15; 117(10):2192-201; N Engl J Med 2012; 366:2443-54). PD-L1 expression in tumor specimens has also been quantified by scoring both, tumor cells and tumor-infiltrating immune cells that display a membranous staining, compared to tumor cells which showed both, membranous and a prominent cytoplasmic staining. Specimen scoring based on PD-L1 expression was subsequently done, whereby IHC scores of 0, 1, 2, or 3 were given. A specimen was scored with "0" if less than 1% of the cells were PD-L1 positive, "1" for more than 1%, but less than 5%, "2" if more than 5%, but less than 10%, or "3" if more than 10% of the cells were PD-L1 positive (Herbst et al. Nature. 2014 Nov. 27; 515 (7528):563-7). PD-L1 expression in tumor-infiltrating mononuclear cells (TIMCs) has been assessed using a semi-quantitative approach according to three categories with respective scores of 0, 1, or 2 depending on the number of TIMCs in the specimen: 0%=0, <5%=1, ≥5%=2.

The specificity and reproducibility of most commercially available anti-PD-L1 antibodies has not been thoroughly assessed and limitations of some widely used antibodies have been reported (see e.g. Cancer 2011; 117: 2192-201; Carvajal-Hausorf et al., Laboratory Investigation (2015) 95, 385-396). For example, WO 2014/165422 A1, WO 2016/007235 A1 disclose an anti-PD-L1 antibodies and scoring guidelines for use with the respective antibody to assess PD-L1 expression.

There is thus a continued need to expand the repertoire in available anti-PD-L1 antibodies that are highly specific for PD-L1 and that yield reproducible results to aid in the stratification of tumor patients amenable for an anti-PD-L1-based therapy.

SUMMARY OF THE INVENTION

The present inventors have surprisingly found that an antibody or antigen-binding fragments thereof directed against an epitope comprised in the amino acid sequence according to SEQ ID NO:1 binds to human PD-L1 with high specificity and reproducibility.

In a first embodiment the present invention provides an antibody or antigen binding fragments thereof that binds to an epitope comprised in the amino acid sequence according to SEQ ID NO: 1 with high specificity and yields reproducible results, whereby the antibody or antigen-binding fragment thereof comprises at least three amino acid sequences of SEQ ID NO:3, SEQ ID NO: 4, SEQ ID NO: 5, SEQ ID NO: 6, SEQ ID NO: 7, SEQ ID NO: 8 in its light chain sequence at least three amino acid sequences of SEQ ID NO:9, SEQ ID NO: 10, SEQ ID NO: 11, SEQ ID NO: 12, SEQ ID NO: 13, SEQ ID NO: 14 in their heavy chain sequence.

The inventive antibody or antigen-binding fragment thereof may according to one embodiment be a Fab fragment.

According to one embodiment the inventive antigen-binding fragment is a F(ab')2 fragment.

According to one embodiment the inventive antigen-binding fragment is a Fab' fragment.

In one embodiment the inventive antibody is a scFv.

According to one embodiment the inventive antibody is a di-scFv.

According to one embodiment the inventive antibody is a monoclonal antibody.

According to one embodiment the inventive antibody is an IgG type antibody.

According to one embodiment the inventive antibody light chain or antigen binding fragment thereof comprises all of SEQ ID NO:3, SEQ ID NO: 4, SEQ ID NO: 5, SEQ ID NO: 6, SEQ ID NO: 7, SEQ ID NO: 8.

According to one embodiment the heavy chain of the inventive antibody or antigen binding fragment thereof comprises all of SEQ ID NO:9, SEQ ID NO: 10, SEQ ID NO: 11, SEQ ID NO: 12, SEQ ID NO: 13, SEQ ID NO: 14.

In one embodiment the inventive antibody comprises a heavy chain or antigen-binding fragment thereof comprising the amino acid sequence according to SEQ ID NO: 110 and a light chain or antigen-binding fragment thereof comprising the amino acid sequence according to SEQ ID NO: 111.

According to a preferred embodiment the light chain of the inventive antibody comprises the amino acid sequence according to SEQ ID NO: 15 and the heavy chain comprises the amino acid sequence according to SEQ ID NO: 16.

In a preferred embodiment the inventive antibody light chain comprises the amino acid sequence according to SEQ ID NO: 114 and the antibody heavy chain comprises the amino acid sequence according to SEQ ID NO: 115.

In a preferred embodiment the inventive antibody is a rabbit antibody, or a rabbit-derived antibody.

According to one embodiment the inventive antibody or antigen-binding fragment thereof as disclosed above is further coupled to a detectable label.

According to one embodiment the detectable label of the inventive antibody or antigen-binding fragment thereof is one of an enzyme, or fluorophore, or enzyme substrate.

According to one embodiment the inventive antibody or antigen-binding fragment thereof as disclosed above is for use in detecting the presence or expression of an epitope comprised in SEQ ID NO: 1 in a sample, which according to one embodiment is a biological sample, preferably, a tissue sample, fixed tissue sample, or a formaldehyde-fixed paraffin-embedded (FFPE) tissue, more preferably, a tumor-derived formaldehyde-fixed paraffin-embedded (FFPE) tissue.

In one embodiment the detection of the presence or absence of an epitope comprised in SEQ ID NO: 1 as disclosed above is done by means of flow cytometry, ELISA, or Western blotting using the inventive antibody or antigen-binding fragment thereof as disclosed above.

According to a preferred embodiment the detection of the presence or expression of an epitope comprised in SEQ ID NO: 1 using the inventive antibody or antigen-binding fragment thereof as disclosed above is done by means of immunohistochemistry (IHC).

In one embodiment the present invention provides for a method of detecting the presence or expression of human PD-L1 or any fragment thereof in a sample which comprises the amino acid sequence according to SEQ ID NO: 1 whereby the inventive method comprises the step of contacting the sample with the inventive antibody or antigen-binding fragment thereof and detecting the presence of bound antibody or antigen binding fragment thereof.

In one embodiment the inventive in vitro method as disclosed above is used on a biological sample, tissue sample, a fixed tissue sample, preferably a formaldehyde-fixed paraffin-embedded (FFPE) tissue sample, more preferably a formaldehyde-fixed paraffin-embedded (FFPE) tumor tissue sample.

According to one embodiment the sample used in the inventive in vitro method as disclosed above is derived from a subject having, or at risk of cancer, T-cell dysfunction, acute or chronic infection or tumor immunity.

In one embodiment the present invention pertains to the use of the inventive antibody or antigen-binding fragment as disclosed above in the presence or expression of an epitope comprised in SEQ ID NO: 1 in a sample.

In one embodiment the present invention provides an isolated polynucleotide encoding the inventive antibody or antigen binding fragment thereof as disclosed above.

According to one embodiment the present invention provides an expression vector which comprises the polynucleotide encoding the inventive antibody or antigen-binding fragment thereof.

In one embodiment the present invention provides for an expression vector as disclosed above for use in producing the inventive antibody.

In one embodiment the present invention provides at least one host cell comprising at least one expression vector according to the invention.

In one embodiment the present invention provides at least one host cell according to the invention for use in the manufacture the inventive antibody.

According to one embodiment the present invention provides a method of treating cancer in patient which comprises the steps of detecting the presence or expression of human PD-L1 in a sample from said patient using the inventive anti-PD-L1 antibody as disclosed above, comparing the PD-L1 expression in the patient sample to a reference sample and administration of an immune checkpoint inhibitor (e.g. an anti-PD-L1 or anti-PD-1 antibody) to the patient if the PD-L1 expression in the patient sample is increased compared to the reference sample.

BRIEF DESCRIPTION OF DRAWINGS

FIG. 1: ELISA results for inventive antibody clone MKP1A07310 using 50 µl/well of immunogen at a concentration of 1 µg/ml for coating of the wells of the ELISA plate.

FIG. 3: Immunohistochemical staining using the inventive antibody (MKP1A07310) and a different anti-PD-L1 antibody directed against an extracellular epitope of human PD-L1 in a siRNA knockdown on MDA-MB 231 cells. PD-L1 staining was reduced in the siRNA knockdown cells.

FIG. 7: (A) IHC detection of PD-L1 positive cells using the inventive antibody with DAB as chromogen (right image); detection of chromogen by computer software (middle image); detection of blue staining of nuclei and cytoplasm (right image). Arrows indicate positive cells. (B) IHC staining on positive and negative control tissues using the inventive antibody MKP1A07310 at a concentration of 1 µg/ml.

SEQUENCE LISTING

SEQ ID NO: 1  RLRKGRMMDVKKCGIQDTNSKKQSDTHLEET

SEQ ID NO: 2  CGIQDTNSKKQSDTH

SEQ ID NO: 3  AQVLTQTPSPVSASVGSTVTINCQAS

-continued

Figure 2:
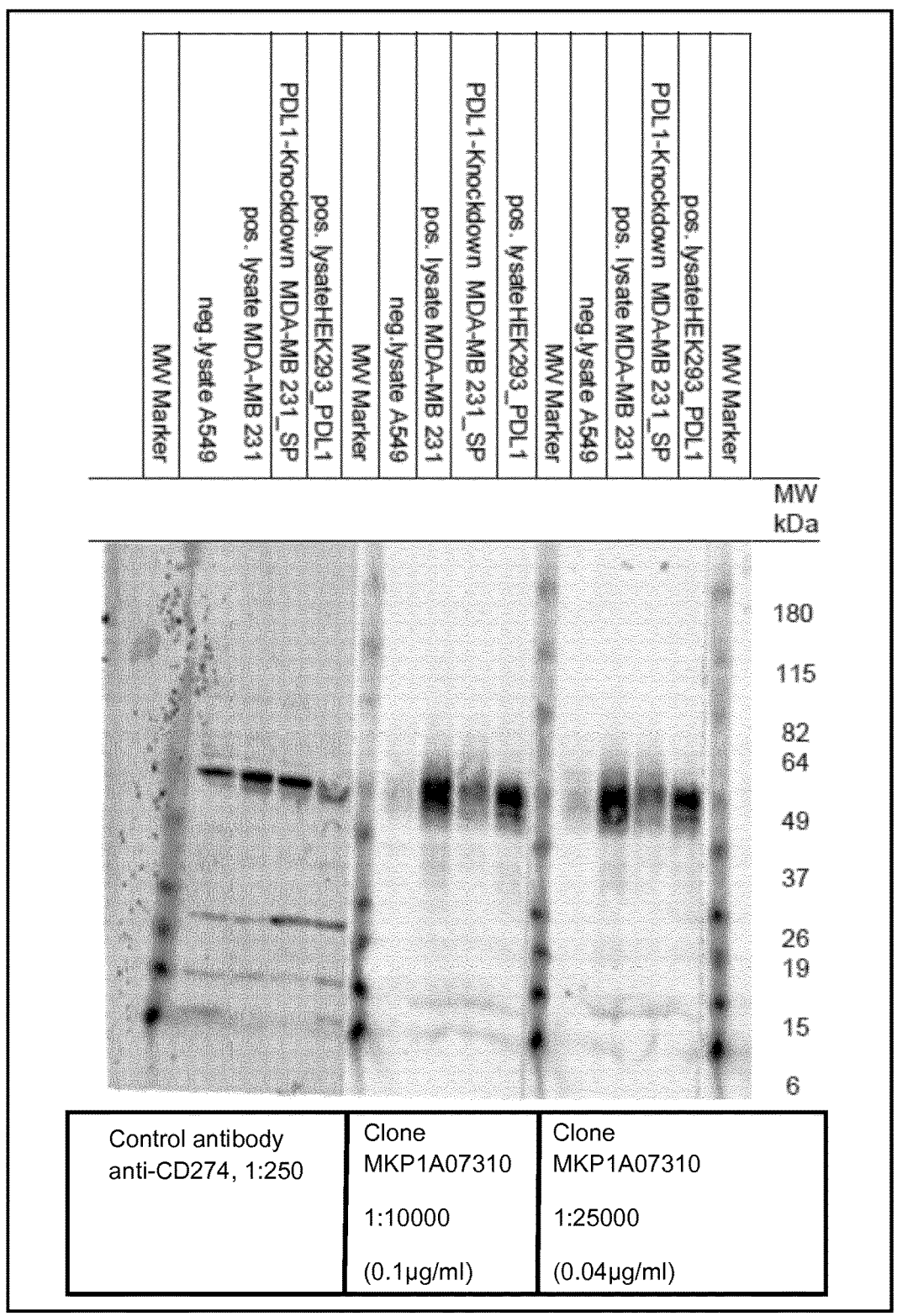
FIG. 2: Western Blot using the inventive antibody clone MKP1A07310 at dilutions of 1:10000 and 1:25000 and a control antibody (anti-CD247, dilution 1:250) using the cell lysates indicated. Western blotting was done using cell lysates of PD-L1 transfected HEK293, PD-L1 expressing MDA-MB 231, siRNA PDL1 knockdowns of MDA-MB 231 and the PD-L1 low cell line A549.
Figure 4:
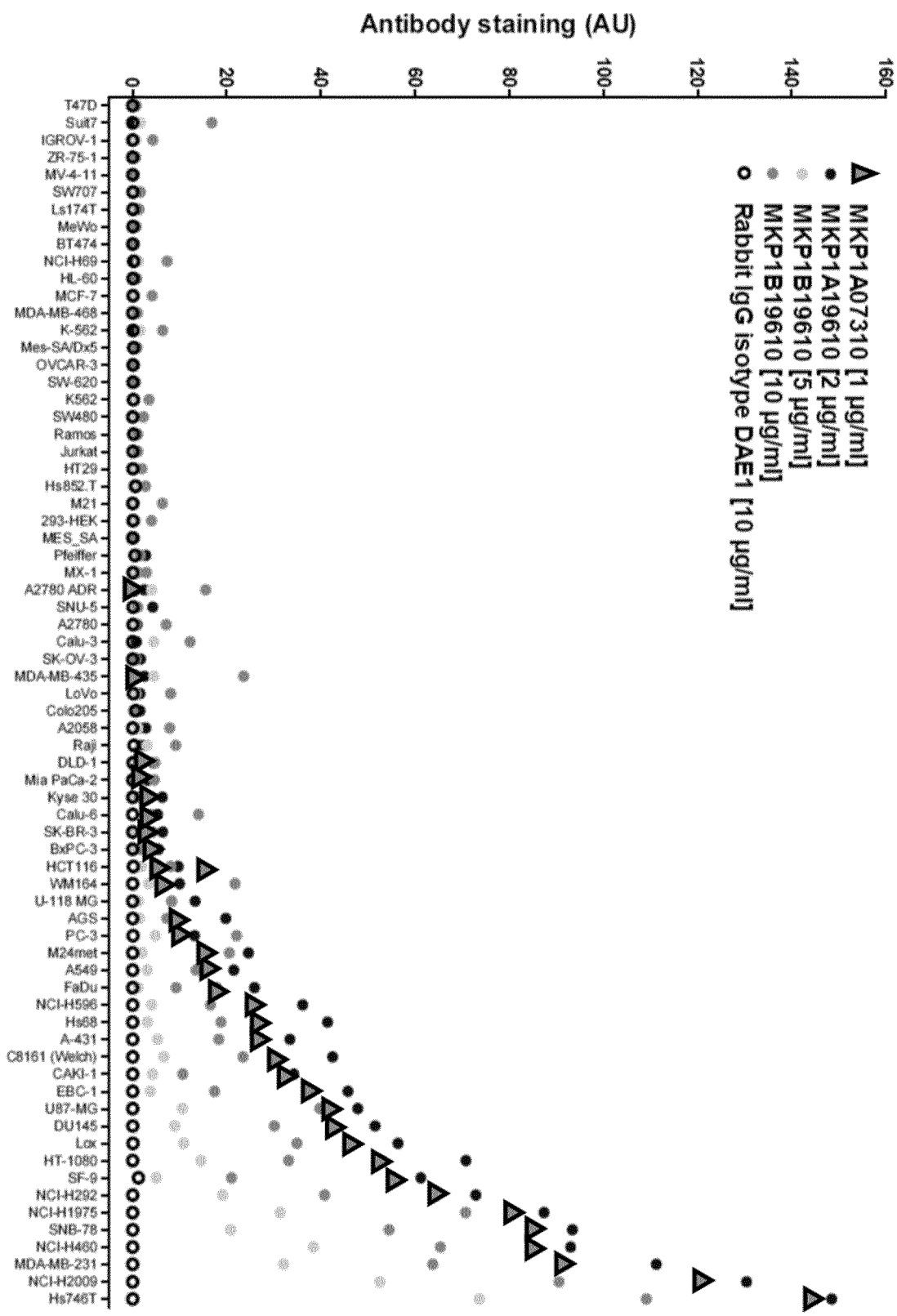
FIG. 4: The inventive antibody (MKP1A07310) as well as one antibody directed against an extracellular epitope of human PD-L1 (MKP1B19610) were characterized using MKP1A7310 in a concentration of 1 µg/ml, and MKP1B19610 at three different concentrations (2 µg/ml, 5 µg/ml and 10 µg/ml) on a cancer cell line array out of 70 cell lines to assess and compare their respective binding characteristics and to determine the optimum working concentration for further studies. The cancer cell line array (CAX09_70_MB, manufactured by Multiblock GmbH and Zytomed Systems GmbH) was used for the assessment of antibody properties in IHC. The cancer cell lines that were used for the manufacture of the custom cancer cell line array were fixed in phosphate buffered 4% paraformaldehyde, pH 7 over 16 to 48 hours at room temperature and subsequently embedded in paraffin.

| SEQUENCE LISTING | |
|---|---|
| SEQ ID NO: 4 | QSLHRNNY |
| SEQ ID NO: 5 | LSWFQQKPGQPPKQLIY |
| SEQ ID NO: 6 | QAS |
| SEQ ID NO: 7 | TLASGVSSRFSGSGSGTQFTLTISDVVCDDAATYYC |
| SEQ ID NO: 8 | LGGVSGGPYP |
| SEQ ID NO: 9 | EQLVESGGGLVTPGGSLTLTCTVS |
| SEQ ID NO: 10 | TIDLSTFA |
| SEQ ID NO: 11 | ISWVRQAPGKGLEWIGT |
| SEQ ID NO: 12 | INTDLTT |
| SEQ ID NO: 13 | YYVNWAKGRFTISKTSSTTVDLKMTGLTIEDTATYFC |
| SEQ ID NO: 14 | ARKLFGNGNV |
| SEQ ID NO: 15 | MDTRAPTQLLGLLLLWLPGATVAQVLTQTPSPVSASVGSTVTINC<br>QASQSLHRNNYLSWFQQKPGQPPKQLIYQASTLASGVSSRFSGSG<br>SGTQFTLTISDVVCDDAATYYCLGGVSGGPYPFGGGTEVVVKGDP<br>VAPTVLIFPPAADQVATGTVTIVCVANKYFPDVTVTWEVDGTTQT<br>TGIENSKTPQNSADCTYNLSSTLTLTSTQYNSHKEYTCKVTQGTT<br>SVVQSFNRGDC |
| SEQ ID NO: 16 | METGLRWLLLVAVLKGVQCQEQLVESGGGLVTPGGSLTLTCTVST<br>IDLSTFAISWVRQAPGKGLEWIGTINTDLTTYYVNWAKGRFTISK<br>TSSTTVDLKMTGLTIEDTATYFCARKLFGNGNVWGPGTLVTVSSG<br>QPKAPSVFPLAPCCGDTPSSTVTLGCLVKGYLPEPVTVTWNSGTL<br>TNGVRTFPSVRQSSGLYSLSSVVSVTSSSQPVTCNVAHPATNTKV<br>DKTVAPSTCSKPTCPPPELLGGPSVFIFPPKPKDTLMISRTPEVT<br>CVVVDVSQDDPEVQFTWYINNEQVRTARPPLREQQFNSTIRVVST<br>LPIAHQDWLRGKEFKCKVHNKALPAPIEKTISKARGQPLEPKVYT<br>MGPPREELSSRVSLTCMINGFYPSDISVEWEKNGKAEDNYKTTP<br>AVLDSDGSYFLYSKLSVPTSEWQRGDVFTCSVMHEALHNHYTQKS<br>ISRSPGK |
| SEQ ID NO: 17 | 5'-atggacacga gggcccccac tcagctgctg<br>gggctcctgc tgctctggct cccaggtgcc acagttgccc<br>aagtgctgac ccagacccca tcccccgtgt ctgcatctgt<br>gggaagcaca gtcaccatca attgccaggc cagtcagagt<br>cttcatcgca acaactactt atcctggttt cagcagaaac<br>cagggcagcc tcccaagcaa ctgatctatc aggcatccac<br>tctggcatct ggggtctcat cgcggttcag tggcagtgga<br>tctgggacac agttcactct caccatcagc gatgtggtgt<br>gtgacgatgc tgccacttac tactgtctgg gcggtgttag<br>tggtggtcct tatcctttcg gcggagggac cgaggtggtc<br>gtcaaaggtg atccagttgc acctactgtc ctcatcttcc<br>caccagctgc tgatcaggtg gcaactggaa cagtcaccat<br>cgtgtgtgtg gcgaataaat actttcccga tgtcaccgtc<br>acctgggagg tggatggcac cacccaaaca actggcatcg<br>agaacagtaa aacaccgcag aattctgcag attgtaccta<br>caacctcagc agcactctga cactgaccag cacacagtac<br>aacagccaca agagtacac ctgcaaggtg acccagggca<br>cgacctcagt cgtccagagc ttcaataggg gtgactgtta g |
| SEQ ID NO: 18 | 5'-atggagactg ggctgcgctg gcttctcctg<br>gtcgctgtgc tcaaaggtgt ccagtgtcag gagcagctgg<br>tggaatccgg aggaggcctg gtcacgcctg ggggatccct<br>gacactcacc tgcacagtct ctacaatcga cctcagtacc<br>tttgcaataa gctgggtccg ccaggctcca ggaaggggc<br>tggagtggat cggaaccatt aatactgatc ttaccacata<br>ctatgtgaat tgggcgaaag gccgattcac catctccaaa<br>acctcgtcga ccacggtgga tctgaaaatg accggtctga<br>caatcgagga cacggccacc tatttctgtg ccagaaaatt<br>atttggaaat ggtaatgtct ggggcccagg caccctggtc<br>accgtctctt cagggcaacc taaggctcca tcagtcttcc<br>cactggcccc ctgctgcggg gacacaccca gctccacggt<br>gaccctgggc tgcctggtca aagggtacct cccggagcca<br>gtgaccgtga cctggaactc gggcaccctc accaatgggg<br>tacgcacctt cccgtccgtc cggcagtcct caggcctcta<br>ctcgctgagc agcgtggtga gcgtgacctc aagcagccag<br>cccgtcacct gcaacgtggc ccaccagcc accaacacca |

SEQUENCE LISTING

```
aagtggacaa gaccgttgcg ccctcgacat gcagcaagcc
cacgtgccca ccccctgaac tcctgggggg accgtctgtc
ttcatcttcc ccccaaaacc caaggacacc ctcatgatct
cacgcacccc cgaggtcaca tgcgtggtgg tggacgtgag
ccaggatgac cccgaggtgc agttcacatg gtacataaac
aacgagcagg tgcgcaccgc ccggccgccg ctacgggagc
agcagttcaa cagcacgatc cgcgtggtca gcaccctccc
catcgcgcac caggactggc tgaggggcaa ggagttcaag
tgcaaagtcc acaacaaggc actcccggcc cccatcgaga
aaaccatctc caaagccaga gggcagcccc tggagccgaa
ggtctacacc atgggccctc cccggggagga gctgagcagc
aggtcggtca gcctgacctg catgatcaac ggcttctacc
cttccgacat ctcggtggag tgggagaaga cgggaaggc
agaggacaac tacaagacca cgcccggccgt gctggacagc
gacggctcct acttcctcta cagcaagctc tcagtgccca
cgagtgagtg gcagcggggc gacgtcttca cctgctccgt
gatgcacgag gccttgcaca accactacac gcagaagtcc
atctcccgct ctccgggtaa atga
```

SEQ ID NO: 19   RLRKGRMM

SEQ ID NO: 20   LRKGRMMD

SEQ ID NO: 21   RKGRMMDV

SEQ ID NO: 22   KGRMMDVK

SEQ ID NO: 23   GRMMDVKK

SEQ ID NO: 24   RMMDVKKC

SEQ ID NO: 25   MMDVKKCG

SEQ ID NO: 26   MDVKKCGI

SEQ ID NO: 27   DVKKCGIQ

SEQ ID NO: 28   VKKCGIQD

SEQ ID NO: 29   KKCGIQDT

SEQ ID NO: 30   KCGIQDTN

SEQ ID NO: 31   CGIQDTNS

SEQ ID NO: 32   GIQDTNSK

SEQ ID NO: 33   IQDTNSKK

SEQ ID NO: 34   QDTNSKKQ

SEQ ID NO: 35   DTNSKKQS

SEQ ID NO: 36   TNSKKQSD

SEQ ID NO: 37   NSKKQSDT

SEQ ID NO: 38   SKKQSDTH

SEQ ID NO: 39   KKQSDTHL

SEQ ID NO: 40   KQSDTHLE

SEQ ID NO: 41   QSDTHLEE

SEQ ID NO: 42   SDTHLEET

SEQ ID NO: 43   RLRKGRMMD

SEQ ID NO: 44   LRKGRMMDV

SEQ ID NO: 45   RKGRMMDVK

SEQ ID NO: 46   KGRMMDVKK

SEQ ID NO: 47   GRMMDVKKC

-continued

| SEQUENCE LISTING | |
|---|---|
| SEQ ID NO: 48 | RMMDVKKCG |
| SEQ ID NO: 49 | MMDVKKCGI |
| SEQ ID NO: 50 | MDVKKCGIQ |
| SEQ ID NO: 51 | DVKKCGIQD |
| SEQ ID NO: 52 | VKKCGIQDT |
| SEQ ID NO: 53 | KKCGIQDTN |
| SEQ ID NO: 54 | KCGIQDTNS |
| SEQ ID NO: 55 | CGIQDTNSK |
| SEQ ID NO: 56 | GIQDTNSKK |
| SEQ ID NO: 57 | IQDTNSKKQ |
| SEQ ID NO: 58 | QDTNSKKQS |
| SEQ ID NO: 59 | DTNSKKQSD |
| SEQ ID NO: 60 | TNSKKQSDT |
| SEQ ID NO: 61 | NSKKQSDTH |
| SEQ ID NO: 62 | SKKQSDTHL |
| SEQ ID NO: 63 | KKQSDTHLE |
| SEQ ID NO: 64 | KQSDTHLEE |
| SEQ ID NO: 65 | QSDTHLEET |
| SEQ ID NO: 66 | RLRKGRMMDV |
| SEQ ID NO: 67 | LRKGRMMDVK |
| SEQ ID NO: 68 | RKGRMMDVKK |
| SEQ ID NO: 69 | KGRMMDVKKC |
| SEQ ID NO: 70 | GRMMDVKKCG |
| SEQ ID NO: 71 | RMMDVKKCGI |
| SEQ ID NO: 72 | MMDVKKCGIQ |
| SEQ ID NO: 73 | MDVKKCGIQD |
| SEQ ID NO: 74 | DVKKCGIQDT |
| SEQ ID NO: 75 | VKKCGIQDTN |
| SEQ ID NO: 76 | KKCGIQDTNS |
| SEQ ID NO: 77 | KCGIQDTNSK |
| SEQ ID NO: 78 | CGIQDTNSKK |
| SEQ ID NO: 79 | GIQDTNSKKQ |
| SEQ ID NO: 80 | IQDTNSKKQS |
| SEQ ID NO: 81 | QDTNSKKQSD |
| SEQ ID NO: 82 | DTNSKKQSDT |
| SEQ ID NO: 83 | TNSKKQSDTH |
| SEQ ID NO: 84 | NSKKQSDTHL |
| SEQ ID NO: 85 | SKKQSDTHLE |
| SEQ ID NO: 86 | KKQSDTHLEE |

SEQUENCE LISTING

```
SEQ ID NO: 87   KQSDTHLEET

SEQ ID NO: 88   RLRKGRMMDVK

SEQ ID NO: 89   LRKGRMMDVKK

SEQ ID NO: 90   RKGRMMDVKKC

SEQ ID NO: 91   KGRMMDVKKCG

SEQ ID NO: 92   GRMMDVKKCGI

SEQ ID NO: 93   RMMDVKKCGIQ

SEQ ID NO: 94   MMDVKKCGIQD

SEQ ID NO: 95   MDVKKCGIQDT

SEQ ID NO: 96   DVKKCGIQDTN

SEQ ID NO: 97   VKKCGIQDTNS

SEQ ID NO: 98   KKCGIQDTNSK

SEQ ID NO: 99   KCGIQDTNSKK

SEQ ID NO: 100  CGIQDTNSKKQ

SEQ ID NO: 101  GIQDTNSKKQS

SEQ ID NO: 102  IQDTNSKKQSD

SEQ ID NO: 103  QDTNSKKQSDT

SEQ ID NO: 104  DTNSKKQSDTH

SEQ ID NO: 105  TNSKKQSDTHL

SEQ ID NO: 106  NSKKQSDTHLE

SEQ ID NO: 107  SKKQSDTHLEE

SEQ ID NO: 108  KKQSDTHLEET

SEQ ID NO: 109  5'-augauaauauggccacaaccaug

SEQ ID NO: 110  EQLVESGGGLVTPGGSLTLTCTVSTIDLSTFAISWVRQAPGKGLE
                WIGTINTDLTTYYVNWAKGRFTISKTSSTTVDLKMTGLTIEDTAT
                YFCARKLFGNGNVWGPGTLVTVSS

SEQ ID NO: 111  AQVLTQTPSPVSASVGSTVTINCQASQSLHRNNYLSWFQQKPGQP
                PKQLIYQASTLASGVSSRFSGSGSGTQFTLTISDVVCDDAATYYC
                LGGVSGGPYPFGGGTEVVVK

SEQ ID NO: 112  MDTRAPTQLLGLLLLWLPGATVA

SEQ ID NO: 113  METGLRWLLLVAVLKGVQC

SEQ ID NO: 114  QVLTQTPSPVSASVGSTVTINCQASQSLHRNNYLSWFQQKPGQPP
                KQLIYQASTLASGVSSRFSGSGSGTQFTLTISDVVCDDAATYYCL
                GGVSGGPYPFGGGTEVVVKGDPVAPTVLIFPPAADQVATGTVTIV
                CVANKYFPDVTVTWEVDGTTQTTGIENSKTPQNSADCTYNLSSTL
                TLTSTQYNSHKEYTCKVTQGTTSVVQSFNRGDC

SEQ ID NO: 115  QEQLVESGGGLVTPGGSLTLTCTVSTIDLSTFAISWVRQAPGKGL
                EWIGTINTDLTTYYVNWAKGRFTISKTSSTTVDLKMTGLTIEDTA
                TYFCARKLFGNGNVWGPGTLVTVSSGQPKAPSVFPLAPCCGDTPS
                STVTLGCLVKGYLPEPVTVTWNSGTLTNGVRTFPSVRQSSGLYSL
                SSVVSVTSSSQPVTCNVAHPATNTKVDKTVAPSTCSKPTCPPPEL
                LGGPSVFIFPPKPKDTLMISRTPEVTCVVVDVSQDDPEVQFTWYI
                NNEQVRTARPPLREQQFNSTIRVVSTLPIAHQDWLRGKEFKCKVH
                NKALPAPIEKTISKARGQPLEPKVYTMGPPREELSSRSVSLTCMI
                NGFYPSDISVEWEKNGKAEDNYKTTPAVLDSDGSYFLYSKLSVPT
                SEWQRGDVFTCSVMHEALHNHYTQKSISRSPGK
```

SEQUENCE LISTING

SEQ ID NO: 116 FGGGTEVVVK

SEQ ID NO: 117 WGPGTLVTVSS

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of".

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The described objectives are solved by the present invention, preferably by the subject matter of the appended claims.

The inventors have surprisingly found that the inventive antibody or antigen-binding fragment thereof is highly specific for PD-L1 and yields reproducible results in PD-L1 detection by immunohistochemistry to aid in the stratification of tumor patients amenable for an anti-PD-L1 based therapy.

The described objectives are solved according to a first embodiment by the inventive antibody or antigen-binding fragment thereof that binds to an epitope comprised in the amino acid sequence according to SEQ ID NO:1, wherein the antibody light chain or antigen binding fragment thereof comprises at least one of the amino acid sequences according to SEQ ID NO:3, SEQ ID NO: 4, SEQ ID NO: 5, SEQ ID NO: 6, SEQ ID NO: 7, SEQ ID NO: 8 and the antibody heavy chain or antigen binding fragment thereof comprise at least one of the amino acid sequences according to SEQ ID NO:9, SEQ ID NO: 10, SEQ ID NO: 11, SEQ ID NO: 12, SEQ ID NO: 13, SEQ ID NO: 14. For example, the antibody or antigen-binding fragment thereof according to the invention comprises in its light chain at least one of SEQ ID NO:3, SEQ ID NO: 4, SEQ ID NO: 5, SEQ ID NO: 6, SEQ ID NO: 7, SEQ ID NO: 8, or e.g. two, three, four, five, or all of SEQ ID NO:3, SEQ ID NO: 4, SEQ ID NO: 5, SEQ ID NO: 6, SEQ ID NO: 7, SEQ ID NO: 8. For example, the light chain may comprise SEQ ID NO:3, SEQ ID NO: 4, SEQ ID NO: 5, SEQ ID NO: 6, SEQ ID NO: 7, SEQ ID NO: 8, or e.g. SEQ ID NO:3, SEQ ID NO: 4, SEQ ID NO: 5; SEQ ID NO: 4, SEQ ID NO: 5, SEQ ID NO: 6; SEQ ID NO: 5, SEQ ID NO: 6, SEQ ID NO: 7; SEQ ID NO: 6, SEQ ID NO: 7, SEQ ID NO: 8, or e.g. SEQ ID NO:3, SEQ ID NO: 4, SEQ ID NO: 5, SEQ ID NO: 6; SEQ ID NO: 4, SEQ ID NO: 5, SEQ ID NO: 6, SEQ ID NO: 7; SEQ ID NO: 5, SEQ ID NO: 6, SEQ ID NO: 7, SEQ ID NO: 8, or e.g. SEQ ID NO:3, SEQ ID NO: 4, SEQ ID NO: 5, SEQ ID NO: 6, SEQ ID NO: 7, SEQ ID NO: 8, SEQ ID NO: 116, and the antibody heavy chain or antigen binding fragment thereof comprise at least one of SEQ ID NO:9, SEQ ID NO: 10, SEQ ID NO: 11, SEQ ID NO: 12, SEQ ID NO: 13, SEQ ID NO: 14, e.g. two, three, four, five, or all of SEQ ID NO:9, SEQ ID NO: 10, SEQ ID NO: 11, SEQ ID NO: 12, SEQ ID NO: 13, SEQ ID NO: 14, e.g. SEQ ID NO:9, SEQ ID NO: 10, SEQ ID NO: 10, SEQ ID NO: 11, SEQ ID NO: 11, SEQ ID NO: 12; SEQ ID NO: 12, SEQ ID NO: 13; SEQ ID NO: 13, SEQ ID NO: 14, or e.g. SEQ ID NO:9, SEQ ID NO: 10, SEQ ID NO: 11; SEQ ID NO: 10, SEQ ID NO: 11, SEQ ID NO: 12; SEQ ID NO: 11, SEQ ID NO: 12, SEQ ID NO: 13; SEQ ID NO: 12, SEQ ID NO: 13, SEQ ID NO: 14, or e.g. SEQ ID NO:9, SEQ ID NO: 10, SEQ ID NO: 11, SEQ ID NO: 12; SEQ ID NO: 10, SEQ ID NO: 11, SEQ ID NO: 12, SEQ ID NO: 13; SEQ ID NO: 11, SEQ ID NO: 12, SEQ ID NO: 13, SEQ ID NO: 14; or e.g. SEQ ID NO:9, SEQ ID NO: 10, SEQ ID NO: 11, SEQ ID NO: 12, SEQ ID NO: 13, SEQ ID NO: 14, or e.g. SEQ SEQ ID NO:9, SEQ ID NO: 10, SEQ ID NO: 11, SEQ ID NO: 12, SEQ ID NO: 13, SEQ ID NO: 14, SEQ ID NO: 117. The light chain and heavy chain amino acid sequence elements as disclosed above may e.g. be present in numerically increasing order of the SEQ ID numbers listed, and, if all of the heavy and light chain sequence elements are present in the inventive antibody or antigen-binding fragment thereof, it is preferred that the light chain sequence elements are comprised in the order SEQ ID NO:3, SEQ ID NO: 4, SEQ ID NO: 5, SEQ ID NO: 6, SEQ ID NO: 7, SEQ ID NO: 8, SEQ ID NO: 116 and the heavy chain sequence elements are comprised in the order of SEQ ID NO:9, SEQ ID NO: 10, SEQ ID NO: 11, SEQ ID NO: 12, SEQ ID NO: 13, SEQ ID NO: 14, SEQ ID NO: 117. As used for the inventive antibody the term "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as immunoglobulin variable region genes. Antibody light chains are classified as either kappa or lambda. Antibody heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD) (see e.g. J Allergy Clin Immunol. 2010 February; 125(2 0 2): S41-S52). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

According to one embodiment the inventive antibody or antigen-binding fragment thereof is a monoclonal antibody, an Fab, F(ab')2, Fab', scFv, or di-scFv. Antibodies exist as intact immunoglobulins or e.g. as a well-characterized antigen-binding fragments produced by digestion with peptidases such as pepsin, or papain: Pepsin will result in proteolytic cleavage below the disulfide linkages and result in a F(ab')2 antibody fragments, while proteolytic cleavage by papain, which cleaves above the disulfide linkages, will result in two Fab fragments. Accordingly a $F(ab')_2$ fragment is a dimer of Fab which itself is a light chain joined to $V_H$-$C_{H1}$ by a disulfide bond. The $F(ab')_2$ may be reduced under mild conditions to break the disulfide linkage in the hinge region, thereby converting the F(ab)'$_2$ dimer into an Fab' monomer. The aforementioned antibody fragments are defined in terms of the digestion of an intact antibody with pepsin and papain, however, such fragments may be synthesized de novo either chemically or by using recombinant DNA methodology.

The term "antigen-binding fragment thereof" according to the invention refers to (i) a Fab fragment, a monovalent fragment consisting of the VL, VH, CL and CH1 domains, (ii) a $F(ab')_2$ fragment, a bivalent fragment comprising two Fab fragments linked by a disulfide bridge at the hinge region, (iii) a Fd fragment consisting of the VH and CH1 domains, (iv) a Fv fragment consisting of the VL and VH domains of a single arm of an antibody, (v) a dAb fragment (see e.g. Ward et al (1989) Nature 341 544-46), which comprises a VH domain, and (vi) an isolated complementarity determining region (CDR). The term "scFv" as used in the present invention refers to a molecule comprising an antibody heavy chain variable domain (or region; VH) and an antibody light chain variable domain (or region; VL) connected by a linker, and lacks constant domains, e.g. an scFv fragment according to the invention may e.g. include binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an linker interposed between the VH domain and the VL domain, which may e.g. include a peptide sequence comprised of the amino acids glycine and serine. For example, the peptide sequence may comprise the amino acid sequence $(Gly_4 Ser)_n$, whereby n is an integer from 1-6, e.g. n may be 1, 2, 3, 4, 5, or 6, preferably n=4. scFv molecules and methods of obtaining them are known in the art and are described, e.g., in U.S. Pat. No. 5,892,019, Ho et al. 1989. Gene 77:51; Bird et al. 1988 Science 242:423; Pantoliano et al. 1991. Biochemistry 30:10117; Milenic et al. 1991. Cancer Research 51:6363; Takkinen et al. 1991. Protein Engineering 4:837. The term "di-scFv" as used for the inventive antigen-binding fragments refer to two scFv fragments which are coupled to each other via a linker, e.g. such as disclosed in Cancer Research 54, 6176-618, Dec. 1, 1994, or Chem Commun (Camb). 2007 Feb. 21; (7):695-7.

According to one embodiment the antibody or antigen binding fragment according to the invention is a monoclonal antibody. The term "monoclonal antibody" as used for the inventive antibody, refers to an antibody obtained from a population of substantially homogeneous antibodies. Monoclonal antibodies are identical except for possible naturally occurring mutations that may be present in minor amounts, or minor differences in their glycosylation pattern. Monoclonal antibodies, such as e.g. the inventive monoclonal antibody, are highly specific, being directed against a single antigenic site and specifically bind to a single epitope within the antigen, unlike polyclonal antibody preparations which typically include different antibodies directed against different epitopes. Monoclonal antibodies may e.g. be obtained by hybridoma culture as e.g. described by Kohler et al., (1975) Nature, 256:495, or may be made by recombinant DNA methods (see, e.g., U.S. Pat. No. 4,816,567).

According to one embodiment the inventive antibody is an IgG type monoclonal antibody, e.g. the inventive antibody may be a human IgG1, IgG2, IgG3, or IgG4 type monoclonal antibody, or e.g. murine IgG1, IgG2a, IgG2b, IgG2c, IgG3, or e.g. rat IgG1, IgG2a, IgG2b, IgG2c. For example, the inventive IgG type monoclonal antibody may be of any origin, e.g. of murine, goat, sheep, hamster, rat, or rabbit origin.

According to a preferred embodiment the inventive antibody or the antigen-binding fragment thereof comprises all of the light chain amino acid sequences according to SEQ ID NO:3, SEQ ID NO: 4, SEQ ID NO: 5, SEQ ID NO: 6, SEQ ID NO: 7, SEQ ID NO: 8.

In a preferred embodiment, the inventive antibody or the antigen-binding fragment thereof comprises all of the heavy chain amino acid sequences according to SEQ ID NO:9, SEQ ID NO: 10, SEQ ID NO: 11, SEQ ID NO: 12, SEQ ID NO: 13, SEQ ID NO: 14.

In one embodiment, the inventive antibody or antigen-binding fragment thereof comprises three CDRs from the variable region of the light chain which comprises the amino acid sequence according to SEQ ID NO: 111 and three CDRs from variable region of the heavy chain which comprises the amino acid sequence according to SEQ ID NO:110.

In one preferred embodiment, the inventive antibody or antigen-binding fragment thereof comprises three CDRs from the variable region of the light chain which comprises the amino acid sequence according to SEQ ID NO: 111, and three CDRs from variable region of the heavy chain which comprises the amino acid sequence according to SEQ ID NO:110, and the CDRs of the light chain comprise or are comprised in the amino acid sequences according to SEQ ID NO: 4, SEQ ID NO: 6 and SEQ ID NO: 8 and the CDRs of the heavy chain comprise or are comprised in the amino acid sequences according to SEQ ID NO: 10, SEQ ID NO: 12 and SEQ ID NO: 14.

In one preferred embodiment, the inventive antibody or antigen-binding fragment thereof as disclosed above comprises a light and heavy chain which comprise the CDRs as defined above whereby the light chain variable region according to SEQ ID NO: 111 further comprises four framework regions (FR) and the heavy chain variable region according to SEQ ID NO:110 further comprises four framework regions, whereby the framework regions of the light chain variable region comprise or are comprised in the amino acid sequences according to SEQ ID NO: 3, SEQ ID NO: 5, SEQ ID NO: 7, SEQ ID NO: 116, and the framework regions of the heavy chain variable region comprise or are comprised in the amino acid sequences according to SEQ ID NO: 9, SEQ ID NO: 11, SEQ ID NO: 13, SEQ ID NO: 117.

According to a preferred embodiment the heavy chain of the inventive antibody (or e.g. an antigen-binding fragment thereof) comprises a variable region which comprises the amino acid sequence according to SEQ ID NO: 110 and the light chain of the inventive antibody (or e.g. an antigen-binding fragment thereof) comprises a variable region which comprises the amino acid sequence according to SEQ ID NO: 111.

According to a more preferred embodiment the inventive antibody or antigen-binding fragment thereof comprises a light chain which comprises the amino acid sequence according to SEQ ID NO: 114 in which the signal sequence has been removed, e.g. the amino acid sequence according to SEQ ID NO: 112, e.g. by proteolytic cleavage and a heavy chain which comprises the amino acid sequence according to SEQ ID NO: 115 in which the signal sequence has been removed, e.g. the amino acid sequence according to SEQ ID NO: 113, e.g. by proteolytic cleavage.

In one embodiment, the variable light chain (VL) and the variable heavy chain ($V_H$) of the inventive antibody, e.g. comprising the amino acid sequences according to SEQ ID NO: 110 and SEQ ID NO: 111 may be comprised in a scFv, or e.g. a Fab which e.g. may be further be linked to a GA-SEED, or an AG-SEED. The term "SEED" as refers to strand-exchange engineered domain (SEED) CH3 heterodimers as disclosed in WO2007/110205 A2, Protein Engineering, Design & Selection vol. 23 no. 4 pp. 195-202, 2010. These heterodimeric molecules are derivatives of human IgG and IgA CH3 domains and create complementary human SEED CH3 heterodimers that are composed of alternating segments of human IgA and IgG CH3 sequences. The resulting pair of SEED CH3 domains preferentially associates to form heterodimers in a 1:1 ratio when expressed in mammalian cells to form "SEEDbodies" (Sb). The term "GA-SEED" hereby indicates that the SEED molecule begins with an IgG sequence, followed by an IgA sequence, while "AG-SEED" refers to the fact that the SEED molecule begins with an IgA-derived sequence followed by an IgG-derived sequence. The inventive scFv comprising the amino acid sequences according to SEQ ID NO: 110 and SEQ ID NO: 110 may e.g. be linked to the GA- or AG-SEED via a peptide linker e.g. via a glycine-serine linker of the amino acid sequence $(Gly_4 Ser)_n$ as disclosed above.

According to a more preferred embodiment the inventive antibody light chain or antigen-binding fragment thereof comprises the amino acid sequence according to SEQ ID NO: 15 and the inventive antibody heavy chain or antigen-binding fragment thereof comprises the amino acid sequence according to SEQ ID NO: 16. For example, the inventive antibody or antigen-binding fragment thereof may comprise the amino acid sequences according to SEQ ID NO: 15 in its light chain and the amino acid sequence according to SEQ ID NO: 16 in its heavy chain. For example, both heavy and light chain sequences of the inventive antibody or antigen binding fragment thereof may comprise amino acid substitutions in the amino acid sequences not comprised in any of SEQ ID NO:3, SEQ ID NO: 4, SEQ ID NO: 5, SEQ ID NO: 6, SEQ ID NO: 7, SEQ ID NO: 8, or SEQ ID NO: 111 for the light chain and SEQ ID NO:9, SEQ ID NO: 10, SEQ ID NO: 11, SEQ ID NO: 12, SEQ ID NO: 13, SEQ ID NO: 14, or SEQ ID NO: 110 for the heavy chain, e.g. in amino acids that do not form part of the variable region of the light or heavy chain, or e.g. any light or heavy chain CDR or framework sequences, e.g. amino-terminally or carboxy-terminally to SEQ ID NO:3, SEQ ID NO: 4, SEQ ID NO: 5, SEQ ID NO: 6, SEQ ID NO: 7, SEQ ID NO: 8, or e.g. SEQ ID NO: 111 of the light chain, or SEQ ID NO:9, SEQ ID NO: 10, SEQ ID NO: 11, SEQ ID NO: 12, SEQ ID NO: 13, SEQ ID NO: 14, or SEQ ID NO: 110 of the heavy chain of the inventive antibody. Amino acid substitutions may e.g. be non-conservative amino acid substitutions, or conservative amino acid substitutions. The term "conservative amino acid substitutions" as used in the present invention refers to an amino acid substitution in which the substituted amino acid residue is of similar charge as the replaced residue and is of similar or smaller size than the replaced residue. Conservative substitutions of amino acids include substitutions made e.g. amongst amino acids within the following groups:

| Class | Amino acid |
|---|---|
| Aliphatic | Glycine, Alanine, Valine, Leucine, Isoleucine |
| Hydroxyl or Sulfur/Selenium-containing | Serine, Cysteine, Selenocysteine, Threonine, Methionine |
| Cyclic | Proline |
| Aromatic | Phenylalanine, Tyrosine, Tryptophane |
| Basic | Histidine, Lysine, Arginine |
| Acidic | Aspartate, Glutamate, Asparagine, Glutamine |

According to a preferred embodiment, the inventive monoclonal IgG antibody is a rabbit antibody, or e.g. a rabbit-derived antibody. The inventive rabbit IgG monoclonal antibody may e.g. be generated according to the methods disclosed in Antibodies: A Laboratory Manual, Second Edition, Chapter 7, Edited by Edward A. Greenfield, CSH Press, ISBN 978-1-936113-81-1, or e.g. according to any suitable method in the art such as those disclosed in Proc. Natl. Acad. Sci. USA, Vol. 92, pp. 9348-9352, September 1995, or e.g. U.S. Pat. No. 7,732,168 B2. The term "rabbit-derived" as used for the inventive antibody refers to an antibody that was produced in a heterologous expression system (e.g. CHO cells, HEK293 cells) using polynucleotide sequences obtained from a rabbit hybridoma producing the respective antibody, such as e.g. the inventive antibody. For example, a rabbit-derived antibodies of the invention includes antibodies that may be produced in CHO or HEK cells transfected with an expression vector comprising polynucleotides encoding the amino acid sequence (e.g. according to SEQ ID NO: 15 and/or SEQ ID NO:16) of the antibody produced by a rabbit hybridoma cell. For example, recombinant monoclonal antibodies according to the invention may be generated from rabbit hybridoma cells producing the inventive antibody by the method as disclosed in PLoS One. 2016 Mar. 29; 11(3):e0152282. For example, cDNA from a single B cells may be prepared using Superscript III reverse transcriptase (Invitrogen) primed with oligo (dT). Antibody variable-region genes may then be recovered via two rounds of PCR using either KOD DNA polymerase (EMD Millipore) or TaqPlus Precision DNA polymerase (Agilent). A primary PCR may e.g. utilize gene-specific primers at both the 5' and 3' ends of the antibody variable region. The 5' oligonucleotide set may bind e.g. at the 5' end of the leader sequence and the 3' reverse primer set may anneal to CH1 or OK region respectively. In the secondary PCR, a single 5' forward oligonucleotide that anneals to a "tail" encoded at the 5' end of the primary PCR product may be used with a 3' primer set that anneals in the J region. The secondary oligonucleotides may e.g. be used to introduce restriction sites to facilitate downstream cloning. Heavy and light chain PCR fragments may then e.g. be subcloned into to suitable expression vectors (e.g. pCMV) and transfected into Expi293 cells (Life technologies) using Expi293-fectamine (Life Technologies) according to the manufacturers' instructions. The transfected cells may then e.g. grown for 7 days at 37° C. in a 5% CO2 environment using growth media that in allow the production of the inventive antibody. Resultant supernatants may e.g. harvested after 5 to 7 days.

In one embodiment the inventive antibody or antigen-binding fragment thereof as is further coupled to a detectable label. As used for the inventive antibody or antigen-binding fragment thereof the term "detectable label" refers to a molecule capable of detection, which may e.g. include radioactive isotopes, fluorescent probes, chemiluminescences, enzymes, enzyme substrates, enzyme cofactors, enzyme inhibitors, dyes, metal ions, or biotin. The term "coupled" as used for the inventive antibody or antigen-binding fragment thereof refers to the fact that the dye, radioisotope may e.g. be non-covalently via e.g. ionic, or hydrophobic interactions, or covalently attached to inventive antibody or antigen-binding fragment thereof. Coupling of the detectable labels as disclosed above such as e.g. of fluorescent probes, dyes, or enzymes to the inventive antibody or antigen-binding fragment thereof as disclosed above may e.g. be done according to methods known in the art such as those disclosed in Methods Cell Biol. 2001; 63:185-204; Methods Mol Biol. 2010; 588:43-8; Curr Protoc Mol Biol. 2001 May; Chapter 11: Unit 11.1.

According to one embodiment the detectable label coupled to the inventive antibody or antigen-binding fragment thereof is one of an enzyme, or fluorophore, or enzyme substrate. For example, the detectable label coupled to the inventive antibody or antigen-binding fragment thereof may be alkaline phosphatase, horseradish peroxidase, beta-galactosidase, Tobacco Etch Virus nuclear-inclusion-a endopeptidase ("TEV protease"). The fluorophore which may e.g. be coupled to the inventive antibody as disclosed above may be one of 1,8-ANS, 4-methylumbelliferone, 7-amino-4-methylcoumarin, 7-hydroxy-4-methylcoumarin, Acridine, Alexa Fluor 350™, Alexa Fluor 405™, AMCA, AMCA-X, ATTO Rho6G, ATTO Rho11, ATTO Rho12, ATTO Rho13, ATTO Rho14, ATTO Rho101, Pacific Blue, Alexa Fluor 43Q™ Alexa Fluor480™, Alexa Fluor488™, BODIPY 492/515, Alexa Fluor 532™, Alexa Fluor 546™, Alexa Fluor555™ Alexa Fluor594™ BODIPY 505/515, Cy2, cyQUANT GR, FITC, Fluo-3, Fluo-4, GFP (EGFP), mHoneydew, Oregon Green™ 488, Oregon Green™ 514, EYFP, DsRed, DsRed2, dTomato, Cy3.5, Phycoerythrin (PE), Rhodamine Red, mTangerine, mStrawberry, mOrange, mBanana, Tetramethylrhodamine (TRITC), R-Phycoerythrin, ROX, DyLight 594, Calcium Crimson, Alexa Fluor594™, Alexa Fluor610™, Texas Red, mCherry, mKate, Alexa Fluor660™, Alexa Fluor680™ allophycocyanin, DRAQ-5, carboxynaphthofluorescein, C7, DyLight 750, Cellvue NIR780, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxy coumarin, Naphtho fluorescein, PyMPO, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, HEX, 6-JOE, NBD (7-nitrobenz-2-oxa-1, 3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, or La Jolla blue dye. Fluorophores which may be coupled to the inventive antibody or antigen-binding fragment may e.g. also include quantum dots. The term quantum dot as used in the present invention refers to a single spherical nanocrystal of semiconductor material where the radius of the nanocrystal is less than or equal to the size of the exciton Bohr radius for that semiconductor material (the value for the exciton Bohr radius can be calculated from data found in handbooks containing information on semiconductor properties, such as the CRC Handbook of Chemistry and Physics, 83rd ed., Lide, David R. (Editor), CRC Press, Boca Raton, Fla. (2002)). Quantum dots are known in the art, as they are described in references, such as Weller, Angew. Chem. Int. Ed. Engl. 32: 41-53 (1993), Alivisatos, J. Phys. Chem. 100: 13226-13239 (1996), and Alivisatos, Science 271: 933-937 (1996). Quantum dots may e.g. be from about 1 nm to about 1000 nm diameter, e.g. 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, or 500 nm, preferably at least about 2 nm to about 50 nm, more preferably QDs are at least about 2 nm to about 20 nm in diameter (for example about 2, 3, 4, 5, 6, 7, 8, 9, 10, 11, 12, 13, 14, 15, 16, 17, 18, 19, or 20 nm). QDs are characterized by their substantially uniform nanometer size, frequently exhibiting approximately a 10% to 15% polydispersion or range in size. A QD is capable of emitting electromagnetic radiation upon excitation (i.e., the QD is photoluminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS. Quantum dots may e.g. be coupled to the inventive antibody or antigen-binding fragment thereof by any method known in the art such as the methods disclosed in Nanotechnology. 2011 Dec. 9; 22(49):494006; Colloids and Surfaces B: Biointerfaces 84 (2011) 360-368.

In one example the inventive antibody or antigen-binding fragment thereof may be coupled to a radioisotope such as $^{47}$Ca, $^{14}$C, $^{137}$Cs, $^{157}$Cr, $^{57}$Co, $^{60}$Co, $^{67}$Cu, $^{67}$Ga, $^{123}$I, $^{125}$I, $^{129}$I, $^{131}$I, $^{32}$P, $^{75}$Se, $^{85}$Sr, $^{35}$S, $^{201}$Th, $^{3}$H, preferably, the radioisotopes are incorporated into a further molecule, such as e.g. a chelator. Typical chelators that may be used according to the invention are for example DPTA, EDTA (Ethylenediamine-tetraacetic acid), EGTA (Ethyleneglycol-O, O'-bis(2-aminoethyl)-N,N,N',N'-tetraacetic acid, NTA (Nitrilotriacetic acid), HEDTA (N-(2-Hydroxyethyl)-ethylenediamine-N,N',N'-triacetic acid), DTPA (2-[Bis[2-[bis (carboxymethyl)amino]-ethyl]amino]acetic acid), or DOTA (1,4,7,10-tetraazacyclo-dodecane-1,4,7,10-tetraacetic acid).

In one embodiment the inventive antibody or antigen-binding fragment thereof is for use in detecting the presence or expression of an epitope comprised in SEQ ID NO: 1 in a sample. For example, the inventive antibody or antigen-binding fragment thereof is for use in detecting the expression of an epitope comprised in the amino acid sequence according to SEQ ID NO: 1, whereby SEQ ID NO: 1 corresponds to an intracellular portion of human PD-L1 spanning amino acid residues 260-290 of GenBank accession no. AAH69381. The epitope comprised in the amino acid sequence according to SEQ ID NO: 1 (e.g. within the intracellular domain of human PD-L1) may e.g. be reliably and reproducibly detected through the use of the inventive antibody or antigen-binding fragment thereof by means of immunohistochemistry on e.g. FFPE tissue samples, or tumor tissue samples. The term "epitope" as used for the present invention which is comprised in SEQ ID NO: 1 (RLRKGRMMDVKKCGIQDTN SKKQSDTHLEET) refers to a portion of SEQ ID NO: 1 having antigenic or immunogenic activity in an animal, preferably a mammal, and most preferably in a rabbit. The epitope comprised in SEQ ID NO: 1 according to the invention may e.g. be a linear epitope, or a conformational epitope. A conformational epitope may e.g. be composed of discontinuous sections of the amino acid sequence of SEQ ID NO: 1 and may e.g. interact with the paratope of the inventive antibody, or antigen-binding fragment as disclosed above based on its 3-dimensional surface features and shape or tertiary structure of SEQ ID NO: 1. The epitope comprised in SEQ ID NO: 1 according to the invention may e.g. also be a linear epitope formed by a continuous sequence of amino acids of SEQ ID NO: 1 which interacts with the paratope of the inventive antibody or antigen-binding fragment thereof based on the primary amino acid sequence of SEQ ID NO: 1 (RLRKGRMMDVKKCGIQDTNSKK QSDTHLEET). Accordingly, the paratope of inventive antibody or antigen-binding fragment thereof may e.g. bind to a linear epitope comprised in the amino acid sequence according SEQ ID NO: 1 and may e.g. have a length of about 1, 2, 3, 4, 5, 6, 7, 8, 9, 10 to about 11, 12, 13, 14, 15, 16, 17, 18, 19, 20 amino acids, or of about 2 to about 3, 4, 5, 6, 7, 8, 9, 10 amino acids, or e.g. of about 8 amino acid to about 11 amino acids For example, the linear epitope which interacts with the paratope of the inventive antibody or antigen-binding fragment thereof may comprise, or may be comprised in an amino acid sequences according to SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64. SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO, 106, SEQ ID NO: 107, SEQ ID NO: 108. For example, the inventive antibody or antigen-binding fragment thereof as disclosed above may be used to detect the presence or expression of an epitope as disclosed above in a sample, which may e.g. be a biological sample such as a body fluid, or a blood sample. For example, the biological sample, such as body fluid, or blood sample may be subjected to flow cytometry, or e.g. FACS using the inventive antibody or antigen-binding fragment thereof to detect the absence or presence of an epitope comprised in SEQ ID NO: 1, or as comprised in e.g. any of the amino acid sequences according to SEQ ID NO: 19-SEQ ID NO: 108 of the invention. For example, cells obtained by a needle biopsy, may be blocked for 10 minutes at room temperature with FcR blocker (e.g. TruStain FcX™ (Biolegend, San Diego; or e.g. Human BD Fc Block™, BD Biosciences) in a 1:1000 dilution and then incubated with the inventive antibody or antigen-binding fragment thereof, whereby the inventive antibody or antigen-binding fragment thereof may be coupled to a fluorescent probe, e.g. phycoerythrin [PE] in a dilution of about 1:50 to about 1:500, e.g. from about 1:75, 1:100, 1:125, 1:150, 1:175, 1:200 to about 1:250, 1:275, 1:300, 1:350, 1:400, 1:450, or e.g. 1:25, 1:50, 1:100, 1:150, 1:200, 1:250, 1:300, 1:400, 1:500 in PBS+2% serum for 15 minutes in the dark at room temperature. Cells may then e.g. be analyzed on an Attune flow cytometer (Life Technologies, Grand Island, N.Y.) and the results evaluated using FlowJo 10.0 software (Tree Star, Inc., Ashland, Oreg.). For example, the cells may additionally be counterstained with carboxyfluorescein diacetate succinimidyl ester (CFSE, Biolegend, San Diego, Calif.) at a final concentration of 5 µM for 10 minutes at 37° C. in darkness, followed by two washes with RPMI-1640 medium.

According to a preferred embodiment the inventive antibody or antigen-binding fragment thereof may be used to detect the presence or expression of an epitope comprised in SEQ ID NO: 1, e.g. comprised in a linear epitope in any one of the amino acid sequences according to SEQ ID NO:

19-SEQ ID NO: 108, in a tissue sample, fixed tissue sample, or a formaldehyde-fixed paraffin-embedded (FFPE) tissue. The term "tissue sample" according to the invention may e.g. refer to single cells derived from a tumor, or tissue suspected to be a tumor, or at least about $10^2$, $10^3$, $10^4$, $10^5$, $10^6$ or more cells derived from a tumor tissue or tissue suspected to be a tumor which may e.g. also comprise cultured tumor cells, e.g. as described in Trends Biotechnol. 2013 Jun.; 31(6): 347-354; Cancer Cell Culture: Methods and Protocols (Methods in Molecular Medicine); S. P. Langdon (Ed.), Humana Press, ISBN: 978-1588290793.

The cells or tissue may e.g. be obtained by way of non-invasive means, including, but not limited to, fine needle aspiration and needle biopsy, or, alternatively, by e.g. an invasive method, including, but not limited to, surgical biopsy. The methods of obtaining the tissue sample do not form part of the present invention. The term "fixed tissue sample" according to the invention refers to a tissue sample which has been subjected to chemical tissue fixation. For example, chemical fixation may include fixation with methanol, ethanol, acetone, methanol-acetone mix, buffered formalin solution, glutaraldehyde, or buffered paraformaldehyde. For example, fixation may include treatment (fixation) of the tissue sample as disclosed above with 10% saturated aqueous formaldehyde buffered to pH 6.8-7.2 with 100 mM phosphate buffer, or 10% neutral buffered formalin (NBF) with varying times at temperatures ranging from 4°-45° C., e.g. room temperature (20-25° C.), or e.g. from about 5° C., 6° C., 7° C., 8° C., 9° C., 10° C. to about 15° C., 17.5° C., 20° C., or from about 12° C., 15° C., 17.5 C, 20° C. to about 25° C., 27° C., 30° C., 35° C., 40° C., 45° C. for varying amounts of time. For example, the tissue samples as disclosed above may be fixed for about 5 minutes to about 24 hours, or from about 10 min, 15 min, 30 min, 45 min, 60 min, 90 min, 120 min, 180 min to about 15 min, 30 min, 45 min, 1 h, 4 h, 5 h, 6 h, 7 h, 8 h, 9 h, 10 h, 11 h, 12 h, 14 h, 16 h, 18 h, 20 h, 24 h, 48 h. For example, fixed tissue samples may include tissue samples that were fixed by immersion fixation with 10% NBF for about 18-24 h. For example, a fixed tissue sample according to the invention may includes a tissue sample as disclosed above which has been fixed, or treated according to standard protocols available in the art, such as those provided on the website www.ihcworld.com, e.g. as described in Hopwood D. Fixatives and fixation: a review. Histochem J. 1969; 1(4):323-60, or e.g. as described in "Immunohistochemical Staining Methods", $5^{th}$ edition (2009), published by DAKO North America, Inc. For example formaldehyde-fixed paraffin-embedded (FFPE) tissues may be obtained by the following procedure:

The tumor tissue as disclosed above may e.g. be placed in at least 10 volumes of buffered formalin (3.7% formaldehyde: 10 mM phosphate buffer, ph-7.4) or buffered paraformaldehyde (3.7% paraformaldehyde: 10 mM phosphate buffer, ph-7.4), followed by incubation in the buffered formalin, or NBF, for varying amounts of time depending on the thickness of the tissue sample as disclosed above e.g. for a 1-2 mm tissue sample, 2-3h at RT, for a 5-10 mm thick tissue sample—5 h RT, or e.g. for a tissue sample >10 mm in thickness 2-3 h RT, or e.g. at 4° C. overnight. Subsequently, the tissue may e.g. be rinsed 1-2× with PBS, and stored at 4° C. in 70% ethanol in $H_2O$ and then placed in the tissue processing histology cassettes and labeled for later identification. The histology cassettes may then e.g. be subjected to paraffin embedding using a commercial tissue processor 70% ethanol for 1 hour; 95% ethanol (95% ethanol/5% methanol) for 1 hour; first absolute ethanol for 1 hour; second absolute ethanol 1½ hours; third absolute ethanol 1½ hours; fourth absolute ethanol 2 hour; first clearing agent (xylene or substitute) 1 hour; second first clearing agent (xylene or substitute) 1 hour; first wax (Paraplast X-tra) at 58° C. for 1 hour; second wax (Paraplast X-tra) at 58° C. 1 hour. The formalin-fixed paraffin-embedded tissue may then be placed in a mold for further processing.

In one embodiment inventive antibody or antigen-binding fragment thereof as disclosed above is used in the detection of an epitope comprised in the amino acid sequences according to SEQ ID NO: 1, e.g. as comprised in any of the amino acid sequences according to SEQ ID NO: 19-SEQ ID NO: 108 as disclosed above in a tissue sample, fixed tissue sample, or FFPE tissue sample derived from a tumor, e.g. the tissue obtained from a tumor by means of a biopsy as disclosed above. The term "derived from a tumor" according to the invention may e.g. also include tumor cells obtained by needle aspiration, or e.g. cells tumor cells obtained by needle aspiration which have been cultivated.

According to one embodiment the detection of the epitope comprised in the amino acid sequence according to SEQ ID NO:1 is done by means of immunohistochemistry (IHC), flow cytometry, ELISA, or western blotting. For example, the tissue sample, or tumor tissue sample according to the invention, may be subjected to immunoblotting to detect the epitope comprised in SEQ ID NO: 1 using the antibody or antigen binding fragment thereof according to the invention as described in Current Protocols in Molecular Biology 10.8.1-10.8.28, July 2008.

If, for example, an ELISA is used for the detection of the epitope comprised in SEQ ID NO: 1 using the inventive antibody or antigen-binding fragment thereof, the ELISA may be done according to standard protocols, such e.g. as disclosed in Current Protocols in Molecular Biology (1991) 11.2.1-11.2.22. Preferably, the epitope comprised in SEQ ID NO: 1 is detected by means of immunohistochemistry (IHC) on FFPE tissue samples using the inventive antibody, or an antigen binding fragment thereof (e.g. as primary antibody): For example, the FFPE tumor tissue sample may be deparaffinized by placing dry paraffin sections on slides in a 60° C. oven for 1 hr. Subsequently, the slides may e.g. be placed in Sakura staining racks and immersed in Tissue-Tek® staining dishes containing the following solutions: three times in xylene for 5 min each two times in 100% ethanol for at least 1 min each two times in 95% ethanol for at least 1 min each one time in 70% ethanol for at least 1 min. The slides may then be gently rinsed with tap water for about 5 minutes. Depending on the tumor tissue the sample is derived from it may e.g. be required to block endogenous peroxidase activity by placing the slides in a 3% hydrogen peroxide solution for 10 minutes at room temperature, followed by a rinse with water. Subsequent antigen retrieval may e.g. be done in a water bath according to the following procedure: Slides may be placed in a Coplin jar with antigen retrieval solution such as e.g. Target Retrieval Solution, enhanced citrate buffer solution (Dako, S1699 or S1700), and Target Retrieval Solution, high pH (Dako, S3308), or 0.05M citrate buffer, pH 6, or e.g. Tris EDTA buffer, pH 8. Slides may e.g. then be allowed to equilibrate to 75° to 95° C. in a water bath and incubated for about 40 minutes. The slides may e.g. then be allowed to cool at room temperature for 20 min after which the solution is decanted and the slides may then be placed in a staining dish containing TBS/0.6% Tween 20 for a minimum of 5 minutes. Antigen retrieval may e.g. also be dine using a PT link pretreatment module (DAKO) using Tris-EDTA buffer pH 9 at 97° C. for 20 minutes. Following the antigen retrieval the slides may then be subjected to the staining procedure using an automated instrument (e.g. Discovery XT®, or AutostainerLink 48) following the manufacturer's instructions. For example, the slides may also be manually processed as described in Current Protocols in Molecular Biology 14.6.1-14.6.23, January 2008. For example, the slides may be covered with 400 to 500 μl of the antibody according to the invention diluted e.g. into commercially available antibody diluent (e.g. from DAKO) to a concentration of about 0.2 μg/ml to about 5 μg/ml, e.g. from about 0.2 μg/ml, 0.3 μg/ml, 0.4 μg/ml, 0.5 μg/ml, 0.6 μg/ml, 0.7 μg/ml, 0.8 μg/ml, 0.9 μg/ml, 1.0 μg/ml, 1.25 μg/ml, 1.5 μg/ml, 1.75 μg/ml, 2.0 μg/ml to about 3 μg/ml, 3.5 μg/ml, 4 μg/ml, 4.5 μg/ml, 5 μg/ml, 5.5 μg/ml, 6.0 μg/ml, 7.0 μg/ml, 8.0 μg/ml, 9.0 μg/ml, 10 μg/ml and incubated for about 30 minutes at room temperature in a moist chamber. The primary antibody may then be rinsed off with TBS/0.6% Tween 20®. The slides may e.g. then be gently drained and freed from any remaining wash solution. Immediately thereafter the secondary antibody for the detection of the inventive antibody may be added and incubated at room temperature for about 30 min. Secondary antibody dilution may e.g. be from about 1:100 to about 1:10.000, e.g. from about 1:100, 1:150, 1:200, 1:250, 1:300, 1:400, 1:500, 1:750, 1:1000 to about 1:1500, 1:2000, 1:2500, 1:3000, 1:3500, 1:4000, 1:5000, 1:5500, 1:6000, 1:7000, 1:8000, 1:9000, or e.g. from about 1:100, 1:150, 1:200, 1:250, 1:300, 1:400, 1:500, 1:750 to about 1:1.000, 1:2000. Secondary antibodies that can e.g. be used for the detection of bound antibody according to the invention may include polyclonal goat anti-rabbit HRP-conjugated immunoglobulins at a dilution of about 1:50, 1:175, to about 1:200, or e.g. goat anti-rabbit alkaline phosphatase (AP)-conjugated immunoglobulins at a dilution of about 1:20, 1:50, 1:100 to about 1:100, 1:200, 1:250, depending on the choice of the detection method and substrate employed, e.g. if Horseradish peroxidase (HRP)-conjugated secondary antibodies are used, 3,3'-diaminobenzidine (DAB) may e.g. be used for chromogenic detection, or e.g. 2,2'-azino-bis(3-ethylbenzothiazoline-6-sulphonic acid) (ABTS), or e.g. 3,3',5,5'-Tetramethylbenzidine (TMB) may be used, or if e.g. AP-conjugated secondary antibodies are used, a substrate combination of nitro blue tetrazolium chloride (NBT) and 5-bromo-4-chloro-3-indolyl phosphate (BCIP) may be used. General principles and guidelines on chromogenic immunohistochemstry can e.g. be found in Current Protocols in Immunology 21.4.21-21.4.26, November 2013.

The slides may then be washed twice with TBS/0.6% Tween 20® by overlaying the slide with wash solution for about 5 minutes after which the chromogen solution may be added according to the manufacturer's recommended protocol and incubated for about 4 to 5 min. A counterstain may e.g. be made using Harris' hematoxylin for about 5 minutes after which the slides may be rinsed under running tap water followed by e.g. an additional rinse in TBS/0.6% Tween 20 for about 1 min. The sections may then e.g. be dehydrated by gently immersing the slides up and down for several seconds in each solution before transferring to the next: 70% ethanol 90% ethanol 100% ethanol two times in xylene. The sections may then e.g. be mounted using a mounting medium and coverslip.

In one aspect the present invention provides for a method of detecting the presence or expression of an epitope comprised in SEQ ID NO:1 in a sample, e.g. an epitope comprised in any of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64. SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO, 106, SEQ ID NO: 107, SEQ ID NO: 108, wherein the method comprises the step of contacting a sample with an antibody or antigen binding fragment according to the invention, and detecting the presence of bound antibody or antigen binding fragment according to the invention. For example, the inventive method of detecting the presence or expression of an epitope comprised in SEQ ID NO:1 in a sample may comprise detection by means of immunohistochemstry, or by means of automated immunohistochemistry using commercially available IHC platforms, such as e.g. intelliPath FLX (Biocare Medical), WAVE RPD (Celerus Diagnostics), Omnis (DAKO), Autostainer Link 48 (DAKO), Benchmark XT (Ventana), or Benchmark Ultra (Ventana) according to the corresponding manufacturer's instructions and/or protocols. Accordingly, the inventive method may be used to detect the expression of human PD-L1 in a sample according to the invention.

In one embodiment the inventive method may be used to detect the presence of human PD-L1 or any fragment thereof comprising the amino acid sequence according to SEQ ID NO: 1 in a sample, wherein the method comprises the step of contacting said sample with the inventive antibody or antigen binding fragment thereof and detecting the presence of bound antibody or antigen binding fragment thereof as disclosed above, e.g. by means of means of immunohistochemstry, or by means of automated immunohistochemistry. For example, fragments of human PD-L1 according to the invention may comprise human PD-L1 which has been proteolytically cleaved, whereby the cleaved PD-L1 fragment comprises the amino acid sequence according to SEQ ID NO: 1. For example, a fragment of human PD-L1 according to the invention may comprise human PD-L1 lacking the extracellular domain, e.g. only comprises the transmembrane domain and the intracellular domain (e.g. amino acids 239-290 of GenBank accession no. AAH69381), or e.g. PD-L1 fragments which may be detected using the inventive antibody may only comprise the intracellular domain of human PD-L1 (e.g. amino acids 260-290).

In one aspect, the inventive antibody or antigen-binding fragment thereof is used to detect the presence or expression of an epitope comprised in SEQ ID NO:1 in a sample as disclosed above, e.g. an epitope comprised in any of SEQ ID NO: 19-SEQ ID NO: 108 as disclosed above. For example, the sample may be a biological sample, such as e.g. body fluid, or a blood sample. For example, the presence or expression of an epitope comprised in SEQ ID NO:1 in a blood sample may be done using the inventive antibody or antigen-binding fragment as disclosed above. The blood sample used may e.g. of mammalian origin, preferably a human blood sample, preferably a blood sample from a cancer patient, or from an individual at risk of having cancer. In one aspect the inventive antibody or antigen-binding fragment thereof may be used to e.g. detect the presence or expression of PD-L1 expression on circulating tumor cells, or e.g. leukocytes, such as neutrophils, eosinophils, basophils, lymphocytes or monocytes.

For example, using flow cytometry a peripheral blood sample (e.g. from a tumor patient, whereby the term "tumor" refers to neoplasms, i.e. abnormal growth of tissue which may also form a mass) may be analyzed using phycoerythrin-Texas Red (ECD)-conjugated anti-CD3, phycoerythrin-Cyanin 5 (PC5)-conjugated anti-CD15 (BD Biosciences, San Diego, Calif., USA), fluorescein isothiocyanate (FITC)-conjugated anti-CD80 (MIH clones, eBioscience, San Diego, Calif., USA) in conjunction with the inventive antibody or antigen-binding fragment thereof conjugated to phycoerythrin (PE) to identify the cell types expressing the epitope comprised in SEQ ID NO: 1. For example, neutrophils may be identified as $CD15^+CD3^-$ cells, the labeling of which may e.g. be done by incubating 50 μL of fresh heparinized whole blood simultaneously with 5 μL ECD-conjugated anti-CD3, 5 μL PC5-conjugated anti-CD15 on ice in the dark for 30 minutes. Cells incubated with PE- and FITC-conjugated mouse IgG may e.g. be used as isotype controls. The samples may then be analyzed using a cell sorter, e.g. a CYTOMICS FC 500 flow cytometer (Beckman Coulter Inc., Brea, Calif., USA) and associated software programs (CXP) according to the manufacturer's instructions.

The presence or expression of the epitope comprised in the amino acid sequence according to SEQ ID NO: 1, or e.g. comprised in any of the amino acid sequences according to SEQ ID NO: 19-SEQ ID NO: 108, on circulating tumor cells (CTCs) using the inventive antibody or antigen-binding fragment thereof as disclosed above may e.g. be analyzed by flow cytometry as disclosed above using one or more of the following markers EpCAM, EphB4, EGFR, CEA, HER2, or MUC-1 in combination with the inventive antibody as disclosed above, whereby the one or more antibodies used to label the CTCs has a different fluorescent label than the inventive antibody as disclosed above. CTCs may e.g. be isolated from a blood sample, e.g. a human blood sample as disclosed above, by commercially available isolation methods such as CellSearch, or a CTC Chip using e.g. ClearCell®FX CTC-based enrichment, e.g. according to the manufacturer's instructions. In the above methods, the inventive antibody or antigen-binding fragment thereof conjugated to a fluorescent probe or detectable label as disclosed above may e.g. be used in a concentration from about 0.01 μg/ml to about 50 μg/ml, e.g. from about 0.025 μg/ml, 0.05 μg/ml, 0.075 μg/ml, 0.1 mg/ml, 0.25 μg/ml, 0.5 μg/ml, 0.75 μg/ml, 1 μg/ml, 1.50 μg/ml, 1.75 μg/ml, 2 μg/ml, 2.5 μg/ml, 3 μg/ml, 3.5 μg/ml, 4 μg/ml, 4.5 μg/ml, 5 μg/ml, 5.5 μg/ml, 6 μg/ml, 7 μg/ml, 8 μg/ml, 9 μg/ml, 10 μg/ml to about 11 μg/ml, 12 μg/ml, 15 μg/ml, 17.5 μg/ml, 20 μg/ml, 22.5 μg/ml, 25 μg/ml, 30 μg/ml, 35 μg/ml, 37.5 μg/ml, 40 μg/ml, 45 μg/ml, 50 μg/ml, or e.g. from about 0.5 μg/ml, 0.75 μg/ml, 1 μg/ml, 1.50 μg/ml, 1.75 μg/ml, 2 μg/ml, 2.5 μg/ml, 3 μg/ml, 3.5 μg/ml, 4 μg/ml, 4.5 μg/ml, 5 μg/ml to about 6 μg/ml, 7 μg/ml, 8 μg/ml, 9 μg/ml, 10 μg/ml, or from about 0.5 μg/ml, 0.75 μg/ml to about 1 μg/ml, 1.50 μg/ml, 1.75 μg/ml, 2 μg/ml, 2.5 μg/ml, 3 μg/ml, 3.5 μg/ml, 4 μg/ml, 4.5 μg/ml, 5 μg/ml, 5.5 μg/ml, 6 μg/ml, 7 μg/ml, 8 μg/ml, 9 μg/ml, 10 μg/ml, or e.g. at a concentration of 0.5 μg/ml, 0.75 μg/ml, 1 μg/ml, 1.50 μg/ml, 1.75 μg/ml, 2 μg/ml, 2.5 μg/ml, 3 μg/ml, 3.5 μg/ml, 4 μg/ml, 4.5 μg/ml, 5 μg/ml, 5.5 μg/ml, 6 μg/ml, 7 μg/ml, 8 μg/ml, 9 μg/ml, 10 μg/ml.

For example, in one aspect of the invention the presence or expression of an epitope comprised in the amino acid sequence according to SEQ ID NO: 1, or e.g. in any of the amino acid sequences according to SEQ ID NO: 19-SEQ ID NO: 108, using the inventive antibody or antigen-binding fragment in a sample, such as a blood sample may be done by means of an ELISA. For example, the inventive antibody may be used at a concentration of about 0.25 μg/ml, 0.5 μg/ml, 0.75 μg/ml, 1 μg/ml, 1.50 μg/ml, 1.75 μg/ml, 2 μg/ml, 2.5 μg/ml, 3 μg/ml, 3.5 μg/ml, 4 μg/ml, 4.5 μg/ml, 5 μg/ml, 5.5 μg/ml, 6 μg/ml, 7 μg/ml, 8 μg/ml, 9 μg/ml, 10 μg/ml, or a control antibody (e.g. mIgG2a at 2 μg/ml in PBS) to coat an ELISA plate overnight at 4° C. followed by blocking with PBS containing 10% FBS. Blood samples (e.g. from a cancer patient, and/from healthy individual as control or reference sample) may e.g. be diluted in PBS at 1:1.000 in triplicate before adding to the plates. Subsequently, the wells may e.g. be washed six times in PBS with 0.1% Tween-20. Bound inventive antibody may be detected by horseradish peroxidase-conjugated secondary anti-rabbit IgG Ab at a 1:2.000 dilution incubated for 1.5 hour at room temperature and then reacted with tetramethylbenzidine followed by a measuring absorbance using a plate reader at a wavelength of 450 nm. Nonspecific binding of sera to plates coated with control Ig may e.g. be subtracted from the measurement of each sample for background correction.

According to a preferred embodiment the inventive antibody or antigen-binding fragment thereof may be used to detect the presence or expression of an epitope comprised in SEQ ID NO: 1, or e.g. in any of the amino acid sequences according to SEQ ID NO: 19-SEQ ID NO: 108, in a tissue sample, fixed tissue sample, or a formaldehyde-fixed paraffin-embedded (FFPE) tissue as disclosed above. Preferably, according to one embodiment the formaldehyde-fixed paraffin-embedded (FFPE) tissue is a tumor tissue sample, or a tumor tissue-derived sample, e.g. tumor cells, cultured tumor cell lines, or tumor tissue which has been cultured as disclosed above. The inventive method may e.g. in one embodiment also comprise subjecting control tissue which does not express or only minor amounts of PD-L1 to the inventive method, preferably processed in parallel to the tissue sample as disclosed above. For example, the control tissue may comprise thyroid tissue or skeletal muscle tissue, or cultured PD-L1 negative cancer cells, such as e.g. A2780, Colo205 or IGROV-1. The term minor amounts as used above refers to the expression of PD-L1 by a tumor cell or tumor tissue which is at least 5-, 10-, 20-, 25-, 40-, 50-, or 100-fold less than that of a PD-L1 positive tumor tissue or tumor cell (such as e.g. Hs746T, MDA-MB 231, NCI-H2009, human spleen) when compared by semiquantitative immunoblotting, or qPCR as described in e.g. Journal of Immunological Methods 345 (2009) 40-48; Journal of Immunological Methods 353 (2010) 148-150; Hematology. 2016 Mar. 31:1-6. For example, the tissue sample, or tumor tissue sample as defined above may be subjected to RNA isolation and cDNA synthesis which may then e.g. be used in qPCR to determine the relative expression level of PD-L1.

In one aspect the inventive antibody may e.g. be used on tissue samples mounted on a glass slide to form a tissue array in which different tumor tissue samples may be placed next to each other. For example, a tissue array comprises at least one, two, three or four sections of each tissue sample mounted on a glass slide in different locations (e.g. to avoid detection artefacts). For example, the tissue array may comprise at least 4, 5, 6, 7, 8, 9, 10, 11, 12, 14, 16, 18, 20 to about 22, 24, 26, 28, 30, 32, 34, 36, 38, 40, 42, 44, 46, 48, 50, 55 or 60, or form about 22, 24, 28, 30, 36, 40, 44, 48, 52, 56, 60 to about 64, 68, 72, 76, 78, 80, 82, 84, 86, 90, 100 different tissue samples. For example, in one embodiment the tissue array may comprise at least one or more, e.g. 5, 10, 20, 30, 40, 50 or more, or e.g. all of the cancer cell lines ZR-75-1, WM164, U-87MG, U-118MG, T47D, SW707, SW620, SNB-78, NCI-H69, NCI-H569, NCI-H460, NCI-H292, NCI-H2009, NCI-H1975, Mx-1, MeWo, PC-3, Raji, Ramos, suit7, MDA-MB-468, MDA-MB-435, MDA-MB-231, MCF7, M24met, Lox, LoVo, Kyse 30, Jurkat, IGROV-1, HT29, Hs746T, Hs68, HL60, FaDu, EBC-1, DU 145, DLD-1, COLO 205, Calu 6, Calu 3, BT474, AGS, A549, A-431, A2780, Pfeiffer, MiaPaCa-2, ME-SA, in addition to the tumor tissue sample as disclosed above. The cancer cell lines as disclosed above may e.g. be obtained from ATCC, or e.g. DSMZ (Leipniz Institute DSMZ) and cultured according to established methods for each of the respective cell lines. Tissue arrays or tumor tissue arrays comprising at least one formaldehyde-fixed paraffin-embedded (FFPE) tissue sample, or FFPE tumor tissue sample as disclosed above may e.g. be manufactured according to the protocol as described in Nat Med. 1998 Jul.; 4(7):844-7.

According to one embodiment, the formaldehyde-fixed paraffin-embedded (FFPE) tissue sample, or formaldehyde-fixed paraffin-embedded tumor tissue sample is derived from a subject being at risk of, or having cancer, T cell dysfunction, acute or chronic infection or showing tumor immunity. The term cancer as used for the inventive method refers to or describes the physiological condition in mammals, preferably in humans, that is typically characterized by unregulated cell growth/proliferation with the potential to invade or spread to other parts of the body. Examples of cancer include, but are not limited to, non-small-cell lung cancer (NSCLC), mesothelioma, unresectable mesothelioma, breast cancer, adenocarcinoma of stomach or GEJ, gastric, Thymoma, ovarian cancer, adenoid cystic carcinoma, metastatic adenoid cystic carcinoma, bladder cancer, clear cell kidney cancer, head/neck squamous cell carcinoma, lung squamous cell carcinoma, malignant melanoma, ovarian cancer, pancreatic cancer, prostate cancer, renal cell cancer, small-cell lung cancer (SCLC) or triple negative breast cancer, lymphoproliferative disorders, acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL), Merkel cell carcinoma (MCC), or squamous head and neck cancer (SHNC). The above cancer types may e.g. also be referred to as malignancy. The term "T cell dysfunction" as used for the inventive method as disclosed above refers to a pathological state of CD8 T cells that e.g. can be caused if alterations in the tightly controlled differentiation process of a CD8 positive T cell occurs, such as e.g. changes in the nature, context and duration of antigen encounter which can result in substantial alterations in T cell activation and differentiation process that may also be referred to as T-cell exhaustion, tolerance, anergy or senescence. The term acute infection as used for the inventive method refers to an acute infection caused by bacteria, viruses or parasites and which e.g. has occurred about one, two, three, or four weeks prior to diagnosis. The term "chronic infection" as used for the inventive method refers to a situation in which pathogens are not quickly eliminated but rather persist for an extended period of time, e.g. for more than three, four, five, six, seven, eight, nine or ten weeks. The persistent pathogen exposure can result in chronic antigen stimulation and persistent inflammation which can result in exhaustion and/or clonal depletion of pathogen-specific CD8 T cells. Chronic infections may e.g. include viral infection such as hepatitis A, hepatitis C or hepatitis D, HIV infections, or e.g. infections with neisseria meningitidis, neisseria gonorrhoeae, bartonella henselae, Borrelia burgdorferi, salmonella species, *brucella* species *campylobacter* species, mycobacteria species, *treponema pallidum*, or *coxiella burnetii*, if left untreated. In one embodiment the FFPE tissue sample, or FFPE tumor tissue sample is derived from a subject, e.g. a human, characterized by or having tumor immunity. The term "tumor immunity" as used for the inventive method refers to the process in which tumors evade immune recognition and clearance. Tumor-derived, or tumor-associated factors are believed to influence dendritic cell differentiation and preclude the development of cells with antigen-presenting function that ultimately result in tumor immunity. The expression of endogenous retroviruses (ERVs) in particular tumor-specific endogenous retroviruses (TERVs) has e.g. also been implicated in tumor immunity. Other factors that may contribute to tumor immunity are e.g. gene amplifications PD-L1 (CD274) and ALOX12B/15B, or e.g. mutations on any of the genes B2M, HLA-A, HLA-B, HLA-C, or CASP8 that result in a loss of antigen presentation (e.g. of tumor associated neoantigens), or result in blockage of extrinsic apoptosis.

In one aspect the present invention provides for a method of predicting that a mammal, preferably a human, suffering from a malignancy is a likely candidate for treatment with an immune check-point inhibitor, such as e.g. an anti-PD-L1 antibody, or an anti-PD-1 antibody which comprises detecting the presence or absence of an epitope comprised in SEQ NO: 1, or e.g. comprised in any of SEQ ID NO: 19-SEQ ID NO: 108, e.g. SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, in a sample derived from a mammal, e.g. from an individual in need thereof, e.g. a human, having or at risk of cancer, T cell dysfunction, acute or chronic infection or tumor immunity, or e.g. a cancer patient suffering from a malignancy, whereby the method comprises e.g. flow cytometry, FACS, or preferably immunohistochemistry using the inventive antibody, wherein detecting the epitope comprised in SEQ ID NO: 1, or e.g. comprised in any of SEQ ID NO: 19 to SEQ ID NO: 108, in e.g. more than about 0.25%, 0.5%, 0.75%, 1%, 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10.0%, or in about 0.5% 0.75%, 1%, 1.5%, 2.0%, 2.5%, 3.0%, 3.5%, 4.0%, 4.5%, 5.0%, 6.0%, 6.5%, 7.0%, 7.5%, 8.0%, 8.5%, 9%, 9.5%, 10%, 10.5%, 11%, 12%, 13%, 14%, 15% to less than about 50%, 55%, 60%, 65%, 70%, 75%, 80%, 85%, 90%, 95%, or e.g. from about 20%, 25%, 30%, 35%, 40%, 45% to less than about 65%, 70%, 75%, 80%, 85%, 90%, 95%, or from about 0.25%, 0.5%, 0.75%, 1% to less than about 1.5%, 2.0%, 2.5%, 3.0%, 3.5%, 4.0%, 4.5%, 5.0%, 6.0%, 6.5%, 7.0%, 7.5%, 8.0%, 8.5%, 9.0%, 9.5%, or 10.0%, or from about 0.25% to less than about 0.5%, 0.75%, 1% of the cells in the sample indicates that the patient is likely to respond to a treatment with an immune checkpoint-inhibitor, e.g. to a treatment with an anti-PD-L1 antibody, or to a treatment with an anti-PD-1 antibody. The term "immune checkpoint inhibitor", as used herein has its general meaning in the art and refers to a molecule that is expressed by T cells in that either turn up a signal (stimulatory checkpoint molecules) or turn down a signal (inhibitory checkpoint molecules), such as for example the PD-1/PD-L1 and CTLA-4/CD28 signaling pathways both of which are recognized in the art to constitute immune checkpoint pathways (see e.g. Pardoll, 2012. Nature Rev Cancer 12:252-264). Anti-PD-L1 antibodies that may e.g. be administered to patients that have been identified as likely candidates for the treatment with an immune checkpoint inhibitor using the inventive method as disclosed above include e.g. avelumab, durvalumab, atezolizumab, or e.g. anti-PD-1 antibodies such as pembrolizumab, nivolumab, or Pf-06801591.

PD-L1 positive cells in the sample according to the invention may e.g. include tumor cells, or immune cells, such as tumor infiltrating lymphocytes (TILs) (e.g. CD8-positive T cells, macrophages, NK cells, or B-cells). For example, depending on the tumor type from which the FFPE tumor tissue sample as disclosed above was obtained or derived, different methods for determining the relative abundance of PD-L1 positive cells in a sample (scoring method) may be used. For example, using immunohistochemistry (IHC) as disclosed above using the inventive antibody to detect PD-L1 positive cells, PD-L1 scoring may include determining the relative abundance of PD-L1 positive tumor cells, or the relative abundance of PD-L1 positive TILs in the sample, or e.g. determining the combined relative abundance of PD-L1 positive tumor cells and TILs. The total number of cells in the sample, or any subfraction thereof which is used for determining the number of PD-L1 positive cells, may e.g. be obtained by counterstaining the sample using hematoxylin to visualize cell nuclei and cytoplasms, or e.g. using a 4',6-Diamidino-2-phenylindole (DAPI) stain to visualize cell nuclei if fluorescent detection methods are used. The term "PD-L1 positive cells" as used for the inventive method refers to cells which detectably express an epitope comprised in the amino acid sequence according to SEQ ID NO: 1 to which the inventive antibody specifically binds and which then may be detected with e.g. HRP- or AP-coupled secondary antibodies which specifically bind to the inventive antibody and allow chromogenic or fluorescent detection when reacted with the corresponding substrate (e.g. as disclosed above). For example, HRP-coupled secondary antibodies may be used and incubated with DAB as substrate to label PD-L1 positive cells. The scoring of PD-L1 positive cells may e.g. include counting individual cells or nuclei, to determine the number of PD-L1 positive cells and total cell number in the FFPE tumor tissue sample analyzed (or e.g. in any subsection thereof). Alternatively, the surface area of PD-L1 positive cells and hematoxylin stained cells may e.g. be used to determine the relative abundance of PD-L1 positive cells.

In one aspect the inventive method as disclosed above may be used to identify likely candidates for a treatment with an anti-PD-L1 antibody whereby the malignancy according to the invention may be one of non-small-cell lung cancer (NSCLC), mesothelioma, unresectable mesothelioma, breast cancer, adenocarcinoma of stomach or GEJ, gastric, Thymoma, ovarian cancer, adenoid cystic carcinoma, metastatic adenoid cystic carcinoma, bladder cancer, clear cell kidney cancer, head/neck squamous cell carcinoma, lung squamous cell carcinoma, malignant melanoma, ovarian cancer, pancreatic cancer, prostate cancer, renal cell cancer, small-cell lung cancer (SCLC) or triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL), Merkel cell carcinoma (MCC), or squamous head and neck cancer (SHNC).

According to one aspect of the present invention the inventive method may be used to identify or predict likely candidates (e.g. cancer patients who will respond to a treatment with an immune checkpoint inhibitor, such as an anti-PD-L1 antibody, or anti-PD-1 antibody with one of the following anti-PD-L1 antibodies avelumab, atezolizumab, durvalumab, LY300054, BMS-936559, or anti-PD-1 antibodies pembrolizumab, nivolumab, or Pf-06801591. For example, if an individual in need thereof, e.g. a human cancer patient, or e.g. a human patient suffering from a malignancy as disclosed above, or a human at risk of having cancer, by applying the above inventive method is found to be a likely candidate for the treatment with an anti-PD-L1 antibody, e.g. one of avelumab, atezolizumab, durvalumab, LY300054, BMS-936559, or with an anti-PD-1 antibody, e.g. one of pembrolizumab, nivolumab, or Pf-06801591 may be administered alone or in combination with other anticancer agents in a dose from about 0.1 mg/kg to about 50 mg/kg, from about 0.5 mg/kg, 0.75 mg/kg, 1 mg/kg, 1.5 mg/kg, 2.5 mg/kg, 5 mg/kg, 7.5 mg/kg, 10 mg/kg, to about 12.5 mg/kg, 15 mg/kg, 17.5 mg/kg, 20 mg/kg, 25 mg/kg, 27.5 mg/kg, 30 mg/kg, 35 mg/kg, 37.5 mg/kg, 40 mg/kg, 42.5 mg/kg, 45 mg/kg, or e.g. 1 mg/kg, 2.5 mg/kg, 5 mg/kg, 7.5 mg/kg, 10 mg/kg, 12.5 mg/kg, 15 mg/kg, 17.5 mg/kg, 20 mg/kg, 22.5 mg/kg, 25 mg/kg, 30 mg/kg, 35 mg/kg. In one embodiment the anti-PD-L1 antibodies avelumab, atezolizumab, durvalumab, or e.g. the anti PD-1 antibodies pembrolizumab, nivolumab, or Pf-06801591 may e.g. be administered to likely candidates which have been identified by applying the inventive method as disclosed above in a flat dosing regimen, e.g. avelumab may be administered at flat dosing regimen of 500-800 mg every week, e.g. from about 600 mg-750 mg every week, or e.g. from about 650-850 mg every week, or e.g. from about 700-900 mg every week, or e.g. 525 mg every week, 550 mg every week, 600 mg every week, 625 mg every week, 650 mg every week, 700 mg every week, 725 mg every week, 750 mg every week, or e.g. from about 900 to about 1600 mg every two weeks, e.g. from about 1000 mg to about 1500 mg every two weeks (q2w), or from about 1250 mg to about 1400 mg q2w, or from about 1000 mg q2w to about 1250 mg q2w, e.g. 925 mg q2w, 950 mg q2w, 1000 mg q2w, 1125 mg q2w, 1200 mg q2w, 1250 mg q2w, 1300 mg q2w, 1350 mg q2w, 1400 mg q2w, 1450 mg q2w, 1500 mg q2w, 1550 mg q2w, or e.g. from about 1250-2400 mg every three weeks (q3w), or from about 1500 mg to about 2250 mg q3w, or from about 1750 mg to about 2000 mg q3w, or from about 1800 mg to about 2300 mg q3w, or from about 1250 mg to about 1750 mg q3w, or from about 1300 mg to about 1500 mg q3w, or e.g. 150 mg q3w, 1350 mg q3w, 1450 mg q3w, 1550 mg q3w, 1650 mg q3w, 1750 mg q3w, 1800 mg q3w, 1850 mg q3w, 1900 mg q3w, 1950 mg q3w, 2000 mg q3w, 2125 mg q3w, 2250 mg q3w, 2350 mg q3w. The term "mg/kg" as used above refers to milligrams of anti-PD-L1 or anti-PD-1 antibody per kilogram body weight of a patient that will be subject to treatment with the respective antibody. The terms "q2w" and "q3w" as used herein shall indicate an administration every two weeks, or every three weeks. The term "mg/kg" as used above refers to milligrams of anti-PD-L1 (or e.g. anti-PD-1) antibody per kilogram body weight.

According to one aspect the present invention pertains to the use of the inventive antibody or antigen binding fragment thereof in the inventive method for predicting that a patient suffering from a malignancy is a likely candidate for treatment with an anti-PD-L1 antibody, or anti-PD-1 antibody. For example, the inventive antibody or antigen-binding fragment may be used in immunohistochemistry to detect PD-L1 expression in the FFPE tumor tissue sample and subsequently subjecting the sample to visual assessment of PD-L1 expression (scoring) to determine the number of PD-L1 positive cells, e.g. tumor cells, or TILs as disclosed above. The inventive antibody or antigen-binding fragment thereof may e.g. also be used in dual-color immunofluorescence to label TILs. For example dual color fluorescence may include the inventive antibody and one of an anti-CD8 antibody, anti-CD163 antibody, anti-CD3 antibody, anti-CD11c antibody, anti-CD56 antibody, anti-CD68 antibody, anti-Granzyme B antibody, or anti-FoxP3 antibody, whereby the antibodies are derived from different species to allow detection of both, the inventive antibody and of the TIL-specific antibody. Dual immunofluorescence may e.g. be carried out utilizing commercial kits, such as Novocastra PowerVision Poly-HRP IHC detection system and subsequent use of Alexa Fluor 594-, or Alexa Fluor 488 Tyramide Signal Amplification (TSA) Kit according to the manufacturer's instructions. The scoring of PD-L1 positive cells may e.g. be done as disclosed above, or may e.g. include assigning IHC scores based on PD-L1 positive tumor cells, PD-L1 positive immune cells (e.g. TILs, macrophages), or the aggregate score of PD-L1 positive tumor and immune cells e.g. with IHC scores of 0, 1, 2, or 3 corresponding to <1% PD-L1 positive cells (IHC score of 0), >1%, but <5% (IHC score of 1), >5%, but <10% (IHC score of 2), or >10% (IHC score of 3). For example, if more than one sample of a given patient is subjected to the inventive in vitro method as disclosed above using the inventive anti-PD-L1 antibody as disclosed above, the IHC score may be the average score of the samples analyzed, or e.g. the IHC score may correspond to the IHC score of the sample that has the highest IHC score. The IHC score may e.g. also be determined by scoring both tumor cells expressing PD-L1 using the inventive antibody or antigen-binding fragment thereof as a percentage of total tumor cells and tumor-infiltrating immune cells expressing PD-L1 as a percentage of tumor area. Samples may e.g. be scored 3 if >50% tumor cells were PD-L1 positive; score 2 if >5% but <50% tumor cells were PD-L1 positive; score 1 if >1% but <5% of tumor cells were PD-L1 positive; and score 0 if <1% tumor cells expressed PD-L1.

In one embodiment the present invention provides for a method of treatment of cancer in a patient who has been identified as a likely candidate to respond to the treatment with an immune checkpoint inhibitor by applying the inventive method as disclosed above to a sample obtained or derived from said patient and determining PD-L1 expression in that sample and in a second step comparing the expression of PD-L1 in that sample to the PD-L1 expression in a reference sample, and in a third step administering an immune checkpoint inhibitor, such as an anti-PD-L1, or anti-PD-1 antibody to said patient if the PD-L1 expression in the sample of said patient is found to be increased or above a certain threshold. The term "threshold" as used in the inventive method of treatment e.g. refers to a relative abundance of PD-L1 expression in the patient-derived sample compared to that of the reference sample as determined by the inventive method as disclosed above. For example, the threshold may be defined as the relative increase in PD-L1 positive cells in the patient sample compared to the reference sample, or e.g. may be defined as an absolute or relative number of PD-L1 positive cells in said sample, e.g. 0.5%, 1%, 2%, 3%, 4%, 5%, 10%, 15%, 20%, 25%, 40%, 50%, 75%, 80%, >1%, >5%, >10%, >20%, >50%, >75%, >80% of the cells in the sample, or e.g. the threshold may be based on IHC score or scoring method as disclosed above. The reference sample used in the inventive method of treatment may e.g. be derived from a healthy donor who is not inflicted with cancer and which is subjected to the same method of detection of PD-L1 expression using the inventive antibody or antigen-binding fragment as disclosed above, such as e.g. IHC on FFPE tissue samples. For example, the reference sample may be obtained from the corresponding tissue and location as the sample obtained from the patient and is preferably processed in parallel to the sample from said patient. The reference sample may e.g. may also be derived from the same tissue or organ as the tumor tissue sample if it is obtained from an area or location that is not diseased, or e.g. the reference sample may be derived from a contralateral healthy organ. Anti-PD-L1 that may e.g. be administered to a patient according to the inventive method of treatment include avelumab, atezolizumab, durvalumab, or e.g. anti-PD-1 antibodies such as pembrolizumab, nivolumab, or Pf-06801591. In the inventive method of treatment the anti-PD-L1 or anti-PD-1 antibodies, such as e.g. avelumab, are administered as disclosed above, e.g. in a dose of from about 5 mg/kg to about 30 mg/kg, or e.g. in a dose of 5 mg/kg, 7.5 mg/kg, 10 mg/kg, to about 12.5 mg/kg, 15 mg/kg, 17.5 mg/kg, 20 mg/kg, 25 mg/kg, 27.5 mg/kg, 30 mg/kg, whereby the antibody is administered once a week (q1w). The anti-PD-L1 antibody (e.g. avelumab) may also be administered as a flat dose every week, or every second week, or every three weeks as disclosed above, e.g. in a flat dose of 500-800 mg every week, or 900-1600 mg every two weeks, or 1250-2400 mg every three weeks.

In one embodiment the present invention provides an isolated polynucleotide encoding the antibody or antigen binding fragment thereof. The term "isolated polynucleotide" as used for the present invention refers to a polynucleotide which is at least 70%, 75%, 80%, 85%, 90%, 95%, 96%, 97%, 98%, 99% pure and free of contaminants, such as e.g. proteins and/or lipids. The inventive antibody or antigen-binding fragment thereof may e.g. be encoded by two isolated polynucleotides encoding the light chain and the heavy chain of the inventive antibody. The isolated polynucleotides may e.g. comprise one polynucleotide sequence according to SEQ ID NO: 17 encoding the light chain of the inventive antibody and one polynucleotide comprising the polynucleotide sequence according to SEQ ID NO: 18 encoding the heavy chain of the inventive antibody. Depending on the expression system used the polynucleotide sequences according to SEQ ID NO: 17 and SEQ ID NO: 18 may be codon optimized to allow for a better expression of the inventive polynucleotides resulting in higher yields of the inventive antibody in a respective expression system. Codon optimization may e.g. be done using available codon usage tables as published in Nucleic Acids Res. 1988 Mar. 11; 16(5):1715-28, Nucleic Acids Res. 1988 Sep. 12; 16(17):8207-11; Methods Cell Biol. 1991; 36:675-7; or e.g. available computer-embedded codon optimization tools such as those published in e.g. Bioinformatics. 2014 Aug. 1; 30(15):2210-2. Codon optimization of the at least one inventive polynucleotide may be done may in consideration of the respective expression system used, such as e.g. murine or human cell lines, yeast or insect cell lines.

In one embodiment the present invention provides for an expression vector comprising the inventive polynucleotide as disclosed above. The term "expression vector" according to the invention refers to nucleic acid vector that comprises a gene expression control sequence, such as e.g. a promoter or promoter component, operably linked in 5' to 3' direction to a nucleotide sequence encoding at least one polypeptide, e.g. SEQ ID NO: 17 and/or SEQ ID NO: 18. For example, the expression vector according to the invention may comprise the polynucleotide according to SEQ ID NO: 17, or SEQ ID NO: 18, or may comprise both polynucleotides according to SEQ ID NO: 17 and SEQ ID NO: 18. Nucleic acid sequences necessary for expression in prokaryotes include a promoter, a ribosome binding site, optionally an operator sequence and possibly other sequences. Eukaryotic cells utilize promoters, such as e.g. a CMV promoter, SV40 promoter, EF1a, or CAG promoter and often enhancers and polyadenlyation signals. Exemplary mammalian expression vectors are pCMV, pCMV-SPORT, pcDNA, or e.g. the plasmid-based multigene expression system as described in Nat Commun. 2010 Nov. 16; 1:120, or e.g. if viral expression of the inventive antibody or antigen-binding fragment thereof is intended, µLKO.1-hygro, pBABE-hygro, pBABE-puro, pBABE-zeo, µLenti CMV/TO zeo DEST, pCW57.1. Optionally, the expression vector in eukaryotes may comprise an internal ribosomal entry site (IRES) between the inventive polynucleotide sequences providing for a bicistronic expression construct to allow expression of both polynucleotides according to SEQ ID NO: 17 and SEQ IS NO: 18 from one expression vector. IRES sequences that e.g. may be used may include those published in PLoS One. 2013 Dec. 9; 8(12):e82100, e.g. 5' AUGAUAAUAUGGC-CACAACCAUG. Suitable expression vectors that may e.g. be used for the expression of the inventive polynucleotides may comprise pCMV-based expression vectors, or pD912-based vectors and variants thereof, Gateway® expression vectors, pcDNA-based expression vectors, or pJΩ vectors (see e.g. Nucleic Acids Research, Vol. 18, No. 4), or vectors which may be used for retroviral or lentiviral production (see e.g. Front Biosci. 1999 Jun. 1; 4:D481-96). Suitable yeast expression vectors may e.g. utilize GAL4, PGK, ADH1, ADE2 or TRP1 promoters for the expression of the inventive polynucleotides, e.g. expression vectors pRS420, µLEX, pACT2.2, pTEF1/zeo, pAG425GDP-ccdb, pBEVY-T, pAG300, pGBK T7, pEZY202, pCETT, pRG201, pXP120, pXP320, p2GLex, or p426 GAL. For example, the inventive polynucleotides as disclosed above may e.g. also be expressed in insect cells using expression vectors comprising a polyhedrin promoter such as e.g. pFastBac, pFast-Bac DUAL, pVL 1392, pVL 1393, or AcNPV for use in baculoviral expression of the inventive polynucleotides. In a preferred aspect the expression vector comprising the inventive polynucleotide is a mammalian expression vector.

In one embodiment the present invention pertains to the use of an expression vector according to the invention in producing the inventive antibody comprising the amino acid sequences according to SEQ ID NO: 15 and SEQ ID NO: 16. For example, the at least on vector according to the invention which comprises polynucleotides encoding the amino acid sequences according to SEQ ID NO: 15 and SEQ ID NO: 16 may be used in a transient expression system to express the inventive antibody. For example the transient expression system as disclosed in Methods. 2014 Jan. 1; 65(1):5-10 may be used. The inventive expression vector or at least one expression vector according to the invention may e.g. also be used for the generation of stable cell lines expressing the inventive antibody. For example, the process for development of a stable cell line may e.g. begin with transfection of a suitable host cell with the inventive expression vector, or with at least one expression vectors of the invention, e.g. two expression vectors, of which a first vector comprises the polynucleotides according to SEQ ID NO: 17 and a second expression vector comprises the polynucleotides according to SEQ ID NO:18. Following transfection with expression vectors comprising the polynucleotides encoding the antibody light and heavy chains, as well as at least one selectable marker, transfected cells may be incubated at suitable growth conditions for 24h-72h to allow expression of the inventive antibody, and screening for cells that have high productivity of the inventive antibody following growth recovery, serum-free suspension adaptation and amplification and clone selection.

For example, the inventive expression vector, or e.g. the at least one expression vector of the invention comprising the polynucleotides according to SEQ ID NO:17 and/or SEQ ID NO: 18 may be used to produce or manufacture the inventive antibody as disclosed above. For example, the expression vector comprising the inventive polynucleotides comprising the sequences according to SEQ ID NO:17 and/or SEQ ID NO:18 may be used to transfect at least one suitable host cell for the expression of the inventive antibody as disclosed above. For example, the inventive polynucleotides according to SEQ ID NO:17 and SEQ ID NO:18 may be comprised in one expression vector, or e.g. may be comprised in two separate expression vectors that together are used in the production of the inventive antibody.

Polynucleotides comprising the nucleotide sequences according to SEQ ID NO: 17 and SEQ ID NO:18 may e.g. be used in retroviral, or lentiviral vectors to transduce at least one suitable host cell for the expression of the inventive polynucleotides.

For example, for the manufacture or production of the inventive antibody the polynucleotide encoding the light chain amino acid sequence according to SEQ ID NO:15 and the polynucleotide encoding the heavy chain amino acid sequence according to SEQ ID NO:16 may be comprised on two separate expression vectors, such that both of the expression vectors have to be transfected into a suitable host cell for the production or manufacture of the inventive antibody. The transfection method used may e.g. depend on the host cell line utilized. A variety of transfection methods have been developed to stably introduce vector DNA into mammalian cells, including e.g. calcium phosphate, electroporation, cationic lipid-based lipofection, and polymer or dendrimer-based methods. In one example, the inventive expression vector, or the at least one expression vector according to the invention may be used in recombinase-mediated cassette exchange (RMCE) using CHOK1SV cells to generate stable cell lines for the manufacture of the inventive antibody, e.g. according to the method described in Biotechnol Prog. 2015 Nov.-Dec.; 31(6):1645-56.

According to on embodiment the present invention provides a host cell which comprises at least one expression vector as disclosed above. For example, the host cell according to the invention may comprise at least one expression vector as disclosed above which encodes the inventive antibody comprising the amino acid sequences according to SEQ ID NO: 17 and SEQ ID NO:18, e.g. the host cell may comprise one expression vector as disclosed above encoding the amino acid sequence according to SEQ ID NO: 17 and a second expression vector as disclosed above which encodes the amino acid sequence according to SEQ ID NO: 18. The expression vectors may comprise selectable markers, e.g. antibiotic resistance genes, such as e.g. G418, zeocin, blasticidin, hygromycin B, mycophenolic acid, or puromycin. The inventive antibody may e.g. also be encoded by more than one expression vector of the invention, each of may comprise a different selectable marker to allow the selection of host cells which have been transfected with at least one of each of the expression vectors. For example, a first expression vector if the invention comprising the polynucleotide according to SEQ ID NO: 17 may comprise a neoR gene and a second inventive expression vector may comprise bsd gene which confers resistance against blasticidin. Accordingly, a host cell which comprises both expression vectors of the invention will confer resistance to G418 and blasticidine and may be selected in growth medium containing both antibiotics. In one aspect the host cell according to the invention may comprise the inventive polynucleotides as disclosed above stably integrated into the host cell genome, e.g. by viral transduction of the polynucleotides according to SEQ ID NO:15 and SEQ ID NO:16 including at least one, two or more selectable markers. For example, in one aspect the host cell according to the invention may comprise the inventive polynucleotides according to SEQ ID NO: 15 and SEQ ID NO:16 as episomes, e.g. with at least one, two different selectable markers.

For example, the host cell according to the invention may be a bacterial cell, insect cell, yeast cell or mammalian cell. For example, a host cell according to the invention comprising at least one inventive polynucleotide or an expression vector according to the invention as disclosed above refers to any type of cell that can contain the vector according to the invention. The host cell can be a eukaryotic cell, e.g., plant, animal, fungi, or algae (e.g. *Phaeodactylum tricornutum, Chlamydomonas reinhardtii*) or can be a prokaryotic cell, e.g., bacteria or protozoa. The host cell can be a cultured cell or a primary cell, i.e., isolated directly from an organism, e.g., a human. The host cell may e.g. be an adherent cell or a suspended cell, i.e., a cell that grows in suspension. A host cell according to the invention may e.g. include *Saccharomyces cerevisiae, Hansenula polymorpha, Schizosaccharomyces pombe, Schwanniomyces occidentalis, Kluyveromyceslactis, Yarrowia lipolytica* and *Pichia pastoris*, or e.g. Sf9, Sf21, S2, Hi5, or BTI-TN-5B1-4 cells, or e.g. DH5α *E. coli*. Preferably, the host cell according to the invention is one of HEK293, HEK293T, HEK293E, HEK 293F, NS0, per.C6, MCF-7, HeLa, Cos-1, Cos-7, PC-12, 3T3, Vero, vero-76, PC3, U87, SAOS-2, LNCAP, DU145, A431, A549, B35, H1299, HUVEC, Jurkat, MDA-MB-231, MDA-MB-468, MDA-MB-435, Caco-2, CHO, CHO-K1, CHO-B11, CHO-DG44, BHK, AGE1.HN, Namalwa, WI-38, MRC-5, HepG2, L-929, RAB-9, SIRC, RK13, 11611, 1D3, 2.4G2, A-10, B-35, C-6, F4/80, IEC-18, L2, MH1C1, NRK, NRK-49F, NRK-52E, RMC, CV-1, BT, MDBK, CPAE, MDCK.1, or MDCK.2, D-17.

According to one embodiment the present invention provides for the use of a host cell of the invention as disclosed above in the manufacture of the inventive antibody, e.g. the inventive antibody comprising the amino acid sequences according to SEQ ID NO: 15 (light chain) and SEQ ID NO:16 (heavy chain). For example, the use of a host cell according to invention in the manufacture of the inventive antibody may comprise culturing at least one host cell comprising at least one expression vector or polynucleotide of the invention comprising the polynucleotide sequences according to SEQ ID NO: 15 and/or SEQ ID NO:16 under suitable conditions that allow the expression of the inventive antibody. In one example, the at least one host cell of the invention comprises the polynucleotides according to SEQ ID NO: 17 and SEQ ID NO: 18 including regulatory sequences required for the expression of the polynucleotides, stably integrated into the host cell's genome.

For example, the at least one host cell of the invention, e.g. at least $10^2$, $10^3$, $10^4$, $10^5$, $10^6$, $10^7$, $10^8$, $10^9$ cells, may be allowed to grow in DMEM containing 10% FBS at 37° C. in a 10% $CO_2$ atmosphere or e.g. in serum-free culture medium to aid in the subsequent isolation and purification such as e.g. FreeStyle™ 293 expression medium, or OptiCHO™ medium. For example, Grace's insect medium, express Five® SFM (Life Technologies), or High Five® medium (Life Technologies) may be used if the at least one host cells of the invention is an insect cell as disclosed above, or YNM medium, YPD broth, or e.g. PichiaPink (Life technologies) if the at least one host cells of the invention is a yeast cell. For example, suitable growth conditions may comprise allowing the at least one host cell of the invention to grow between 12-408 h, e.g. for about 12 to about 400 h, e.g. between 14 h, 16 h, 18 h, 20 h, 24 h, 36 h, 48 h, 72 h, 96h to about 120 h, 144 h, 168 h, 192, 216 h, 240 h, 264 h, 288 h, 312 h, 336 h, 360 h, 384 h, 408 h. Subsequently, the inventive antibody or antigen binding fragment as disclosed above may be isolated and purified. For example, the antibody or antigen-binding fragment of the invention may be purified and isolated by chromatography, e.g. ion-exchange chromatography, size-exclusion chromatography, ammonium sulfate precipitation, ultrafiltration, or purified using protein A sepharose, e.g. as described in Current Protocols in Molecular Biology (1997) 11.11.1-11.11.5.

EXAMPLES

The following Examples are intended to further illustrate the invention. They are not intended to limit the subject matter or scope of the invention thereto.

Example 1—Antibody Generation

The inventive monoclonal rabbit antibody directed against a KLH-coupled carboxyterminal peptide of PD-L1 (SEQ ID NO: 1, RLRKGRMMDVKKCGIQDTNSKKQS-DTHLEET) was generated using the same basic principal for making monoclonal antibodies as for mouse monoclonal antibodies. In brief, the generation of the inventive rabbit monoclonal antibody followed a four-step procedure:
1) Immunization of rabbits and screening of polyclonal sera,
2) Fusion to generate hybridoma cells and screening of supernatants of multiclones.
3) C. Subcloning and screening of supernatants of subclones.
4) Cloning and production of recombinant antibody in HEK-293 cells.

The supernatants of multiclones, subclones and recombinant antibodies were screened for binding to a PD-L1 antigen having the amino acid sequence according to SEQ ID NO: 1 by enzyme-linked immunosorbent assay (FIG. 1). The initial screen resulted in the identification of one antibody clone MKP1A07310 which was then further characterized by means of Western blotting and immunohistochemistry on FFPE tissue sections.

Example 2: Characterization of Antibodies by Western Blotting

Antibody clone MKP1A07310 was analyzed by Western blotting on lysates of cell lines A549, MDA-MB 231, PD-L1 knockdown MDA-MB 231, and human PD-L1 transfected HEK293 (=HEK293_PDL1) cell lines to assess its specificity. A549 and MDA-MB 231 cell lines were retrieved from the cell bank at Merck KGaA, Darmstadt. The knockdown of human PD-L1 in MDA-MB 231 cells was performed at Merck, Darmstadt using siRNA against PD-L1 (siGENOME SMARTpool, Dharmacon). The polyclonal antibody anti-CD274 (Abcam, catalogue no. 58810) was used as positive control antibody for the detection of PD-L1 (=CD274). Primary rabbit antibodies were detected with Alexa Fluor conjugated goat anti-rabbit antibody (Invitrogen, catalog no. 21076). Western Blots were scanned using Odyssey scanner (LI-COR, USA).

Western blotting was performed on cell lysates of PD-L1 transfected HEK293, PD-L1 expressing MDA-MB 231, siRNA PDL1 knockdowns of MDA-MB 231 and the PD-L1 low cell line A549. The Western Blots showed a specific labeling of PD-L1, that was reduced in the siRNA PD-L1 knockdown MDA-MB 231 (see FIG. 2). PD-L1 protein has a MW of approximately 40 kDa. Due to a high degree of glycosylation the MW of glycosylated PD-L1 is ~52 kDa. The polyclonal positive control antibody (anti-CD274, diluted 1:250) showed several bands in addition to the specific 52 kDa band indicating that this antibody has a low selectivity for PD-L1. In comparison to the polyclonal antibody, the monoclonal recombinant antibody is highly selective.

Example 3: Antibody Cloning mRNA from hybridoma cells of the inventive clone MKP1A07310 was isolated using TurboCapture Kit (Qiagen: Catalog #72232) following the manufacturer's recommendations and reverse transcribed into cDNA using oligo-dT primer. The variable region of heavy chain (VH) was PCR amplified using proprietary Epitomics primers OYZ64-2 and OYZvh3. The entire light chain (LC) was PCR amplified using proprietary primers OYZ62 and OYZ71. The VH region of PCR fragments was digested using restriction enzyme HindIII and KpnI. The LC PCR fragments were digested using HindIII and NotI. Following the restriction digest, the resulting fragments were purified using a Qiagen PCR cleaning up kit (catalog #28016) and the resulting purified VH and LC fragments were ligated into the corresponding heavy or light chain a proprietary pTT expression vector and transformed into competent E. coli DH5α cells (MC Lab, catalog # DA-100). Resulting bacterial colonies were picked and inserts were confirmed (by expected size: approximately 440 bp for VH and 740 bp for LC) using the corresponding restriction enzymes. Plasmids with inserts of the expected size were sequenced using TT5-specific sequencing primers. Following sequence verification the entire light chain and heavy chain fragments were excised from the corresponding vector with HindIII and NotI and subsequently purified using Qiagen PCR cleaning up kit.

Example 4: Assessment of Antibody Specificity

In order to establish that the inventive antibody MKP1A07310 as well as antibody MKP1B19610 specifically bind to human PD-L1, siRNA experiments using MDA-MB 231 cells were done. For MDA-MB 231 cells it has been shown that this cell line possesses a high baseline PD-L1 expression (see e.g. Cancer Immunol Res. 2014 Apr.; 2(4): 361-370). Immunohistochemical staining of siRNA transfected MDA-MB 231 cells showed that both antibodies tested specifically recognized and bound to PD-L1 (see: FIG. 3): Upon transfection of siRNA1, or siRNA2 the antibody staining for PD-L1 was strongly reduced (see: FIG. 3, "PDL1_SP+", "PDL1_SP"). This initial determination of the binding specificities of both antibodies already indicated that MKP1B19610 appeared to be less sensitive, since greater antibody concentrations were required (5 µg/ml or greater) to result in comparable staining intensities as observed for the inventive antibody MKP1A07310 (e.g. at a concentration of 0.2 µg/ml).

For the assessment of the specificity of the inventive antibody clone MKP1A07310 by means of immunohistochemistry a tissue microarray (TMA) generated out of positive and negative control tissue with known PD-L1 protein expression was used. For the construction of a tissue microarray, human normal and tumor tissue with different PD-L1 expression levels were selected. The expression of PD-L1 was analyzed previously on a frozen tissue microarray of human organs (BioChip, Indivumed GmbH) and on frozen human tumors using the inventive anti-PD-L1 antibody. Paraffin blocks of PD-L1 positive and negative normal human tissues were purchased from provitro GmbH (Germany). From selected patients with high or low PD-L1 expression, the corresponding paraffin blocks of non-small-cell lung carcinoma (NSCLC) tumors were purchased from Indivumed GmbH (Germany). Out of each paraffin block two punches of 1.5 mm in diameter were taken and mounted upright on an adhesive tape and incorporated in liquid paraffin (see e.g. FIG. 7).

Immunohistochemistry on FFPE Tissue or Tissue/Cell Line Arrays

Sections of 3 µm of FFPE tissue or tissue/cell microarrays were mounted on positively charged SuperFrost® Plus slides (Menzel-Glaser, Braunschweig, Germany). The immunohistochemical staining procedure, starting with the deparaffinization of sections was done with the staining instrument Discovery™, or Discovery® XT (Ventana MedicalSystems, Inc., Tucson, USA; see diagram below). After deparaffinization, sections were heated for epitope retrieval in Tris-EDTA buffer pH 8. Endogenous peroxidase was blocked by incubation in 3% hydrogen peroxide (part of OmniMap™ Kit, Ventana Medical Systems). Sections were incubated with in PBS diluted antibodies and then with the secondary antibody, the HRP conjugated polymers of the OmniMap Kit, for 16 min at 37° C. Horseradish peroxidase (HRP) catalyzes the 3,3'-diaminobenzidine tetrahydrochloride (DAB)/H202 reaction to produce an insoluble dark brown precipitate that can be visualized. A monoclonal rabbit IgG antibody served as negative control. Sections were counterstained with hematoxylin. Slides were washed in tap water, dehydrated, and mounted with glass coverslips in permanent mounting media Entellan® Neu (VWR, Germany).

Immunohistochemical Staining Procedure on Discovery™ Instruments

For the immunohistochemical staining of the FFPE tissues the following Discovery™ platforms (Ventana Medical Systems, INc.) were used: Catalog No. 750-200, 750-800, Catalog No F-DISXT-750-000, according to the following steps:
Tissue/Probe: Human tissue, cancer cell lines in vitro,
Preservation: FFPE (4% paraformaldehyde pH 7, paraffin embedded)
Section thickness: 3 μm for FFPE tissue
1. Baking and Deparaffinization of Sections
Baking of slides during 8 min at 75° C.
Deparaffinization of slides during 8 min at 75° C.
2. Blocking Blocking of Endogene Peroxidase is Prior to Proteinase Antigen Retrieval and
after heat antigen retrieval in the Discovery staining instrument
Blocking of endogene peroxidase with 3% H202 at 37° C.
3. Pretreatment of Sections for Antigen Retrieval
standard CC1 (Tris EDTA buffer pH 8) during 48 min at 96° C.
4. Incubation with Primary Antibody
Primary Antibody: PDL1 (inventive antibody MKP1A07310)
Company: Merck KGaA, Darmstadt
Catalogue no: MKP-1A-73-10
Isotype: rabbit monoclonal recombinant
Clone: MKP1A07310
Dilution or Concentration: 1-2 μg/ml
Incubation during 32 min at 37° C.
Negative control for primary antibody
is: rabbit mAb IgG isotype control, clone DA1E (NEB, #3900)
5. Incubation with Secondary Antibody
Secondary Antibody: anti-rabbit IgG from OmniMap anti-rabbit HRP
Company: Ventana
Catalogue no: 760-4311
Dilution: VMSI Dispenser (unknown)
Incubation during 16 min at 37° C.
6. Incubation with Tertiary Antibody or Detection Kit Used
Antibody/Kit:
OmniMap anti-rabbit HRP (#760-4311, VMSI), ChromoMap (#760-159, VMSI) Duration of the incubation, temperature, and washing steps of the ChromoMap (DAB, copper) is set by the Discovery instrument
7. Counterstain Hematoxylin II (#790-2208, VMSI) During 8 Min at 37° C.
Bluing by instrument Washing steps are not included in the diagram. Reagents for deparaffinization, antigen retrieval, washing of slides are from VMSI (Ventana Medical Systems, Inc.). Antibodies are diluted in PBS.

Image Analysis

Immunohistochemical stainings were scanned with the help of the MiraxSCAN (Zeiss, Germany) with a resolution x/y: 1 pixel=0.23×0.23 μm². The MiraxScan instruments calibrates brightness for every slide prior to scanning. Images were taken with the help of the MiraxViewer software. The scannings were analysed with the image analysis software Visiopharm Integrator System (VIS). Viable tissue area was outlined avoiding obvious necrotic areas and connective tissue.

For the determination of the amount of antigen present, positive brown stained area was calculated as percent area of the viable tissue area. Antibody staining (arbitrary units) is calculated as Antibody staining (AU)=Positive area (%)*(255−Intensity)/100 of the brown color, whereby the positive area was calculated as Positive area (%)=100*[brown area/(brown area+blue area)], and intensity was set as the mean grey value of the brown area (see FIG. 7A, arrows in the most right image indicate brown cells, arrows the middle image indicate the software-based detection of the brown chromogen, right image: detection of blue staining of nuclei and cytoplasm).

Example 5: Intra- and Inter-Run Variability of MKP1A07310 and MKP1B19610

The inventive antibody MKP1A07310 and the antibody MKP1B19610 were characterized in two concentrations each on a cancer cell line array out of 70 cell lines to compare their binding characteristics and determine the optimum concentrations for further studies. The cancer cell line array CAX09_70 showed a continuous range of binding of the antibodies. In ~50% of the cell lines the signal was zero or very low. The highest binding of the antibodies showed Hs746T cells (Met amplified cell line). The antibody MKP1A07310 showed only minor increase of signal intensity upon increasing its concentration from 1 to 2 μg/ml, indicating that 1 μg/ml was already near the saturating concentration. Antibody MKP1B19610 showed substantial increase in signal from 5 to 10 μg/ml. Higher concentrations were not tested, because antibodies tend to bind unspecifically onto tissue and glass at concentrations >10 μg/ml. The binding of the antibodies MKP1A07310 and MKP1B19610 on the 70 cell lines correlate with a Pearson coefficient of r=0.95.

Figure 6:
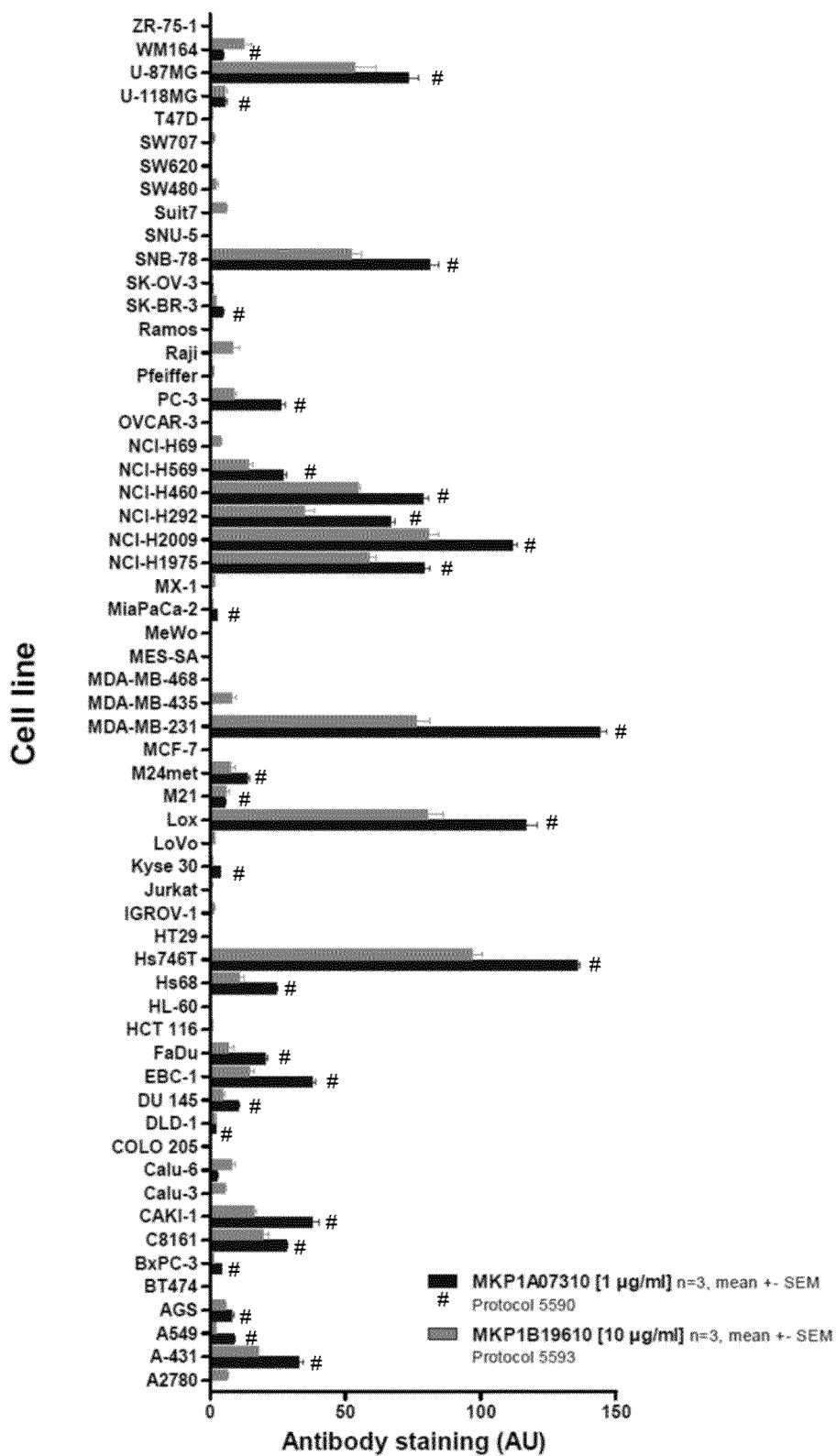
FIG. 6: Characterization of the inventive antibody (MKP1A07310, marked by "#") and one antibody directed against an extracellular epitope of human PD-L1 MKP1A7310 at a concentration of 1 µg/ml and MKP1B19610 at a concentration of 10 µg/ml.
Figure 9:
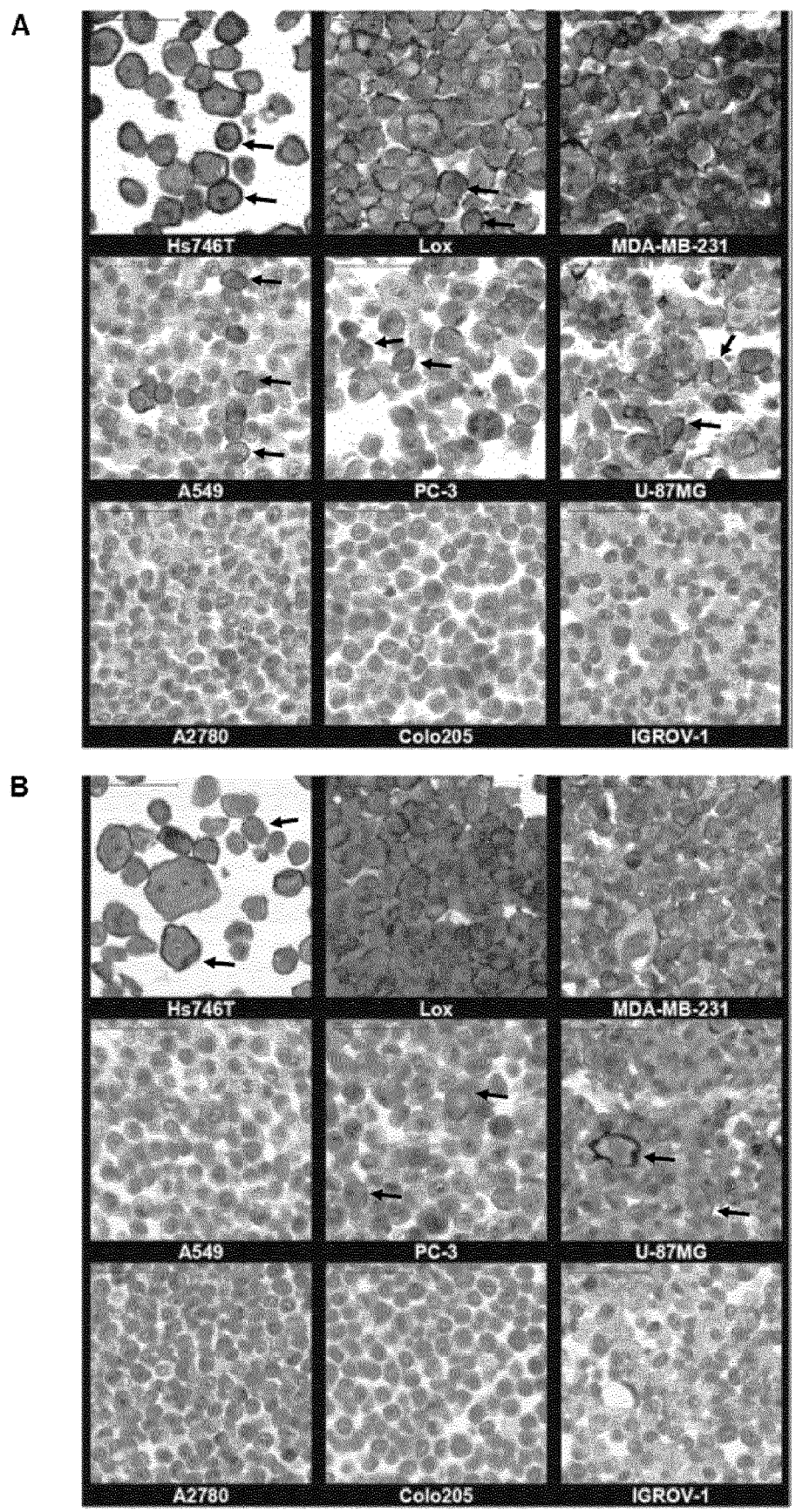
FIG. 9: (A) Immunohistochemical staining using the inventive antibody MKP1A07310 at a concentration of 1 µg/ml on FFPE tissue of the cancer cell line array CAX08_60. (B) Immunohistochemical staining using an antibody directed against an extracellular epitope of human PD-L1 (MKP1B19610) at a concentration of 10 µg/ml on FFPE tissue of the cancer cell line array CAX08_60. Arrows indicate exemplary PD-L1 positive cells.
Figure 10:
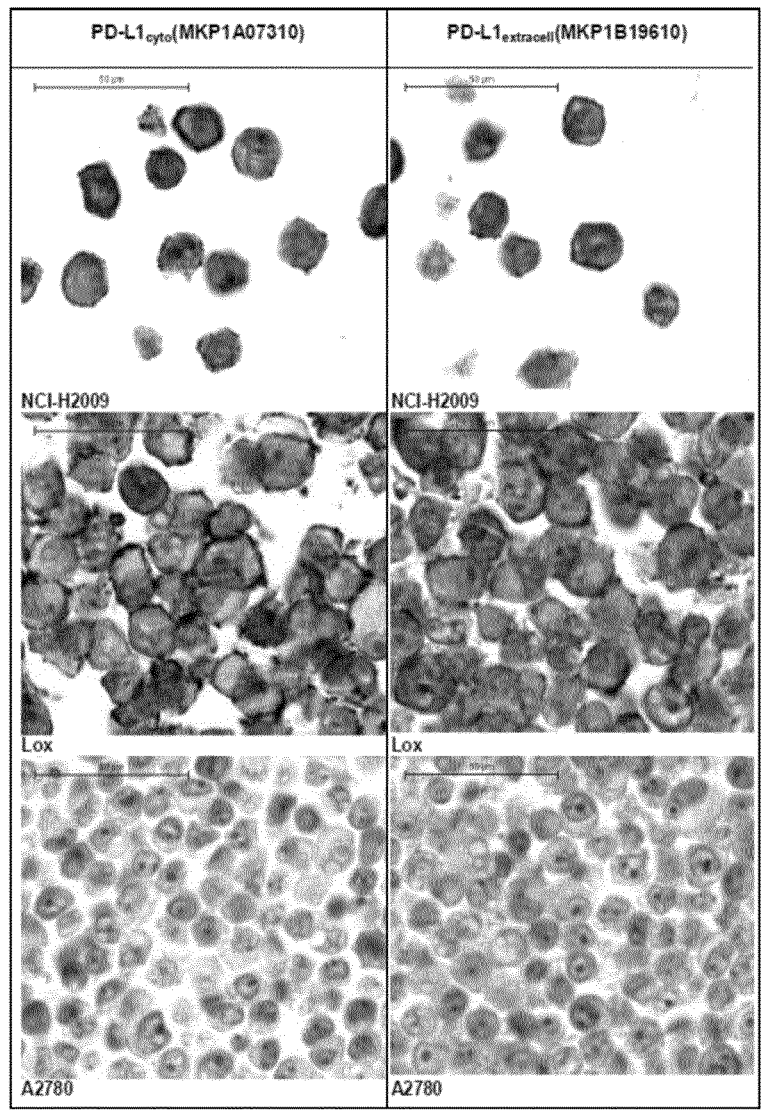
FIG. 10: Immunohistochemical staining using the inventive antibody MKP1A07310 at a concentration of 1 µg/ml, and the antibody MKP1B19610 directed against an extracellular epitope of PD-L1 at a concentration of 10 µg/ml on a discovery XT staining instrument on FFPE fixed cell lines NCI-H2009, Lox and A2780 (NCI-H2900, Lox cancer cell lines express high levels of PD-L1, cancer cell line A2780 only minor amounts of PD-L1).

Intra-run and inter-run variability of immunohistochemical staining using the two antibodies on the Discovery XT staining instrument were performed on a cell line array out of 60 cell lines, CAX08_60 (FIG. 6). Antibody MKP1A07310 was tested at a concentration of 1 μg/ml and antibody MKP1B19610 at 10 μg/ml. On the cell lines of the CAX08_60 the staining of MKP1A07310 correlated with MKP19610 with a Pearson coefficient of r=0.97. In cell lines showing a medium to low overall staining signal, like A549, PC-3 or U-87 MG, cells showing high staining were dispersed between negative cells (FIG. 9A: MKP1A07310; FIG. 9B: MKP1B19610).

Figure 5:
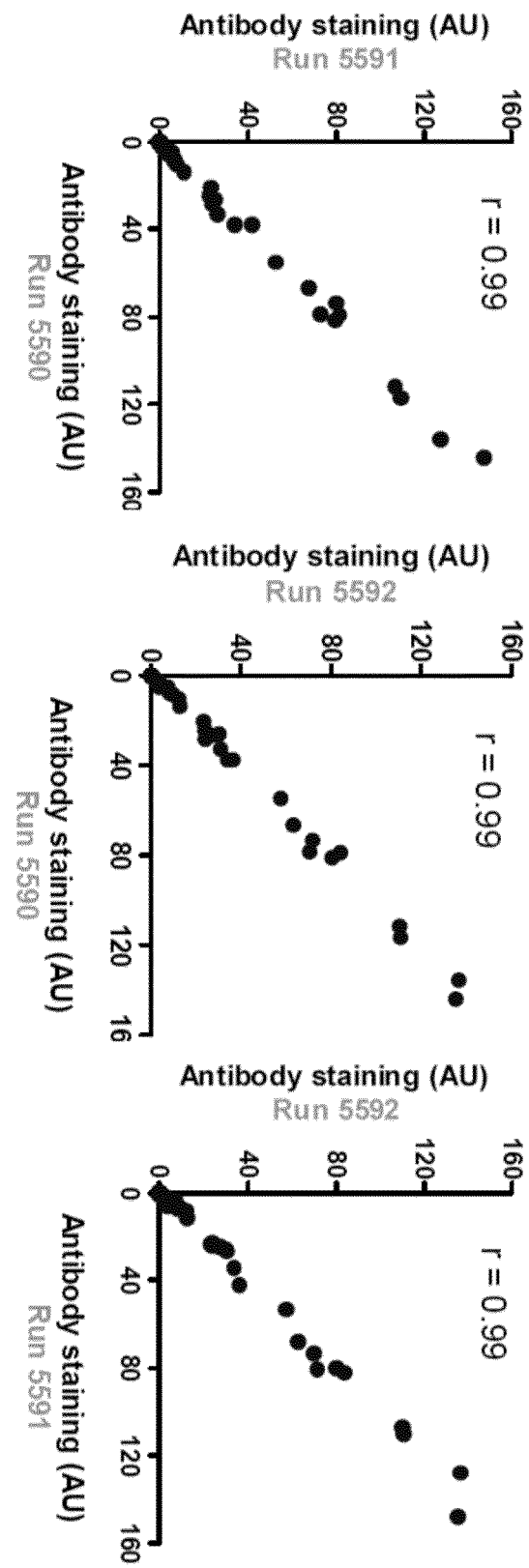
FIG. 5: Intra-run variability of the inventive antibody (MKP1A07310) on tissue array CAX08_60, correlation coefficients of r=0.99 between different slides.

Intra-run variability of the inventive antibody MKP1A07310 was low, with correlation coefficients of r=0.99 between different slides (FIG. 5). MKP1B19610 showed a slightly higher intra-run variability, with correlation coefficients ranging from 0.93 to 0.99 between different slides. Inter-run variability between 3 different runs was low with r=0.99 for MKP1A07310 and r>=0.98 for MKP1B19610.

Figure 8:
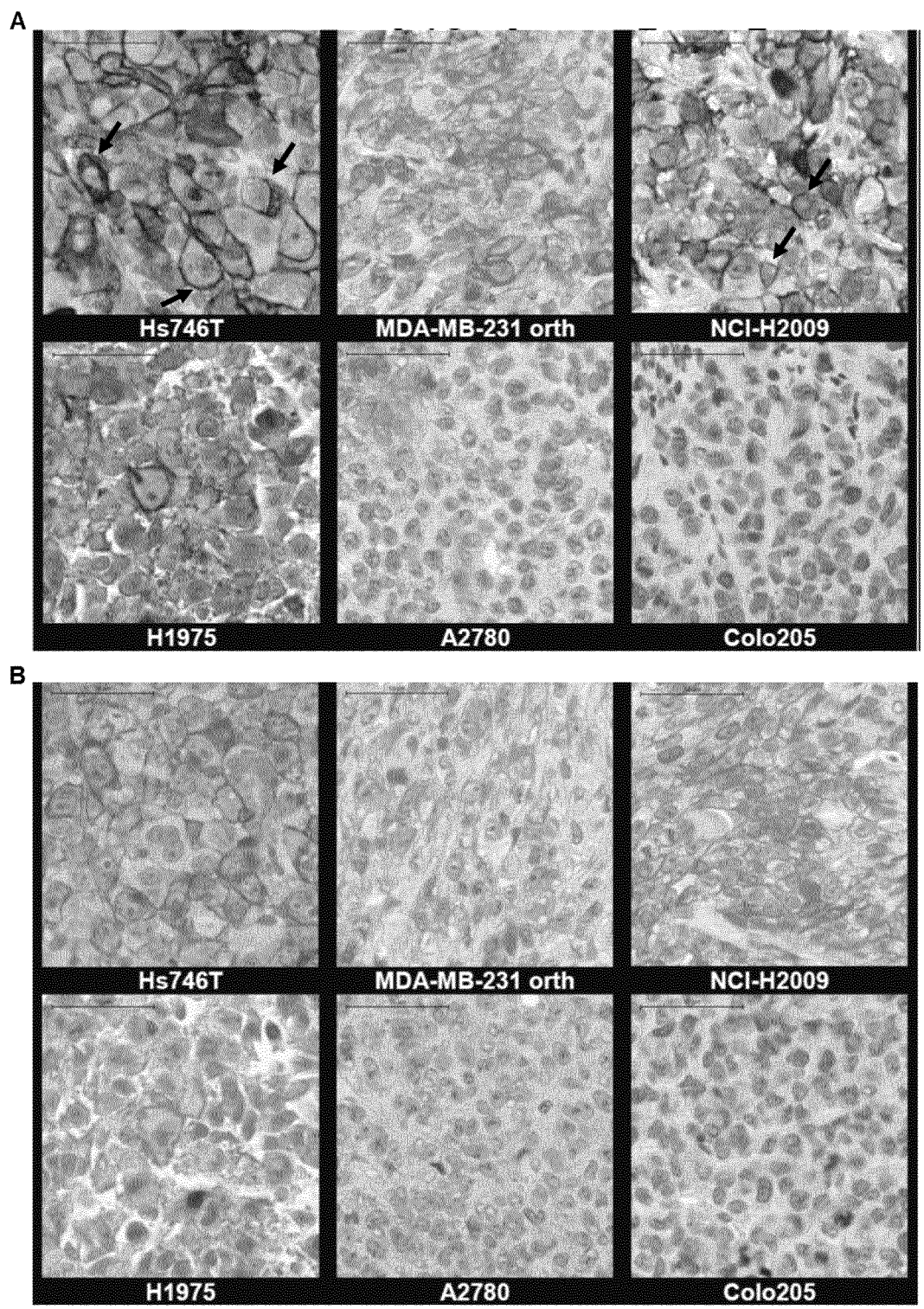
FIG. 8: (A) Immunohistochemical using the inventive antibody MKP1A07310 on FFPE tissue of the xenograft tissue microarray TMA_Xenos_12 at a concentration of 2 µg/ml. (B) Immuno-histochemical staining using an antibody directed against an extracellular epitope of human PD-L1 (MKP1B19610) at a concentration of 10 µg/ml on FFPE tissue of the xenograft tissue microarray TMA_Xenos_12. Exemplary PD-L1 positive cells are indicated by arrows

The recombinant antibodies were additionally tested on tissue microarrays comprised out of 48 different xenografts (TMA_Xenos_12, FIG. 8). Staining with MKP1A07310 correlated with MKP1B19610 with a correlation coefficient of r=0.90. High expressing xenografts were Hs746T, MDA-MB 231, NCI-H2009, and H1975. Negative examples were A2780 and Colo205.

Example 6: Comparison of MKP1A07310 and MKP1B19610 Using Different IHC Platforms Aim of the study was to compare the binding characteristics of the antibodies using the AutostainerLink 48 together with the PT Link modules for antigen retrieval from Dako (Dako GmbH, Germany) with the stains using the instrument Discovery XT. The reagents used by Dako or Ventana Medical Systems, Inc. (VMSI) for deparaffinization, antigen retrieval, dilution of antibodies on the slide, washing buffer, and detection systems differ and might influence the "epitope world" of the antibodies Substrates A tissue microarray out of positive and negative control tissue for PD-L1, the TMA_PDL1_11, and a cell line microarray out of 59 human cancer cell lines and 1 insect cell line, CAX08_60, were used as a test matrix. The TMA_PDL1_11 was used for the selection of the antibodies generated. Sections of 3 µm of formaldehyde fixed paraffin embedded (FFPE) tissue or tissue/cell microarrays were mounted on positively charged SuperFrost® Plus slides (Menzel-Gläser, Braunschweig, Germany).

Antibodies Used:

Primary antibodies: The inventive antibody MKP1A07310 ("7310 mAb") and MKP1B19610 were used diluted into PBS: MKP1A07310 was used concentrations of 1, 2 and 5 µg/ml; antibody MKP1B19610 was used at concentrations of 2, 5, and 10 µg/ml;

Secondary Antibodies

| Antigen | Antibody | Vendor | Conc./dilution | Incubation |
|---|---|---|---|---|
| Rabbit IgG | Oligomer, HRP coupled (OmniMap) | VMSI#760-4311 | Dispenser | 16 min @ 37° C. |
| Rabbit IgG | Oligomer, HRP coupled (EnVision Flex/HRP) | Dako, #SM802 | Dispenser | 30 min @ RT |

Staining Procedures
Antigen Retrieval

Antigen retrieval was done as follows: For the Discovery XT antigen retrieval was done using "High pH" antigen retrieval conditions (Tris-EDTA pH 8), for the AutostainerLink, testing started by using "High pH" (Tris-EDTA buffer, pH 9) antigen retrieval. For antibody PD-L1 MKP1B19610) in addition "Low pH" (Citrate buffer, pH 6.1) antigen retrieval was used.

Staining Procedure for Discovery XT Staining Instrument

The immunohistochemical staining procedure starting with the deparaffinization of sections was done with the staining instrument Discovery® XT (Ventana Medical Systems, Inc., ("VMSI") Tucson, USA). After deparaffinization sections were heated for epitope retrieval in Tris-EDTA buffer pH 8 at 96° C. for 48 min. Endogenous peroxidase was blocked by incubation in 3% hydrogen peroxide (part of OmniMap™ Kit, Ventana Medical Systems). Sections were incubated with in PBS diluted antibodies and then with the secondary antibody, the HRP conjugated polymers of the OmniMap Kit (Discovery) for 16 min at 37° C. Horseradish peroxidase (HRP) catalyzes the 3,3'-diaminobenzidinetetrahydorchloride (DAB)/$H_2O_2$ reaction to produce an insoluble dark brown precipitate that can be visualized. Sections were counterstained with hematoxylin. The inventive anti-PD-L1 antibody was used in concentrations of 1, 2 and 5 µg/ml; antibody MKP1B19610 was used at 2, 5, and 10 µg/ml; for both antibodies detection was done using OmniMap anti-rabbit HRP (#760-4311, VMSI) and ChromoMap (#760-159).

Staining Procedure for AutostainerLink 48

Deparaffinization and antigen retrieval of sections was done in the PT link pretreatment module (Dako GmbH, Germany). Slides were deparaffinated during heating for epitope retrieval in Tris-EDTA buffer pH 9 (High pH) or in citrate buffer pH 6.1 (Low pH) at 97° C. during 20 min. After heat antigen retrieval, slides were transferred into the AutostainerLink 48 instrument. Endogenous peroxidase was blocked by incubation in 3% hydrogen peroxide. Sections were incubated with in PBS diluted antibodies and then with the secondary antibody, the HRP conjugated polymers of the EnVision FLEX (SM802, Dako) for 30 min at room temperature. Horseradish peroxidase (HRP) catalyzes the 3,3'-diaminobenzidine tetrahydrochloride (DAB)/$H_2O_2$ reaction to produce an insoluble dark brown precipitate that can be visualized. Sections were counterstained with hematoxylin. Slides were subsequently washed in tap water, dehydrated, and mounted with glass coverslips in permanent mounting media Entellan® Neu (VWR, Germany). MKP1A07310 was used at concentrations of 0.5, 1 and 2 µg/ml, MKP1B19610 at concentrations of 0.2, 0.5, 1, 2, and 5 µg/ml.

Comparison of MKP1A07310 and MKP1B19610 on Different Staining Platforms

Figure 11:
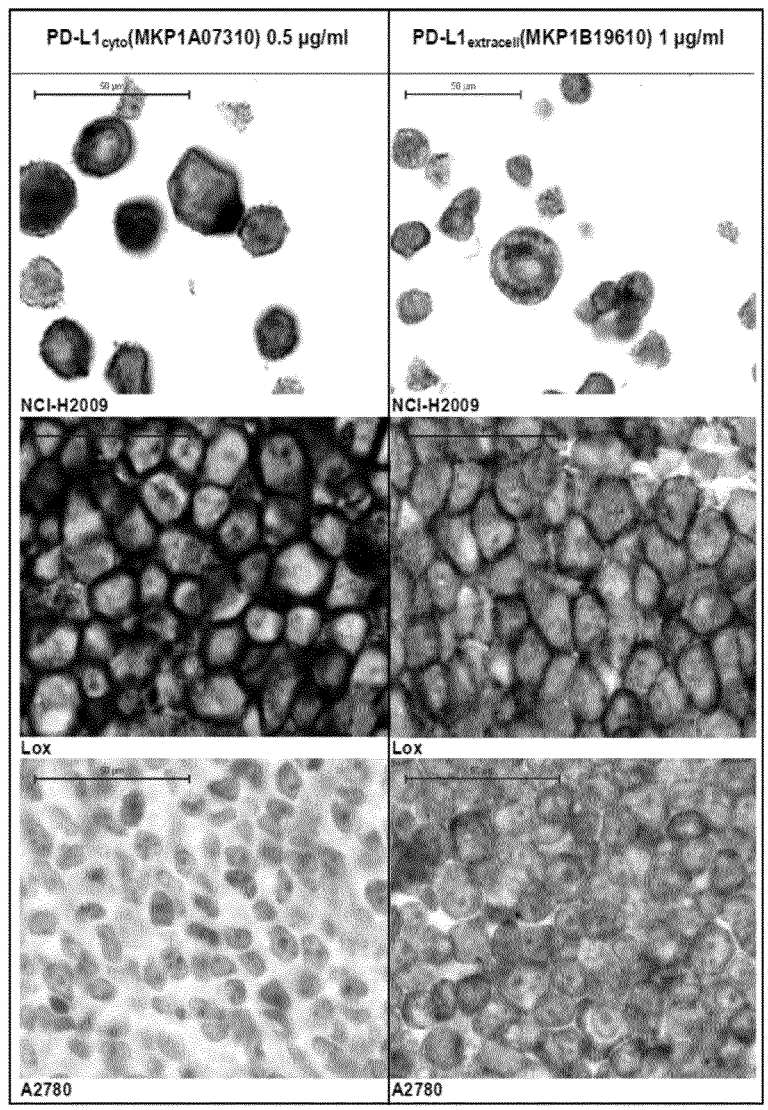
FIG. 11: Immunohistochemical staining using the inventive antibody MKP1A07310 at a concentration of 0.5 µg/ml, and the antibody MKP1B19610 directed against an extracellular epitope of PD-L1 at a concentration of 1 µg/ml on an Autostainer Link staining instrument on FFPE fixed cell lines NCI-H2009, Lox and A2780.
Figure 14:
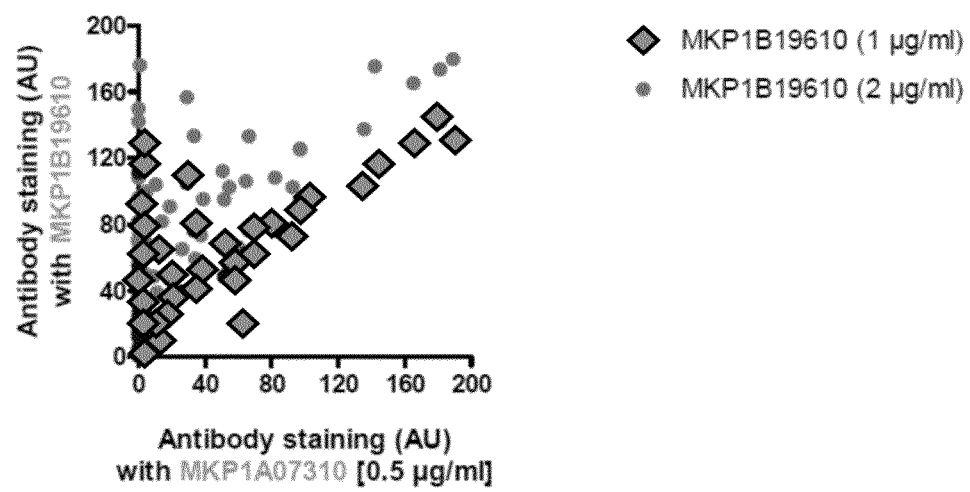
FIG. 14: (A) IHC correlation between the anti-PD-L1 antibody MKP1B19610 and the inventive antibody MKP1A07310 on FFPE cancer cell lines stained with the AutostainerLink (DAKO) at the concentrations indicated (diamonds: 1 µg/ml; circles: 2 µg/ml), the inventive antibody was used at a concentration of 0.5 µg/ml as indicated. (B) statistical analysis of the correlation of the IHC results with correlations coefficients of r=0.6503 (at 2 µg/ml MKP1B19610) and r=0.7088 (at 1 µg/ml MKP1B19610).

Using the AutostainerLink, the correlation of IHC results obtained with the anti-PD-L1 antibody MKP1B19610 and the inventive anti-PD-L1 antibody MKP1A07310 was low with r<0.71 (FIGS. 11 and 14). There was still a correlation of staining intensities in certain cell lines, as for example NCI-H2009 and Lox (see: FIG. 11), but for A2780 cells that serve as negative control for PD-L1 expression, anti-PD-L1 antibody MKP1B19610 indicates PD-L1 expression, whereas the same cell line is negative for PD-L1 expression using the inventive antibody (see: FIG. 11).

Figure 13:
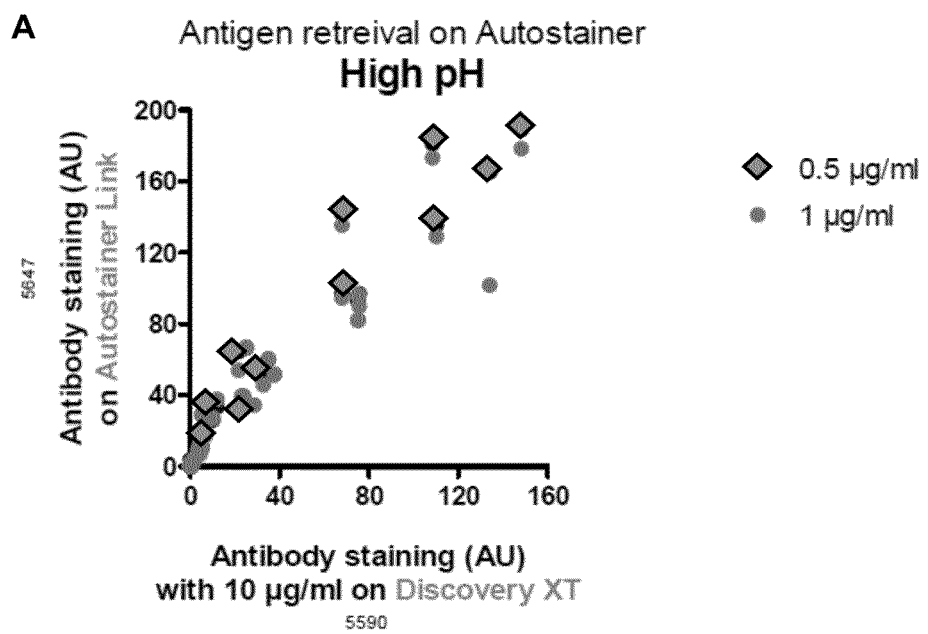
FIG. 13: (A) Correlation of IHC results using the inventive anti-PD-L1 antibody MKP1A07310 on FFPE cancer cell lines stained on a Discovery XT® System (Ventana) or AutostainerLink (DAKO) at high pH using the antibody concentrations as indicated. (B) Statistical analysis of the correlation of the IHC results with correlations coefficients of r=0.9474 (at 1 µg/ml) and r=0.9695 (at 2 µg/ml).

A comparison of the staining characteristics of the inventive anti-PD-L1 antibody (MKP1A07310) on the Discovery XT system with its characteristics using the AutostainerLink, revealed a high correlation of the IHC staining intensities on the cancer cell lines used with a correlation coefficient of r=0.96 at 0.5 µg/ml (FIG. 13). Based on the present data, the reagents that were used according to the guidelines by Dako for use with the AutostainerLink for deparaffinization, antigen retrieval and staining did not alter the IHC staining pattern by e.g. unmasking aberrant binding sites for the inventive anti-PD-L1 antibody (MKP1A07310) when compared to the outcome of the IHC staining using Ventana's Discovery XT platform and Ventana reagents, except for increased IHC staining signals.

Figure 12:
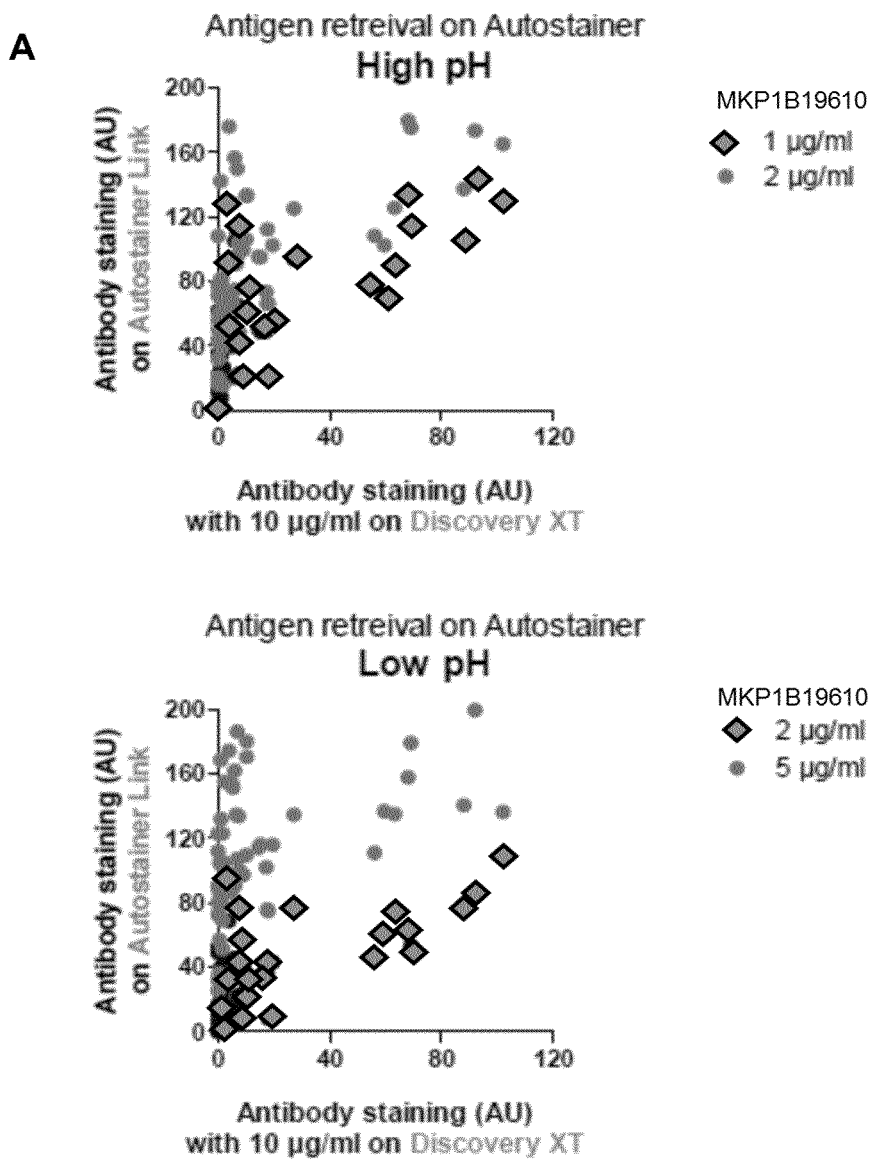
FIG. 12: Correlation of IHC results using MKP1B19610 on FFPE cancer cell lines stained using the Discovery XT® System (Ventana) and the AutostainerLink system (DAKO). (A) results of the IHC runs using MKP1B19610 at low and high pH using the different IHC platforms and concentratins as indicated plotted against each other. (B) Statistical analysis of the diagrams, with Pearson correlation coefficients of 0.6186 (2 µg/ml, high pH), 0.6969 (1 µg/ml, high pH) and at low pH 0.4309 (5 µg/ml), 0.6631 (2 µg/ml).

Comparing the staining characteristics of the anti-PD-L1 antibody MKP1B19610 which is directed against an extracellular epitope of human PD-L1 on the Discovery XT System with its characteristics using the AutostainerLink (Dako), revealed a far lower correlation of the IHC staining intensities in the cancer cell lines used with a correlation coefficient of r<0.67 (FIG. 12). Using "Low pH" antigen retrieval, the correlation was even lower than for the IHC staining conditions "High pH" (see e.g. FIG. 12 B, "low pH", r=0.43 at an antibody concentration of MKP1B19610 of 5 µg/ml and r=0.66 at an antibody concentration of MKP1B19610 of 1 µg/ml.) There was still a correlation of IHC staining intensities in many cell lines assessed, but a group of cells, that are negative on the Discovery XT System assayed positive for PD-L1 expression using the AutostainerLink as is shown for A2780 (see e.g. FIG. 11).

In conclusion, using the AutostainerLink platform with reagents from Dako, the inventive antibody directed against the cytoplasmic domain of PD-L1 (MKP1A07310) did show the same binding characteristics in 55 FFPE cancer cell lines as on the Discovery XT staining platform from Ventana Medical Systems. In contrast, additional binding sites of the antibody MKP1B19610, generated against the extracellular domain, were unmasked using the AutostainerLink instead of the Discovery XT. Thus, the inventive antibody can surprisingly be used on both widely used commercial IHC platforms, the AutostainerLink platform (DAKO) as well as on the Discovery XT staining platform from Ventana Medical Systems.

In addition, as shown in FIG. 5, the inter-run variability of the staining results obtained using the inventive antibody is surprisingly low as indicated by a correlation efficient of r=0.99 such that the IHC staining and e.g. the derived scoring of the PD-L1 expression in a FFPE tumor tissue as disclosed herein, will be comparable between different staining runs. The inventive antibody thus meets the unmet need of an anti-PD-L1 antibody which is able to reliably detected PD-L1 expression in FFPE tumor tissue samples (e.g. derived from biopsies) that are routinely used in pathology on two commonly used IHC platforms (e.g. Discovery XT® System, Ventana and AutostainerLink, Dako).

The invention claimed is:

1. An antibody, or antigen-binding fragment thereof, that binds to an epitope comprised in the amino acid sequence according to SEQ ID NO: 1, wherein the antibody light chain, or antigen-binding fragment thereof, comprises sequences SEQ ID NO: 4, SEQ ID NO: 6, and SEQ ID NO: 8 and the antibody heavy chain, or antigen-binding fragment thereof, comprises sequences SEQ ID NO:10, SEQ ID NO: 12, and SEQ ID NO: 14.

2. The antibody, or antigen-binding fragment thereof, according to claim 1, wherein the antigen-binding fragment is selected from the group consisting of an Fab, an F(ab')$_2$, an Fab', an scFv, and a di-scFv.

3. The antibody, or antigen-binding fragment thereof, according to claim 1, wherein the antibody is a monoclonal antibody.

4. The antibody, or antigen-binding fragment thereof, according to claim 1, wherein the antibody light chain or antigen-binding fragment thereof further comprises SEQ ID NO: 3, SEQ ID NO: 5, and SEQ ID NO: 7.

5. The antibody, or antigen-binding fragment thereof, according to claim 1, wherein the antibody heavy chain or antigen-binding fragment thereof further comprises SEQ ID NO: 9, SEQ ID NO: 11, and SEQ ID NO: 13.

6. The antibody, or antigen-binding fragment thereof, according to claim 1, wherein the antibody heavy chain or antigen-binding fragment thereof comprises the amino acid sequence according to SEQ ID NO: 110 and the antibody light chain or antigen-binding fragment thereof comprises the amino acid sequence according to SEQ ID NO: 111.

7. The antibody, or antigen-binding fragment thereof, according to claim 6, wherein the antibody light chain comprises the amino acid sequence according to SEQ ID NO: 15 and the antibody heavy chain comprises the amino acid sequence according to SEQ ID NO: 16.

8. The antibody, or antigen-binding fragment thereof, according to claim 6, wherein the antibody light chain comprises the amino acid sequence according to SEQ ID NO: 114 and the antibody heavy chain comprises the amino acid sequence according to SEQ ID NO: 115.

9. The antibody, or antigen-binding fragment thereof, according to claim 6, wherein the antibody is a rabbit antibody, or a rabbit-derived antibody.

10. The antibody, or antigen-binding fragment thereof, according to claim 1, wherein said antibody, or antigen-binding fragment thereof, is further coupled to a detectable label selected from the group consisting of an enzyme, a fluorophore, and a radioisotope.

11. The antibody, or antigen-binding fragment thereof, according to claim 1, for use in detecting the presence or expression of an epitope comprised in SEQ ID NO: 1 in a sample, wherein the detection is selected from the group consisting of flow cytometry, enzyme-linked immunosorbent assay (ELISA), western blotting, and immunohistochemistry (IHC).

12. A method of detecting the presence, or expression of, human PD-L1, or any fragment thereof, comprising the amino acid sequence according to SEQ ID NO: 1 in a sample, wherein the method comprises the step of contacting a sample with an antibody, or antigen-binding fragment thereof, wherein the antibody light chain, or antigen-binding fragment thereof, comprises sequences SEQ ID NO: 4, SEQ ID NO: 6, and SEQ ID NO: 8 and the antibody heavy chain, or antigen-binding fragment thereof, comprises sequences SEQ ID NO: 10, SEQ ID NO: 12, and SEQ ID NO: 14, and detecting the presence of bound antibody, or antigen-binding fragment thereof.

13. The method according to claim 12, wherein said sample is acquired from a subject having, or at risk of, cancer; a subject having T-cell dysfunction; a subject having an acute or a chronic infection; or a subject being at risk of, or showing, tumor immunity.

14. An expression vector comprising a polynucleotide encoding an antibody, or antigen-binding fragment thereof, wherein the antibody light chain, or antigen-binding fragment thereof, comprises sequences SEQ ID NO: 4, SEQ ID NO: 6, and SEQ ID NO: 8 and the antibody heavy chain, or antigen-binding fragment thereof, comprises sequences SEQ ID NO: 10, SEQ ID NO: 12, and SEQ ID NO: 14.

15. An isolated host cell comprising at least one expression vector comprising a polynucleotide encoding an antibody, or antigen-binding fragment thereof, wherein the antibody light chain, or antigen-binding fragment thereof, comprises sequences SEQ ID NO: 4, SEQ ID NO: 6, and SEQ ID NO: 8 and the antibody heavy chain, or antigen-binding fragment thereof, comprises sequences SEQ ID NO: 10, SEQ ID NO: 12, and SEQ ID NO: 14.

16. A method of treating cancer in a patient comprising the steps of:
(i) detecting the presence or expression of human Programmed cell death 1 ligand 1 (PD-L1) in a sample comprising contacting said sample with an antibody, or antigen-binding fragment thereof, wherein the antibody light chain, or antigen-binding fragment thereof, comprises sequences SEQ ID NO: 4, SEQ ID NO: 6, and SEQ ID NO: 8 and the antibody heavy chain, or antigen-binding fragment thereof, comprises sequences SEQ ID NO: 10, SEQ ID NO: 12, and SEQ ID NO: 14, and detecting the presence of bound antibody, or antigen-binding fragment thereof,
(ii) comparing the results of said PD-L1 expression from (i) to a reference sample, and
(iii) administering an immune checkpoint inhibitor to said patient if the PD-L1 expression in the sample as detected in step (i) is increased compared to the reference sample.

17. The method according to claim 16, wherein the reference sample is derived or obtained from a healthy subject, not inflicted with cancer.

18. The method according to claim 16, wherein the immune checkpoint inhibitor of step (iii) which is administered to the patient is an anti-PD-L1 antibody, an anti-PD-1 antibody, or a fragment thereof.

19. The method according to claim 16, wherein the immune checkpoint inhibitor is administered in a dose from about 5 mg/kg body weight to about 30 mg/kg body weight.

20. The method according to claim 16, wherein the immune checkpoint inhibitor is administered in a flat dosing regimen of 500 to 800 mg every week, or 900 to 1600 mg every two weeks, or 1250 to 2400 mg every three weeks.

* * * * *